United States Patent [19]

Borden et al.

[11] Patent Number: 5,766,848
[45] Date of Patent: Jun. 16, 1998

[54] METHODS FOR IDENTIFYING COMPOUNDS WHICH SPECIFICALLY BIND A HUMAN BETAINE/GABA TRANSPORTER

[75] Inventors: Laurence A. Borden, Hackensack; Kelli E. Smith, Wayne, both of N.J.; Richard L. Weinshank, New York, N.Y.

[73] Assignee: Synaptic Pharmaceutical Corporation, Paramus, N.J.

[21] Appl. No.: 291,299

[22] Filed: Aug. 16, 1994

Related U.S. Application Data

[63] Continuation-in-part of Ser. No. 1,738, Jan. 4, 1993, abandoned.

[51] Int. Cl.$^6$ ........................................... C12Q 1/68
[52] U.S. Cl. ................. 435/6; 435/7.2; 435/7.21; 436/501
[58] Field of Search ................. 435/6, 240.2, 252.3, 435/255, 7.2, 7.21, 7.8, 325, 320.1, 356, 357, 358, 354, 366, 367; 530/350; 536/23.5, 24.31; 436/501

[56] References Cited

U.S. PATENT DOCUMENTS 5,225,323  7/1993  Lam et al. .
5,424,185  6/1995  Lam et al. .

OTHER PUBLICATIONS

Wermuth et al. J. Med. Chem. 1987 30 :239–249.
Amara et al, Current Opinion in Neurobiology, Jun. 1993, 3(3):337–344.
Tunnicliff et al, Gen Pharmac. 1985, 16(1) : 25–29.
Yamauchi et al, J. Biol. Chem. Jan. 1992, 267(1) 649–652.
Giros et al, FEBS, 295(1–3) : 149–154, 1991.
Lopez–Corcuera, B. et al. Journal of Biological Chemistry 267(25): 17491–17493 (Sep. 5, 1992).

*Primary Examiner*—Marianne P. Allen
*Assistant Examiner*—Patricia A. Duffy
*Attorney, Agent, or Firm*—John P. White

[57] ABSTRACT

This invention provides an isolated nucleic acid molecules encoding mammalian betaine/GABA transporters, including a human betaine/GABA transporter. This invention further provides vectors comprising said isolated nucleic acid molecules, and mammalian cells comprising such vectors. This invention further provides isolated mammalian and human betaine/GABA transporter proteins and antibodies directed thereto. This invention provides nucleic acid molecule probes useful for detecting nucleic acid molecules encoding mammalian or human betaine/GABA transporters, antisense oligonucleotides complementary to any sequences of a nucleic acid molecules which encode a mammalian or human betaine/GABA transporter. This invention further provides pharmaceutical compounds related to mammalian and human betaine/GABA transporters, and nonhuman transgenic animals which express DNA encoding a normal or a mutant mammalian or human betaine/GABA transporter. This invention further provides methods for determining substrate binding, detecting expression, drug screening, and treatments for alleviating abnormalities associated with mammalian betaine/GABA transporters and human betaine/GABA transporters.

8 Claims, 25 Drawing Sheets

FIGURE 1A

| FIGURE 1A |
|-----------|
| FIGURE 1B |
| FIGURE 1C |
| FIGURE 1D |

```
         -200                  -180                  -160
          .                     .                     .
TTGGGACTCTCCTGGAGACCTGATGCCCACAGCCAAGCTGACCACAGGAGCCGGTGCTGG

-140                  -120                  -100
          .                     .                     .
GGACTGAGGGAAACTTAGAGTTCAGAGAGGGGGTGTGATTTGCCTGAGGTCACACAGCAA

-80                   -60                   -40
           .                     .                     .
GTTAGAGACCCAGCTCCACGACTCATTGTCTTGGCTTTGGCCCTCGTCATCCTGCCCACC

-20                    0                    20
           .                     .                     .
CAGCGGGGCTTCCCAACCCACCACACAGCCATGGACGGGAAGGTGGCAGTGCAAGAGTAT
                                  M   D   G   K   V   A   V   Q   E   Y 40                    60                    80
            .                     .                     .
GGGCCTCCTGCAGTCTCCTGGGTCCCCGAGGAGGGAGAGAAGTTGGACCAGGAAGACGAG
 G   P   P   A   V   S   W   V   P   E   E   G   E   K   L   D   Q   E   D   E 100                   120                   140
           .                     .                     .
GACCAGGTGAAGGATCGGGGCCAATGGACCAACAAGATGGAGTTTGTGCTGTCAGTGGCC
 D   Q   V   K   D   R   G   Q   W   T   N   K   M   E   F   V   L   S   V   A 160                   180                   200
           .                     .                     .
GGGGAGATCATTGGGCTGGGCAATGTCTGGAGGTTTCCCTATCTCTGCTACAAAAACGGA
 G   E   I   I   G   L   G   N   V   W   R   F   P   Y   L   C   Y   K   N   G 220                   240                   260
           .                     .                     .
GGTGGAGCCTTCTTCATCCCCTACTTCATCTTCTTCTTTGTCTGCGGCATCCCGGTGTTC
 G   G   A   F   F   I   P   Y   F   I   F   F   F   V   C   G   I   P   V   F 280                   300                   320
           .                     .                     .
TTCCTGGAGGTGGCGTTGGGCCAATACACCAGCCAAGGGAGTGTCACAGCCTGGAGGAAG
 F   L   E   V   A   L   G   Q   Y   T   S   Q   G   S   V   T   A   W   R   K 340                   360                   380
           .                     .                     .
ATCTGCCCCCTCTTCCAGGGCATTGGTCTGGCATCTGTGGTCATCGAGTCATATTTGAAT
 I   C   P   L   F   Q   G   I   G   L   A   S   V   V   I   E   S   Y   L   N 400                   420                   440
           .                     .                     .
```

FIGURE 1B

```
GTCTACTACATCATCATCCTTGCCTGGGCTCTCTTCTACCTGTTCAGCTCCTTCACCTCT
 V  Y  Y  I  I  I  L  A  W  A  L  F  Y  L  F  S  S  F  T  S 460                 480                 500
GAGCTGCCCTGGACGACCTGCAACAACTTTTGGAACACAGAGCATTGCACGGACTTTCTG
 E  L  P  W  T  T  C  N  N  F  W  N  T  E  H  C  T  D  F  L 520                 540                 560
AACCACTCAGGAGCCGGCACAGTGACCCCATTTGAGAATTTTACCTCACCTGTCATGGAA
 N  H  S  G  A  G  T  V  T  P  F  E  N  F  T  S  P  V  M  E 580                 600                 620
TTCTGGGAGAGACGAGTTCTGGGCATCACCTCGGGCATCCATGACCTGGGCTCCCTGCGC
 F  W  E  R  R  V  L  G  I  T  S  G  I  H  D  L  G  S  L  R 640                 660                 680
TGGGAGCTGGCCCTGTGCCTCCTGCTCGCCTGGGTCATCTGCTATTTCTGCATCTGGAAG
 W  E  L  A  L  C  L  L  L  A  W  V  I  C  Y  F  C  I  W  K 700                 720                 740
GGGGTCAAGTCCACAGGCAAGGTGGTTTATTTCACAGCCACGTTTCCGTACCTGATGCTT
 G  V  K  S  T  G  K  V  V  Y  F  T  A  T  F  P  Y  L  M  L 760                 780                 800
GTCATTTTGCTGATCAGAGGTGTCACCCTTCCCGGAGCCTACCAGGGCATCATCTACTAC
 V  I  L  L  I  R  G  V  T  L  P  G  A  Y  Q  G  I  I  Y  Y 820                 840                 860
TTGAAGCCAGATTTGTTCCGCCTCAAGGACCCTCAGGTGTGGATGGATGCGGGCACCCAG
 L  K  P  D  L  F  R  L  K  D  P  Q  V  W  M  D  A  G  T  Q 880                 900                 920
ATCTTCTTCTCCTTTGCCATCTGCCAGGGGTGCCTGACAGCCCTGGGCAGCTACAACAAG
 I  F  F  S  F  A  I  C  Q  G  C  L  T  A  L  G  S  Y  N  K 940                 960                 980
TATCACAACAACTGCTACAAGGACTGCATCGCCCTCTGCTTCCTGAACAGTGCCACCAGC
 Y  H  N  N  C  Y  K  D  C  I  A  L  C  F  L  N  S  A  T  S 1000                1020                1040
TTTGTGGCTGGGTTTGTTGTCTTCTCCATCCTGGGCTTCATGTCCCAAGAGCAAGGGGTG
 F  V  A  G  F  V  V  F  S  I  L  G  F  M  S  Q  E  Q  G  V
```

FIGURE 1C

```
       1060                1080                 1100
          .                   .                    .
CCCATTTCTGAAGTGGCCGAGTCAGGTCCTGGGCTGGCCTTCATCGCCTTCCCCAAGGCT
 P  I  S  E  V  A  E  S  G  P  G  L  A  F  I  A  F  P  K  A 1120                1140                 1160
          .                   .                    .
GTGACTATGATGCCCTTATCCCAGCTGTGGTCCTGCCTGTTCTTTATCATGCTCATATTC
 V  T  M  M  P  L  S  Q  L  W  S  C  L  F  F  I  M  L  I  F 1180                1200                 1220
          .                   .                    .
CTAGGGCTGGACAGCCAGTTTGTCTGTGTGGAGTGCCTGGTGACAGCCTCCATAGACATG
 L  G  L  D  S  Q  F  V  C  V  E  C  L  V  T  A  S  I  D  M 1240                1260                 1280
          .                   .                    .
TTCCCCAGGCAGCTCCGGAAGAGCGGGCGGCGCGAGCTCCTCATCCTCACCATCGCCGTC
 F  P  R  Q  L  R  K  S  G  R  R  E  L  L  I  L  T  I  A  V 1300                1320                 1340
          .                   .                    .
ATGTGCTACCTGATAGGGCTTTTCCTGGTCACCGAGGGCGGGATGTACATCTTCCAGCTG
 M  C  Y  L  I  G  L  F  L  V  T  E  G  G  M  Y  I  F  Q  L 1360                1380                 1400
          .                   .                    .
TTTGACTACTATGCTTCCAGTGGCATATGCCTGCTGTTCCTGTCATTGTTTGAAGTGGTC
 F  D  Y  Y  A  S  S  G  I  C  L  L  F  L  S  L  F  E  V  V 1420                1440                 1460
          .                   .                    .
TGCATAAGCTGGGTGTATGGGGCGGACCGTTTCTATGACAACATTGAGGACATGATTGGC
 C  I  S  W  V  Y  G  A  D  R  F  Y  D  N  I  E  D  M  I  G 1480                1500                 1520
          .                   .                    .
TACCGGCCATGGCCCCTGGTGAAGATCTCCTGGCTCTTCCTGACCCCTGGACTTTGCCTG
 Y  R  P  W  P  L  V  K  I  S  W  L  F  L  T  P  G  L  C  L 1540                1560                 1580
          .                   .                    .
GCCACTTTCCTCTTCTCCTTGAGCAAGTACACCCCCCTCAAGTACAACAACGTCTATGTG
 A  T  F  L  F  S  L  S  K  Y  T  P  L  K  Y  N  N  V  Y  V 1600                1620                 1640
          .                   .                    .
TACCCGCCCTGGGGATACTCCATTGGCTGGTTCCTGGCTCTGTCCTCCATGGTCTGTGTC
 Y  P  P  W  G  Y  S  I  G  W  F  L  A  L  S  S  M  V  C  V 1660                1680                 1700
```

FIGURE 1D

```
CCACTCTTCGTCGTCATCACCCTCCTGAAGACTCGGGGTCCTTTCAGGAAGCGTCTGCGT
 P  L  F  V  V  I  T  L  L  K  T  R  G  P  F  R  K  R  L  R
         1720                1740                1760

CAGCTCATCACCCCTGACTCCAGTCTGCCACAGCCCAAGCAACATCCCTGCTTGGATGGC
 Q  L  I  T  P  D  S  S  L  P  Q  P  K  Q  H  P  C  L  D  G
         1780                1800                1820

AGTGCTGGCCGGAACTTTGGGCCCTCCCCAACAAGGGAAGGACTGATAGCCGGGGAGAAG
 S  A  G  R  N  F  G  P  S  P  T  R  E  G  L  I  A  G  E  K
         1840                1860                1880

GAGACCCATTTGTAGGGTGTGACCAGAGGCCAGGCGGCTCCTAAGCCGGGAACCTAGGTC
 E  T  H  L
         1900                1920                1940

AGGGCCACCCTCCATTCTCAGCGGACAGCCTCTGCCTCTGTCTCCTGCCACAATCCTGCT
         1960                1980                2000

GGGAACCTCTGGAGAGCCACAGGCACCCCAGCTGGAGGCCAGACTCCTCTCTTGTG
```

FIGURE 2A

```
hBGT-1                              M D G K V A Q E Y G P P A V S
dBGT-1                              M D R K V A V P E D G P P V S
mBGT-1                              M D R K V A V H E D G Y P V S
rGAT-2                              M D N R V S G T T S N G E T K P
rGAT-3  M T A E Q A L P L G N G K A A E E A R G S E A L G 41
                                                              41
                                                              41
                                                              37
                                                              50
hBGT-1  W V P E E K L D Q E D D Q V K D R G Q W T N
dBGT-1  W L P E E K L D Q E D D Q V K D R G Q W T N
mBGT-1  W V P E E K M M D E G K D D Q V K D R G Q W T N
rGAT-2  V C P · V M E K V E E D G T L E R E Q W T N
rGAT-3  G G G · · A A G T R E A R D K A V H E R G H W N 91
                                                              91
                                                              91
                                                              87
                                                             100
hBGT-1  K M E F V L S V A G E I I G L G N V W R F P Y L C
dBGT-1  K M E F V L S V A G E I I G L G N V W R F P Y L C
mBGT-1  K M E F V L S V A G E I I G L G N V W R F P Y L C
rGAT-2  K M E F V L S V A G E I I G L G N V W R F P Y L C
rGAT-3  K V E F V L S V A G E I I G L G N V W R F P Y L C
          I hBGT-1  Y K N G G G A F F I P Y F I F F F T C G I P V F F
dBGT-1  Y K N G G G A F F I P Y F I F F F T C G I P V F F
mBGT-1  Y K N G G G A F F I P Y F I F F F S C G I P V F F
rGAT-2  Y K N G G G A F L I P Y L I F L F T C G I P V F F
rGAT-3  Y K N G G G A F L I P Y V V F L I C C G I P V F F
          II
```

FIGURE 2B

```
          ┌
hBGT-1     L E V A L G Q Y T S Q G S V T A W R K I C P L F Q   141
dBGT-1     L E V A L G Q Y T S Q G S V T A W R K I C P L F Q   141
mBGT-1     L E V A L G Q Y T S Q G S V T A W R K I C P L L Q   141
rGAT-2     L E T A L G Q Y T   E G G I T A W R K I C P I F E   137
rGAT-3     E T A L G Q F T S N Q G G I T C W R R V C P F F E   150

III
          ┌─────────────────────────────────────────────┐
hBGT-1     G I G L A S V V I E S Y L N Y Y H I H L A W A L L   190
dBGT-1     G I G L A S V V I E S Y L N Y Y H I H L A W A L L   190
mBGT-1     G I G M A S V V I E S Y L L V S L L H Y Y V H L A W A L L   190
rGAT-2     G I G Y A S Q M I V E A H L N Y Y I H L A W A I     185
rGAT-3     G                                                  200 hBGT-1     F Y L F S S F T S S E L P W T T C N N F W N T E H C
dBGT-1     F Y L F S S F T S S E L P W T T C N N F W N T E H C
mBGT-1     F Y L F S S F T S S E L P W T T C T N S H E W N T E H C
rGAT-2     F Y L F S S F T T D L P W G S C H E W N T E N C
rGAT-3     F Y L S N C F T T E L P W A T C G H E K C hBGT-1     T D F L N H S . . G A G T V T P F E N F T S P V M E
dBGT-1     M D F L N H S . . G A G T V T P F E N F T S P V M E
mBGT-1     V D F L N H S . . G A R T A T S S E N F T S P V M E
rGAT-2     V E F Q K T N . S A R G V S S E N A T S P V I E
rGAT-3     V E F Q K L N F S N Y S H V S . L Q N A T S P V M E
```

FIGURE 2C

```
                                                              240
                                                              240
                                                              240
                                                              235
                                                              250
hBGT-1  F W E R R V L G I T S G I H D L G S L R W E L A L
dBGT-1  F W E R R V L G I T S G I H D L G A L R W E L A L
mBGT-1  F W E R R V L G I T S G I H D L G S L R W E L A L
rGAT-2  F W E R R V L K I H D G H Q H E L V L
rGAT-3  F W E R R V L A I D G I E H I G N L R W E L A L
                    IV
hBGT-1  C L L A W V I C Y F C I W K G V K S T G K V Y
dBGT-1  C L L A W M L I C Y F C C H W K G V K S T T G K V Y
mBGT-1  C L L A W V I C Y F C I W K G V K S T G K V Y
rGAT-2  C L L A W I H I C Y F C H W K G T G K V Y
rGAT-3  C L T A V T L I C Y F C I W K G T S T G K V Y
                    V
                                                              290
                                                              290
                                                              290
                                                              285
                                                              300
hBGT-1  F T A T F P P Y L M L V L L I R G V T L P G A Y Q
dBGT-1  F T A T F P P Y L M L V L L I R G I T L P G A Y Q
mBGT-1  F T A T F P P Y L M L V L L I R G V T L P G A Y Q
rGAT-2  F T A T F P P Y I M L L L L I R G V T L P G A A Q
rGAT-3  F V A T F P P V M L L L L I R G V T L P G A S E hBGT-1  G I H Y L K P D L F R L K D P Q P V W M D A G T Q
dBGT-1  G I H Y Y L K P D L L R L K D D P Q V W M D A G T Q
mBGT-1  G I V F L Y K P D L T R L W D P Q V W M D A G T Q
rGAT-2  G I H V Q K P N I T R L H D P P Q V W M D A G T Q
rGAT-3  G I K F Y I Q K F Y P D L S R L S D P Q V W V D A G T Q
```

FIGURE 2D

```
           ┌─────── VI ───────┐
hBGT-1   I F F S F A I C Q C L T A L G S Y N K Y H N C
dBGT-1   I F F S F A I C Q C L T A L G S Y N K Y H N C
mBGT-1   I F F S F A I C Q C L T A L G S Y N K Y H N C
rGAT-2   I F F S F A I C L C L T A L G S Y N K Y H N C
rGAT-3   I F F S Y - - - - L L T A L G S Y N N Y N N C

┌─────── VII ───────┐
hBGT-1   Y K D C I A L C F L N S A T S F V A G F V V F S I    340
dBGT-1   Y R D S H A L C F L N S A T S F A A G F V V F S I    340
mBGT-1   Y R D R A A L C F L N S A T S F V A G F V V F S I    340
rGAT-2   Y R D C V A L C F I N S S T S F V A G F A I F S I    335
rGAT-3   Y R D C I M L C L N G T S G T S F A G E A I F S V    350 hBGT-1   L G F M S Q E Q G V P I S E V A E S G P G L A F I
dBGT-1   L G F M A Q E Q G L P I S S V A E S G P G L A F I
mBGT-1   L G F M S Q E Q G H P I S S V A E S G P G L A F I
rGAT-2   L G F M S Q E Q G V P I A E V A E S G P G L A F I
rGAT-3   L G F M A Y E Q G V P I A E V A E A G P G L A F I

┌─────── VIII ───────┐
hBGT-1   A F P K A V T M M P L S Q L W S C L F F I M L I F    390
dBGT-1   A F P K A V T M M P L S Q L W S C L F F I L L I F    390
mBGT-1   A F P K A V T M M P L S Q L W S C L F F I L L I F    390
rGAT-2   A Y P R A V M L P F S P A C F F H F M V L V L F      385
rGAT-3   A Y P K A V T M M P L S P W A T L F F M M L I F      400
```

FIGURE 2E

```
         ┌                                           ┐
hBGT-1   │ L G L D S Q F V C V E C L V T A S I D M F P R Q L
dBGT-1   │ L G L D S Q F V C V E C L V T A S M D M F P S Q L
mBGT-1   │ L G L D S Q F V C M E C L V T A S D D M F P Q Q L
rGAT-2   │ L G L D S Q F V C V E S L V T A L V D M Y P R V F
rGAT-3   │ L G L D S Q F V C V D S L V T A V V D M Y P K V F
         └                                           ┘

IX
                                            ┌──────────────────────────
hBGT-1     R K S G R R E L L L T I A V M C Y L H G I F L V       440
dBGT-1     R K S G R R E L L L A A V F C L V G L F L V           440
mBGT-1     R K S G R R D L L V H I A I S V L C Y M F I G L I M   440
rGAT-2     R K K N R R E L H L A I V V C Y F F I G G L V M       435
rGAT-3     R R G Y R R E L H L A L S I V S Y F L G L V M L       450

┌─────────────────────────────────────────────
hBGT-1     T E G G M Y I F Q L F D Y Y A A S G I C L L F L S
dBGT-1     T E G G M Y I F Q L F D Y Y A A S G I C L L F L A
mBGT-1     T E G G M Y I F Q L V F D Y Y A A S G M C L L F L S
rGAT-2     T E G G M Y I F Q L F D S Y A A S G M C L L F V A
rGAT-3     R G G M Y I F Q L F D S Y A A S G M C L L F V A 490
                                                                 490
                                                                 490
                                                                 485
                                                                 500 hBGT-1     L F E V V C I S W V Y G A D R F Y D N I E D M I I G
dBGT-1     M F E V V C I C H I S W V Y G A D R F Y D N I E D M I I G
mBGT-1     L F E V I C V A H V Y G A D R F Y D N I E D M I I G
rGAT-2     I F E S L C V H I G W V Y G A S R F Y D N V E D M I I G
rGAT-3     I F E C V C I G W Y Y G S N R F Y D N I E D M I I G
                                   X
              └──────────────────────────────────────────
```

FIGURE 2F

```
                                    XI
hBGT-1  Y R P W P L V K I S W L F L T P G L C L A T F L F
dBGT-1  Y R P W P L V K I S W L F L T P G L C L A T F L F
mBGT-1  Y R P W P L V K K Y C W L F F T P A V C L A T F L F
rGAT-2  Y K P W P I K L I K W C W K V V T P G I C A G I F F
rGAT-3  Y R P L S L I K W . . . . . . . . . . . . . . . . .

hBGT-1  S L S K Y T P L K Y N N V Y P P W G Y S I G W   540
dBGT-1  S L S Q Y T P L K Y N I Y Y P P W G Y S I G W   540
mBGT-1  S L S K Y T P L K Y N V M Y P S W G Y S I G W   540
rGAT-2  F L V K Y K P L R Y N V Y T P A W G D A L G W   535
rGAT-3  . . . . . . . . . . . . . . . G Y G I G W       550
                                              XII
hBGT-1  F L A L S S M V C V P L F V H I H T L L K T R G P F
dBGT-1  F L A L S S M I C V P L F V H I H T L L K T R G S F
mBGT-1  L L A F S S M A C V P L F I H T L L F I K T Q G S P L
rGAT-2  L L A L S S M L C I P L W I F I K L W K T E G T L
rGAT-3  L M A L S S M L C I P T W I F I K L W K T E G T L hBGT-1  R K R L R Q L I T P D S S L P Q Q K Q H P C L D   589
dBGT-1  K K R L R Q L I T P D P S L P Q Q R H L Y L D   589
mBGT-1  K R R L R Q L T T P D P S L P Q Q R P P Q . .   589
rGAT-2  R P L Q K L T V P C P A E D L P K M R G K L G A S P R  579
rGAT-3  P E K Q K L T V P S A D L . . . . . . . . . . .   600
```

FIGURE 2G

```
hBGT-1  GS.AG  RNFGPSPTREGLI  ...  AGEKETHL   614
dBGT-1  GGTS.  QDCGPSPTKEGLI  ...  VGEKETHL   614
mBGT-1  GS.SA  NCSSPAKQELI   ...  AWEKETHL   614
rGAT-2  .PELT  SPATPMTSLLR   ...  LTELESNC   602
rGAT-3  MVTV N DCEAKVKGDGTIS  AITEKETHF  627
```

FIGURE 4A
FIGURE 4B
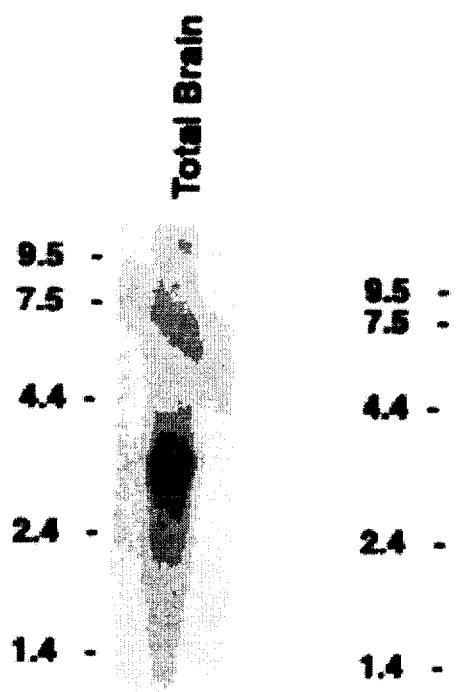
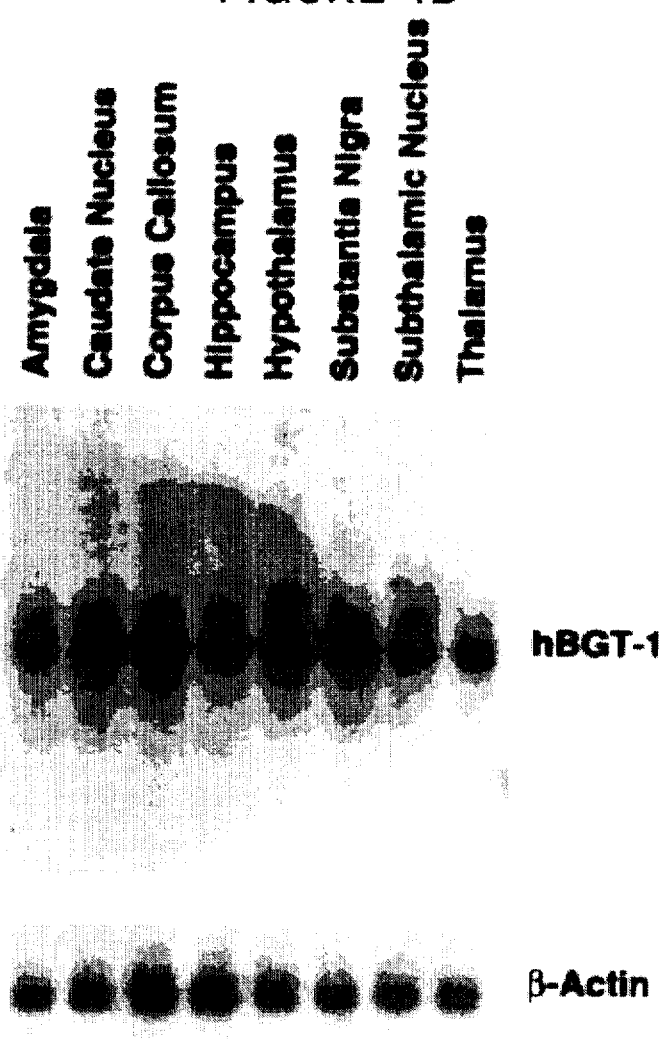

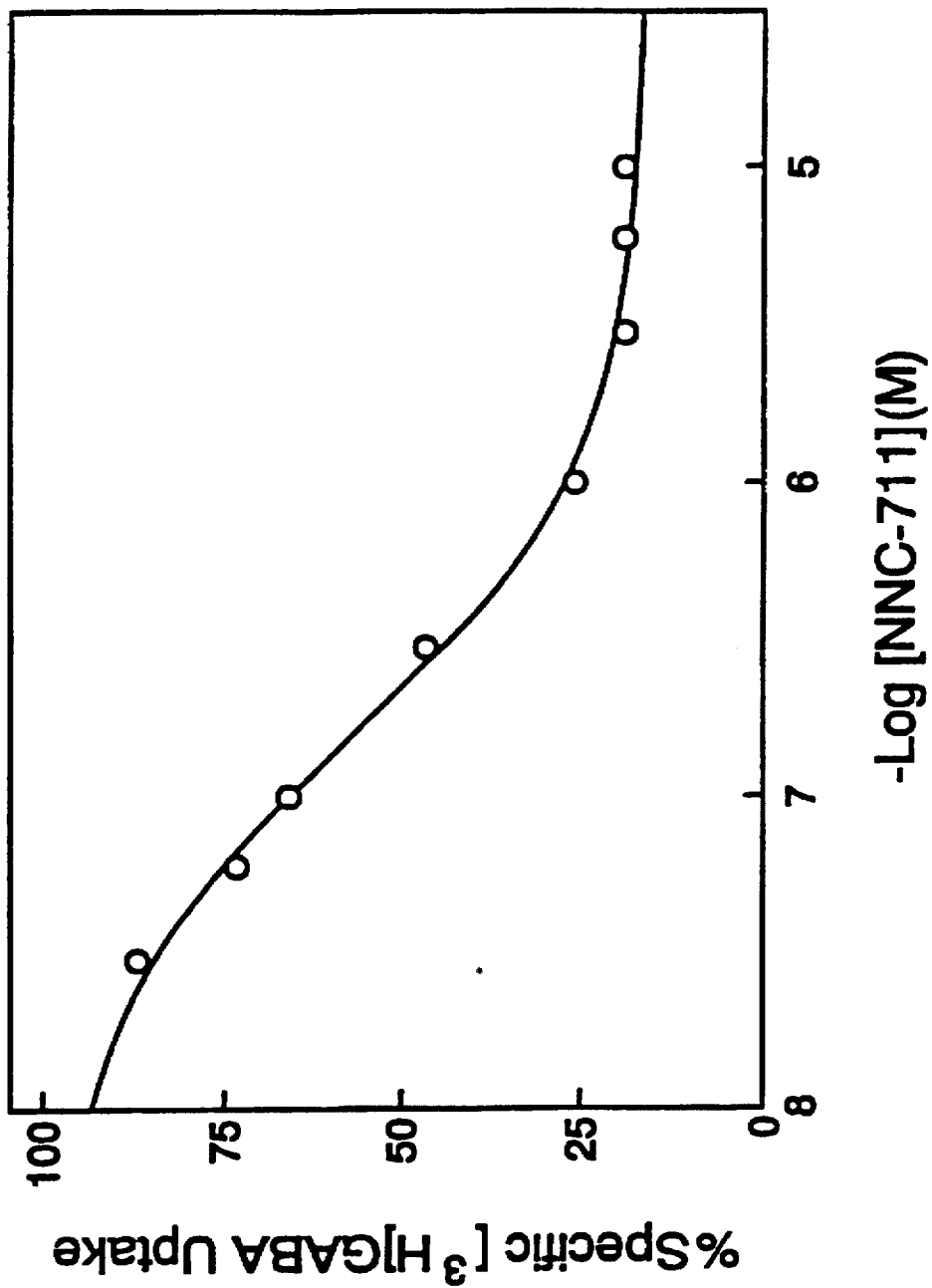

GAT-1

— 7.5
— 4.4
— 2.4
— 1.4

— 1B15

GAT-2

— 7.5
— 4.4
— 2.4
— 1.4

— 1B15

GAT-3

— 7.5
— 4.4
— 2.4
— 1.4

— 1B15

BGT-1

— 7.5
— 4.4
— 2.4
— 1.4

— 1B15

TAUT

— 7.5
— 4.4
— 2.4
— 1.4

— 1B15

FIGURE 12
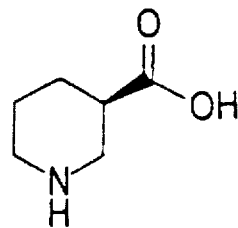
(R)-Nipecotic Acid
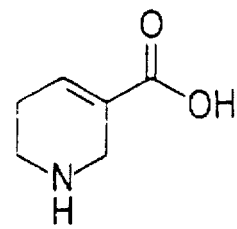
Guvacine
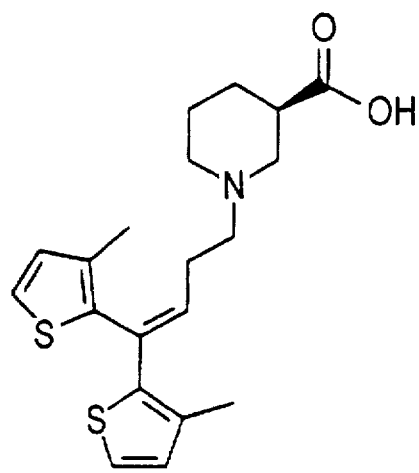
Tiagabine
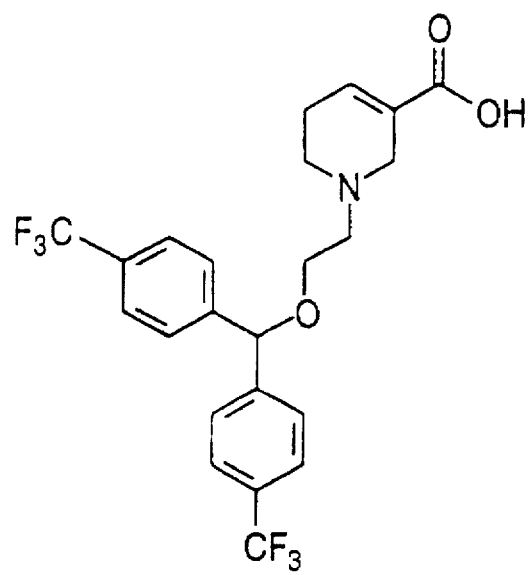
CI-966
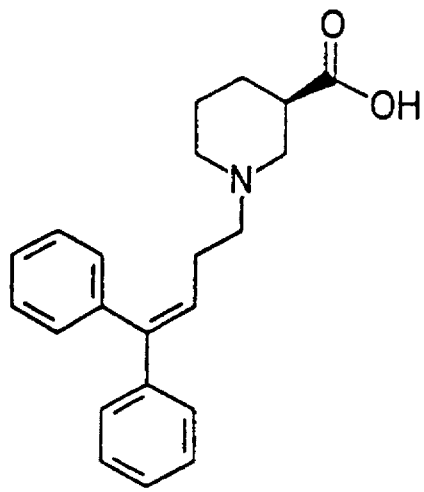
SKF-89976A
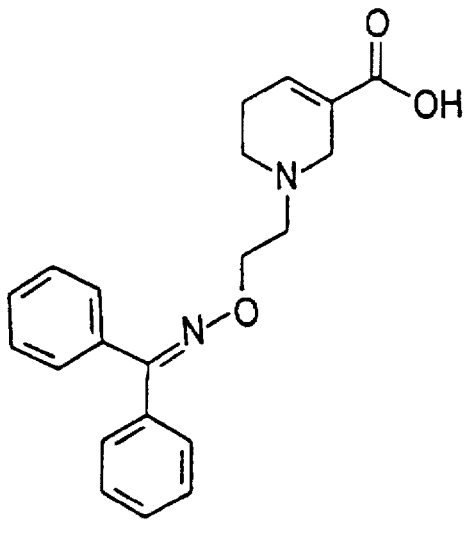
NNC-711

FIGURE 14

Rat Betaine/GABA Transporter

```
          10                      30                      50
           .                       .                       .
AGCTGTGGTATCCCAGTGTTCTTCCTGGAGGTGGCACTGGGTCAGTATAGCAGCCAGGGG
 S   C   G   I   P   V   F   F   L   E   V   A   L   G   Q   Y   S   Q   G 70                      90                     110
           .                       .                       .
AGTGTTACTGCTTGGAGGAAGATCTGTCCCCTTCTCCAAGGCATTGGCATGGCATCTGTG
 S   V   T   A   W   R   K   I   C   P   L   L   Q   G   I   G   M   A   S   V 130                     150                     170
           .                       .                       .
GTCATCGAGTCTTATTTGAACATCTACTACATCATCATCCTTGCCTGGGCTCTCTTCTAC
 V   I   E   S   Y   L   N   I   Y   Y   I   I   I   L   A   W   A   L   F   Y 190                     210                     230
           .                       .                       .
CTGTTCAGCTCCTTCACCTGGGAGCTTCCCTGGACAACCTGCACCAACTCCTGGAACACA
 L   F   S   S   F   T   W   E   L   P   W   T   T   C   T   N   S   W   N   T 250                     270                     290
           .                       .                       .
GAACATTGCGTGGACTTTCTGAACTACTCATCGACCAGAGCCGCAAGCTACTCTGAGAAC
 E   H   C   V   D   F   L   N   Y   S   S   T   R   A   A   S   Y   S   E   N 310                     330                     350
           .                       .                       .
TTCACCTCACCAGTCATGGAATTCTGGGAGAGACGGGTTTTGGGTATTACATCAGGCATC
 F   T   S   P   V   M   E   F   W   E   R   R   V   L   G   I   T   S   G   I 370                     390                     410
           .                       .                       .
CATGACCTGGGGTCCCTGCGCTGGGAGCTGGCCCTGTGCCTCCTGCTCGCCTGGATC
 H   D   L   G   S   L   R   W   E   L   A   L   C   L   L   L   A   W   I
```

METHODS FOR IDENTIFYING COMPOUNDS WHICH SPECIFICALLY BIND A HUMAN BETAINE/GABA TRANSPORTER

This application is a continuation-in-part of U.S. Ser. No. 08/001,738, filed Jan. 4, 1993 now abandoned.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Cell surface transporters are critical to the survival and proper functioning of cells. Transporters serve in virtually all cells as the conduit by which essential nutrients such as glucose and amino acids gain access to the cell interior (for review see Silverman, 1991; Christensen, 1984). Transporters also play a critical role in the ability of cells to adapt to alterations in osmolarity. Within the nervous system transporters additionally serve a more specialized function. Specifically, high-affinity transporters are responsible for removing neurotransmitters from the synaptic cleft, thereby terminating neurotransmission (for review, see Kanner and Schuldiner, 1987).

The application of molecular biological techniques to the study of neurotransmitter transporters has greatly advanced our understanding of this class of proteins. Clones have now been obtained for many of the major neurotransmitters including γ-aminobutyric acid (GABA) (Guastella et al., 1990; Nelson et al., 1990; Borden et al., 1992; Liu et al., 1992a), glycine (Smith et al., 1992a; Guastella et al., 1992; Liu et al., 1992b), norepinephrine (Pacholczyk et al., 1991), dopamine (Shimada et al., 1991; Usdin et al., 1991; Giros et al., 1992), and serotonin (Hoffman et al., 1991; Blakely et al., 1991).

Transporters have also been obtained for molecules with presumed neuromodulatory roles, such as taurine (Smith et al.,1992b; Uchida et al., 1992) and proline (Fremeau, Jr. et al., 1992). These transporters have in common a requirement for sodium and chloride, and they show considerable structural similarity including 12 putative transmembrane domains. More recently clones have been obtained that encode glutamate transporters (Storck et al., 1992; Pines et al., 1992; Kanai and Hediger, 1992). These transporters are structurally unrelated to the others, perhaps consistent with their different ionic requirements (for review, see Amara, 1992).

Cloning of GABA transporters has revealed considerable diversity of this system. In addition to the original GABA transporter clone obtained from rat brain (GAT-1; Guastella et al., 1990), we have identified two additional rat brain clones encoding high-affinity GABA transporters which we term GAT-2 and GAT-3 (Borden et al., 1992). A clone identical to GAT-3 was described by Clark et al. (1992) and referred to as GAT-B, and the mouse homologues of all three transporters have been described (Liu, et al. 1993), although a different nomenclature was employed. An additional and unanticipated member of this class is a betaine transporter, cloned from MDCK dog kidney cells by Handler and coworkers (Yamauchi et al., 1992). Betaine is an important osmolyte in the kidney, and possibly other organs. Interestingly, this transporter was found to have higher affinity for GABA than for betaine, suggesting a role in GABAergic transmission. However, transporter mRNA was not detected in dog brain (Yamauchi et al., 1992). Subsequently, Lopez-Corcuera et al. (1992) isolated from mouse brain a cDNA clone which displays both sequence and pharmacological similarity to the dog kidney clone. We now report the cloning and expression of a related clone from a human brain cDNA library. Although the function of this transporter in the nervous system is not understood, it may serve to regulate both GABAergic transmission and osmolarity.

To further characterize the human BGT-1 transporter, we have determined which of the cloned GABA transporters (e.g. GAT-1, GAT-2, GAT-3 and BGT are in neurons and which are in glia, we have undertaken a combined pharmacological and molecular biological study using cell cultures derived from rat brain. We have also determined the specificity of four lipophilic GABA transport inhibitors for the cloned GABA transporters.

SUMMARY OF THE INVENTION

This invention provides an isolated nucleic acid molecule encoding a mammalian betaine/GABA transporter. In one embodiment of this invention the isolated nucleic acid molecule encodes a human betaine/GABA transporter. In another embodiment of this invention, the nucleic acid molecule encoding the human betaine/GABA transporter comprises a plasmid designated pcEXV-hBGT (ATCC Accession No. 75393).

This invention provides a nucleic acid probe comprising a nucleic acid molecule of at least 15 nucleotides capable of specifically hybridizing with a unique sequence included within the sequence of a nucleic acid molecule encoding a mammalian betaine/GABA transporter. This invention also provides a nucleic acid probe comprising a nucleic acid molecule of at least 15 nucleotides capable of specifically hybridizing with a unique sequence included within the sequence of a nucleic acid molecule encoding a human betaine/GABA transporter.

This invention further provides an antisense oligonucleotide having a sequence capable of binding specifically to an mRNA molecule encoding a mammalian betaine/GABA transporter so as to prevent translation of the mRNA molecule. This invention also provides an antisense oligonucleotide having a sequence capable of binding specifically to an mRNA molecule encoding a human betaine/GABA transporter so as to prevent translation of the mRNA molecule.

This invention provides a monoclonal antibody directed to a mammalian betaine/GABA transporter. This invention further provides a monoclonal antibody directed to a human betaine/GABA transporter.

This invention provides a pharmaceutical composition comprising an amount of a substance effective to alleviate the abnormalities resulting from overexpression of a mammalian betaine/GABA transporter and a pharmaceutically acceptable carrier as well as a pharmaceutical composition comprising an amount of a substance effective to alleviate abnormalities resulting from underexpression of betaine/GABA transporter and a pharmaceutically acceptable carrier.

A pharmaceutical composition comprising an amount of a substance effective to alleviate the abnormalities resulting from overexpression of a human betaine/GABA transporter and a pharmaceutically acceptable carrier as well as a pharmaceutical composition comprising an amount of a substance effective to alleviate abnormalities resulting from underexpression of a human betaine/GABA transporter and a pharmaceutically acceptable carrier is also provided by this invention.

This invention also provides a transgenic, nonhuman mammal whose genome comprises DNA encoding a mammalian betaine/GABA transporter so positioned within such genome as to be transcribed into antisense mRNA complementary to mRNA encoding the betaine/GABA transporter and when hybridized to mRNA encoding the betaine/GABA transporter, the complementary mRNA reduces the translation of the mRNA encoding the betaine/GABA transporter.

This invention also provides a transgenic, nonhuman mammal whose genome comprises DNA encoding a human betaine/GABA transporter so positioned within such genome as to be transcribed into antisense mRNA which is complementary to mRNA encoding the human betaine/GABA transporter and when hybridized to mRNA encoding the human betaine/GABA transporter, the antisense mRNA thereby reduces the translation of mRNA encoding the human betaine/GABA transporter.

This invention also provides a transgenic, nonhuman mammal whose genome comprises DNA encoding a mammalian betaine/GABA transporter so positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a human betaine/GABA transporter so positioned within such genome as to be transcribed into antisense mRNA which is complementary to mRNA encoding the betaine/GABA transporter and when hybridized to mRNA encoding the betaine/GABA transporter, the antisense mRNA thereby prevents the translation of mRNA encoding the human betaine/GABA transporter.

This invention provides a method of screening drugs to identify drugs which specifically interact with, and bind to, a mammalian betaine/GABA transporter on the surface of a cell which comprises contacting a mammalian cell comprising an isolated DNA molecule encoding a mammalian betaine/GABA transporter, the protein encoded thereby is expressed on the cell surface, with a plurality of drugs, determining those drugs which bind to the mammalian cell, and thereby identifying drugs which specifically interact with, and bind to, a mammalian betaine/GABA transporter.

This invention provides a method of screening drugs to identify drugs which specifically interact with, and bind to, a human betaine/GABA transporter on the surface of a cell which comprises contacting a mammalian cell comprising an isolated DNA molecule encoding a human betaine/GABA transporter, the protein encoded thereby is expressed on the cell surface, with a plurality of drugs, determining those drugs which bind to the mammalian cell, and thereby identifying drugs which specifically interact with, and bind to, a human betaine/GABA transporter.

This invention also provides a method of determining the physiological effects of expressing varying levels of a mammalian betaine/GABA transporter which comprises producing a transgenic nonhuman animal whose levels of mammalian betaine/GABA transporter expression are varied by use of an inducible promoter which regulates mammalian betaine/GABA transporter expression.

This invention also provides a method of determining the physiological effects of expressing varying levels of a human betaine/GABA transporter which comprises producing a transgenic nonhuman animal whose levels of human betaine/GABA transporter expression are varied by use of an inducible promoter which regulates human betaine/GABA transporter expression.

This invention further provides a method of determining the physiological effects of expressing varying levels of a mammalian betaine/GABA transporter which comprises producing a panel of transgenic nonhuman animals each expressing a different amount of mammalian betaine/GABA transporter.

This invention further provides a method of determining the physiological effects of expressing varying levels of a human betaine/GABA transporter which comprises producing a panel of transgenic nonhuman animals each expressing a different amount of human betaine/GABA transporter.

This invention provides a method for diagnosing a predisposition to a disorder associated with the expression of a specific mammalian betaine/GABA transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a mammalian betaine/GABA transporter and labelled with a detectable marker; e.) detecting labelled bands which have hybridized to the DNA encoding a mammalian betaine/GABA transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for diagnosing a predisposition to a disorder associated with the expression of a specific human betaine/GABA transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a human betaine/GABA transporter and labelled with a detectable marker; e.) detecting labelled bands which have hybridized to the DNA encoding a human betaine/GABA transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for determining whether a substrate not known to be capable of binding to a mammalian betaine/GABA transporter can bind to the mammalian betaine/GABA transporter which comprises contacting a mammalian cell comprising an isolated DNA molecule encoding the betaine/GABA transporter with the substrate under conditions permitting binding of substrates known to bind to a transporter, detecting the presence of any of the substrate bound to the betaine/GABA transporter, and thereby determining whether the substrate binds to the betaine/GABA transporter.

This invention provides a method for determining whether a substrate not known to be capable of binding to a human betaine/GABA transporter can bind to a human betaine/GABA transporter which comprises contacting a mammalian cell comprising an isolated DNA molecule encoding the human betaine/GABA transporter with the substrate under conditions permitting binding of substrates known to bind to a transporter, detecting the presence of any of the substrate bound to the human betaine/GABA transporter, and thereby determining whether the substrate binds to the human betaine/GABA transporter.

BRIEF DESCRIPTION OF THE FIGURES

FIGS. 1A–1D. These four consecutive figures disclose the nucleotide sequence and deduced amino acid sequence of the human Betaine/GABA transporter. Nucleotides are presented in the 5' to 3' orientation and the coding region is numbered starting from the putative initiating methionine. DNA sequence was determined by the chain termination method of Sanger (1977) on denatured double-stranded plasmid templates using Sequenase. Deduced amino acid sequence (single letter abbreviation) by translation of a long open reading frame is shown.

FIGS. 2A–2G. Sequence alignment of human BGT-1 with other GABA transporters. Residues identical to hBGT-1 are shaded, and the 12 putative α-helical membrane-spanning domains (I-XII) are bracketed. BGT-1 is the dog betaine/GABA transporter (SEQ ID No. 8) (Yamauchi et al., 1992); mGAT-2 (SEQ ID No. 7) is the mouse homologue of rat GAT-2, originally referred to as GAT3 (Liu et al., 1993); rGAT-2 (SEQ ID No. 9) and rGAT-3 (SEQ ID No. 10) are rat GAT-2 and rat GAT-3, respectively (Borden et al, 1992).

FIG. 4A. Northern blot analysis of hBGT-1 mRNA. Total RNA from human brain (25 µg) was separated by agarose/formaldehyde gel electrophoresis, blotted, and hybridized with a ³²P-labeled fragment of the hBGT-1 cDNA. The autoradiogram was developed after 10 days and revealed a single approximately 3.1 Kb transcript.

FIG. 4B. Northern blot analysis of hBGT-1 mRNA. A Northern blot containing poly A⁺ RNA (≈2 µg) from various human brain regions was hybridized with ³²P-labeled hBGT-1 probe as described in FIG. 4A, and developed after an overnight exposure. The blot was subsequently reprobed for p-actin (β2.0 kb transcript, 20 minute exposure).

FIG. 9. NNC-711 inhibition of GABA transport in brain aggregates. Rat brain aggregates were incubated with [³H] GABA and the indicated concentrations of NNC-711, as described in Methods. Data show specific uptake, expressed as percent of uptake in the absence of inhibitor. Data are from a single experiment that was repeated three times with similar results.

FIG. 10A: Northern blot analysis of GAT-1 mRNA (≈4.2 Kb), FIG. 10B: Northern blot analysis of GAT-2 mRNA (≈2.4 Kb), FIG. 10C: Northern blot analysis of GAT-3 mRNA (≈4.7 Kb), FIG. 10D: Northern blot analysis of rBGT-1 mRNA (≈2.4 Kb), and FIG. 10E: Northern blot analysis of TAUT mRNA (≈6.2 Kb). Total RNA from neuronal (lane 1), Type 1 astrocyte (lane 2), and O-2A/Type 2 astrocyte (lane 3) cultures, was separated by formaldehyde/agarose gel electrophoresis, blotted, and hybridized at high stringency with ³²P-labeled transporter cDNAs (see Methods). The autoradiograms were developed after 5 days, with the exception of TAUT (overnight). Corresponding autoradiograms representing cyclophilin (1B15) hybridization are shown at right (45 minute exposure). Identical samples of neurons, Type 1 astrocytes, and O-2A/Type 2 astrocytes were used for each of five blots shown. Note that the levels of rBGT-1 mRNA in astrocytes in the experiment shown are lower than average (see Table 8 for quantitation).

FIG. 12. Structure of lipophilic GABA transport inhibitors and their parent compounds.

FIG. 14. Nucleotide Sequence and Deduced Amino Acid Sequence of the Rat Betaine/GABA Transporter. A DNA fragment representing rBGT-1 was amplified from rat brain cDNA using PCR and subcloned into pUC18. DNA sequence was determined by the chain termination method of Sanger (1977) on denatured double-stranded plasmid templates using Sequenase. Nucleotides are presented in the 5' to 3' orientation (SEQ ID No. 5); deduced amino acid sequence (single letter abbreviation) by translation of a long open reading frame is shown (SEQ ID No. 6). The region of rBGT-1 encoded by the fragment corresponds to amino acids 84–139 of the human Betaine/GABA transporter.

DETAILED DESCRIPTION OF THE INVENTION

Figure 3:
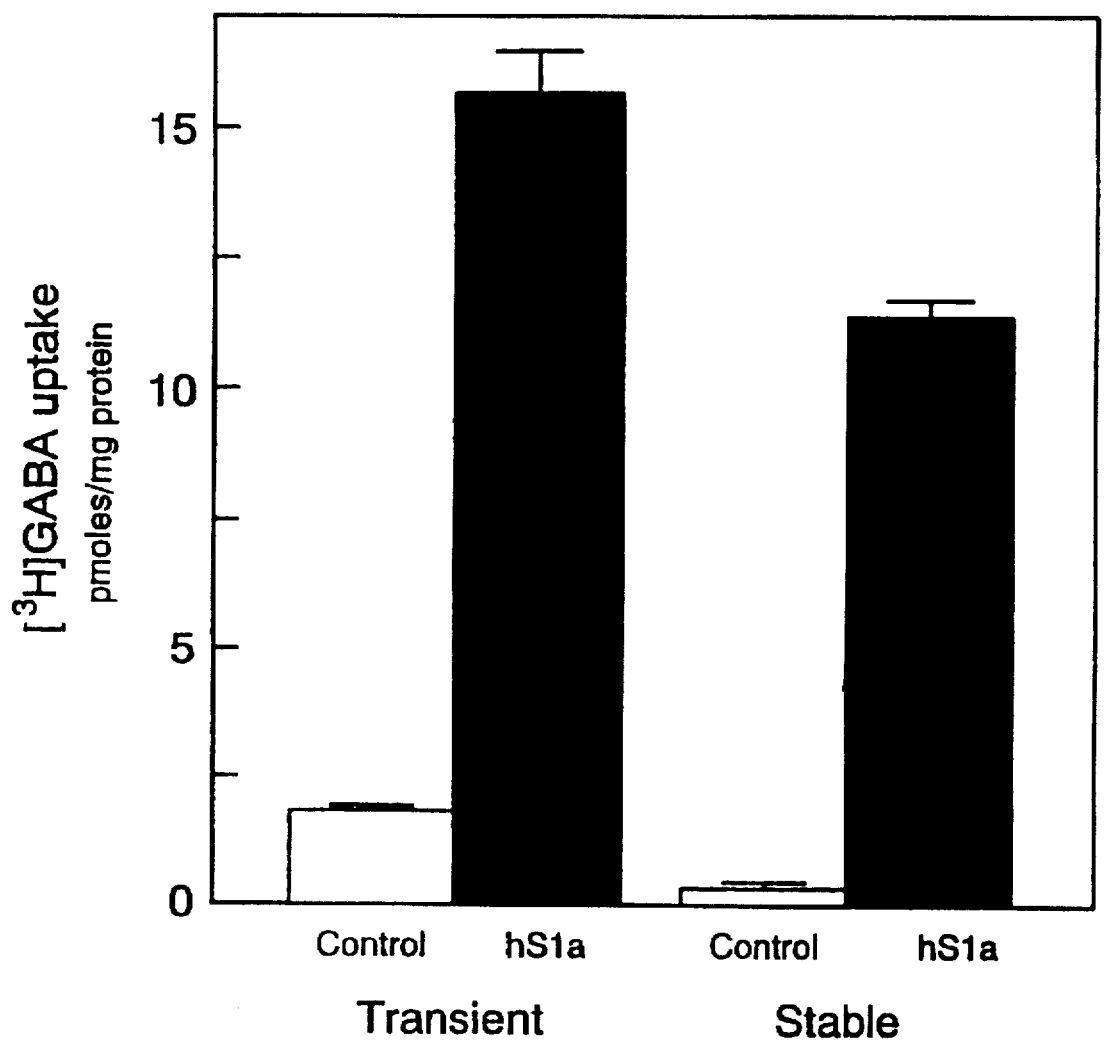
FIG. 3. GABA transport following transient and stable transfection of hS1a. Data show specific GABA uptake following transient (COS cells) and stable transfection (LM (tk⁻); clone 3) with human hS1a; control represents non-transfected cells. Transfections were performed as described in Methods. Cells were incubated for 10 minutes (37° C.) with 50 nM [³H]GABA, washed, and radioactivity determined. Data show specific uptake (mean±SD), expressed as cpm per mg cellular protein, and are from a representative experiment that was repeated many times with similar results.

This invention provides an isolated nucleic acid molecule encoding a mammalian betaine/GABA transporter. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian betaine/GABA transporter. As used herein, "betaine/GABA transporter" means a molecule which, under physiologic conditions, is substantially specific for the neurotransmitter GABA and betaine, is saturable and of high affinity for GABA and betaine. One embodiment of this invention is an isolated human nucleic acid molecule encoding a mammalian betaine/GABA transporter. Another embodiment of this invention is an isolated rat nucleic acid molecule encoding a mammalian betaine/GABA transporter. A preferred embodiment of this invention is an isolated nucleic acid molecule encoding a human betaine/GABA transporter. Such molecules may have coding sequences substantially the same as the coding sequences shown in FIGS. 1A–1D (SEQ ID NO. 1) or FIG. 14 (SEQ ID NO. 5). The DNA molecule of FIGS. 1A–1D (Sequence I.D. No. 1) encodes the sequence of a human betaine/GABA transporter gene. The DNA molecule of FIG. 14 (SEQ ID No. 5) partially encodes a rat betaine/GABA transporter gene. One means of isolating a mammalian betaine/GABA transporter is to probe a mammalian genomic library with a natural or artificially designed DNA probe, using methods well known in the art. In the preferred embodiment of this invention, the mammalian betaine/GABA transporter is a human protein and the nucleic acid molecules encoding them are isolated from a human cDNA library or a human genomic DNA library. Degenerate oligonucleotide primers the sequences of which are derived from comparisons between conserved regions of several transporters are useful for identifying a nucleic acid molecule encoding a mammalian betaine/GABA transporter, obtaining a probe to a mammalian betaine/GABA transporter and for isolating a nucleic acid molecule encoding a mammalian betaine/GABA transporter. DNA and cDNA molecules which encode a human or mammalian betaine/GABA transporter are used to obtain complementary genomic DNA, cDNA or RNA from human, mammalian or other animal sources, or to isolate related cDNA or genomic clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

A sequence derived from the DNA encoding a human or a mammalian betaine/GABA transporter such as that derived from the sequence encoding the human betaine/GABA transporter in FIGS. 1A–1D (SEQ ID NO. 1) can be used to identify and isolate human or a mammalian RNA or DNA encoding a betaine/GABA transporter subtype or a related transporter. Transporter subtypes may be products of the same gene or more than one gene. Products of the same gene are generated by alternative splicing of the RNA encoding the transporter, by rearrangements of the same gene encoding the transporter or by other means.

This invention provides an isolated nucleic acid molecule which has been so mutated as to be incapable of encoding a molecule having normal transporter activity, and not expressing native transporter. An example of a mutated nucleic acid molecule provided by this invention is an isolated nucleic acid molecule which has an in-frame stop codon inserted into the coding sequence such that the transcribed RNA is not translated into a protein having normal transporter activity.

This invention provides a cDNA molecule encoding a mammalian betaine/GABA transporter. This invention further provides a cDNA molecule encoding a human betaine/GABA transporter. The cDNA encoding the mammalian or human betaineGABA transporter has coding sequence substantially the same as the coding sequence shown in FIGS. 1A–1D. (Sequence I.D. No. 1). These molecules and their equivalents are obtained by the means described above.

This invention also provides an isolated protein which is a mammalian GABA transporter. One embodiment of this invention is a rat GABA transporter protein having the partial rat GABA transporter protein having an amino acid sequence substantially the same as the sequence shown in FIG. 14 (Sequence I.D. No. 5) In a preferred embodiment of this invention, the protein is a human GABA transporter protein having an amino acid sequence substantially the same as the sequence shown in FIGS. 1A–1D (Sequence I.D. Nos. 1 and 2). As used herein, the term "isolated protein" is intended to encompass a protein molecule free of other cellular components. One means for obtaining an isolated betaine/GABA transporter is to express DNA encoding the transporter in a suitable host, such as a bacterial (e.g. *E. coli*), yeast (e.g. *S. cerevisia*), insect, or mammalian cell, using methods well known to those skilled in the art, and recovering the transporter protein after it has been expressed in such a host, again using methods well known in the art. The transporter may also be isolated from cells which express it, in particular from cells which have been transfected with the expression vectors described below in more detail.

This invention also provides a vector comprising an isolated nucleic acid molecule such as DNA, RNA, or cDNA, encoding a mammalian betaine/GABA transporter. This invention also provides a vector comprising an isolated nucleic acid molecule such as DNA, RNA, or cDNA, encoding a human betaine/GABA transporter.

Examples of vectors are viruses such as retroviruses, baculovirus, bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as the coding sequence shown in FIGS. 1A-1D (Seq. I.D. No. 1) and designated pcEXV-hBGT (ATCC Accession No. 75393 deposited Dec. 30, 1992). Another examples of such plasmids are plasmids comprising cDNA having a partial coding sequence substantially the same as the coding sequence shown in FIG. 14 (Seq. I.D. No. 5) and designated pUC18-rBGT-1 (ATCC Accession No. ). Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides expression vectors comprising a DNA molecule encoding a mammalian betaine/GABA transporter adapted for expression in a bacterial cell, a yeast cell, insect, or a mammalian cell which additionally comprise the regulatory elements necessary for expression of the DNA in the bacterial, yeast, insect or mammalian cells operatively linked to the DNA encoding a mammalian betaine/GABA transporter or to the DNA encoding a human betaine/GABA transporter as to permit expression thereof. DNA having coding sequences substantially the same as the coding sequence shown in FIGS. 1A-1D may usefully be inserted into the vectors to express mammalian or human betaine/GABA transporters. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the transporter. Certain uses for such cells are described in more detail below.

In one embodiment of this invention a plasmid is adapted for expression in a bacterial, yeast, insect, or, in particular, a mammalian cell wherein the plasmid comprises a DNA molecule encoding a mammalian betaine/GABA transporter and the regulatory elements necessary for expression of the DNA in the bacterial, yeast, insect, or mammalian cell operatively linked to the DNA encoding a mammalian betaine/GABA transporter as to permit expression thereof.

In another embodiment of this invention a plasmid is adapted for expression in a bacterial, yeast, insect, or, in particular, a mammalian cell wherein the plasmid comprises a DNA molecule encoding a human betaine/GABA transporter and the regulatory elements necessary for expression of the DNA in the bacterial, yeast, insect, or mammalian cell operatively linked to the DNA encoding a human betaine/GABA transporter to permit expression thereof. Suitable plasmids may include, but are not limited to plasmids adapted for expression in a mammalian cell, e.g., EVJB or EXV. Examples of such plasmids adapted for expression in a mammalian cell are plasmids comprising cDNA having coding sequences substantially the same as the coding sequence shown in FIGS. 1A-1D (SEQ ID NO. 1) and the regulatory elements necessary for expression of the DNA in the mammalian cell. A plasmid adapted for expression in a mammalian cell comprising the DNA encoding a human betaine/GABA transporter has been designated pcEXV-hBGT and deposited under ATCC Accession No. 75393. A plasmid adapted for expression in a mammalian cell comprising the DNA partially encoding a rat betaine/GABA transporter has been designated pUC18-rBGT-1 and deposited under ATCC Accession No. Those skilled in the art will readily appreciate that numerous plasmids adapted for expression in a mammalian cell which comprise DNA encoding a mammalian or human betaine/GABA transporter and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md., 20852.

This invention provides a mammalian cell comprising a DNA molecule encoding a mammalian betaine/GABA transporter, such as a mammalian cell comprising a plasmid adapted for expression in a mammalian cell, which comprises a DNA molecule encoding a mammalian betaine/GABA transporter and the regulatory elements necessary for expression of the DNA in the mammalian cell operatively linked to the DNA encoding a mammalian transporter as to permit expression thereof. This invention also provides a mammalian cell comprising a DNA molecule encoding a human betaine/GABA transporter, such as a mammalian cell comprising a plasmid adapted for expression in a mammalian cell, which comprises a DNA molecule encoding a human betaine/GABA transporter and the regulatory elements necessary for expression of the DNA in the mammalian cell operatively linked to the DNA encoding a human transporter as to permit expression thereof. Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, or DNA encoding these transporters may be otherwise introduced into mammalian cells, e.g., by microinjection, to obtain mammalian cells which comprise DNA, e.g., CDNA or a plasmid, encoding a mammalian or a human betaine/GABA transporter Cell line L-BGT was deposited with the ATCC on Dec. 3, 1992 and was accorded ATCC Accession No. CRL-11229.

This invention provides a nucleic acid probe comprising a nucleic acid molecule of at least 15 nucleotides capable of specifically hybridizing with a unique sequence included within the sequence of a nucleic acid molecule encoding a mammalian betaine/GABA transporter. This invention also provides a nucleic acid probe comprising a nucleic acid molecule of at least 15 nucleotides capable of specifically hybridizing with a unique sequence included within the sequence of a nucleic acid molecule encoding a human betaine/GABA transporter, for example with a coding sequence included within the sequence shown in FIGS. 1A–1D (SEQ ID NO. 1). As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a mammalian betaine/GABA transporter or human betaine/GABA transporter is useful as a diagnostic test for any disease process in which levels of expression of the corresponding betaine/GABA are altered. DNA probe molecules are produced by insertion of a DNA molecule which encodes the mammalian or human betaine/GABA transporter or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1D (SEQ ID NO. 1). The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian betaine/GABA transporter or complementary to the sequence of a DNA molecule which encodes a human betaine/GABA transporter, are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a mammalian betaine/GABA transporter on the surface of a cell by detecting the presence of mRNA coding for the mammalian betaine/GABA transporter. This invention further provides a method of detecting the expression of a human betaine/GABA transporter on the surface of the cell by detecting the presence of mRNA coding for the corresponding betaine/GABA transporter. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis et al. 1982). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a mammalian betaine GABA transporter so as to prevent translation of the mammalian betaine/GABA transporter. This invention provides an antisense oligonucleotide having a sequence capable of binding specifically with any sequences of an mRNA molecule which encodes a human betaine/GABA transporter so as to prevent translation of the human betaine/GABA transporter. As used herein, the phrase "binding specifically" means the ability of an antisense oligonucleotide to recognize a nucleic acid sequence complementary to its own and to form double-helical segments through hydrogen bonding between complementary base pairs. The antisense oligonucleotide may have a sequence capable of binding specifically with any sequences of the cDNA molecules whose sequences are shown in FIGS. 1A–1D (SEQ ID NO. 1). A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a mammalian betaine/GABA transporter by passing through a cell membrane and binding specifically with mRNA encoding a mammalian betaine/GABA transporter in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human betaine/GABA transporter by passing through a cell membrane and binding specifically with mRNA encoding a human betaine/GABA transporter in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences substantially the same as the coding sequence shown in FIGS. 1A–1D (SEQ ID NO. 1) may be used as the oligonucleotides of the pharmaceutical composition.

This invention also provides a method of treating abnormalities which are alleviated by reduction of expression of a betaine/GABA transporter. This method comprises administering to a subject an effective amount of the pharmaceutical composition described above effective to reduce expression of the betaine/GABA transporter by the subject. This invention further provides a method of treating an abnormal condition related to betaine/GABA transporter activity which comprises administering to a subject an amount of the pharmaceutical composition described above effective to reduce expression of the betaine/GABA transporter by the subject. Examples of such abnormal conditions are epilepsy, migraine, ischemia, myoclonus, spasticity, and chronic pain.

Antisense oligonucleotide drugs inhibit translation of mRNA encoding these transporters. Synthetic antisense oligonucleotides, or other antisense chemical structures are designed to bind to mRNA encoding a betaine/GABA transporter and are useful as drugs to inhibit expression of betaine/GABA transporter genes in patients. This invention provides a means to therapeutically alter levels of expression of a mammalian betaine/GABA transporters by the use of a synthetic antisense oligonucleotide drug (SAOD) which inhibits translation of mRNA encoding these transporters. Synthetic antisense oligonucleotides, or other antisense chemical structures designed to recognize and selectively bind to mRNA, are constructed to be complementary to portions of the nucleotide sequence shown in FIGS. 1A–1D (SEQ ID NO. 1) of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequence shown in FIGS. 1A–1D (SEQ ID NO. 1) by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen, J. S., 1989; Weintraub, H. M., 1990). In addition, coupling of ribozymes to antisense oligonucleotides is a promising strategy for inactivating target mRNA (N. Sarver et al. 1990). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce transporter expression in particular target cells of a patient, in any clinical condition which may benefit from reduced expression of GABA or taurine transporters.

This invention provides an antibody directed to the mammalian betaine/GABA transporter. This antibody may comprise, for example, a monoclonal antibody directed to an epitope of a mammalian betaine/GABA transporter present on the surface of a cell, the epitope having an amino acid sequence substantially the same as the amino acid sequence for a cell surface epitope of the human betaine/GABA transporter included in the amino acid sequence shown in FIGS. 1A–1D (SEQ ID NOs. 1 and 3). This invention provides an antibody directed to a human betaine/GABA transporter. This antibody may comprise, for example, a monoclonal antibody directed to an epitope of a human betaine/GABA transporter present on the surface of a cell, the epitope having an amino acid sequence substantially the same as an amino acid sequence for a cell surface epitope of the human betaine/GABA transporter included in the amino acid sequence shown in FIGS. 1A–1D (SEQ ID NOs. 1 and 3). Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore, antibodies directed to hydrophilic amino acid sequences specific to a human transporter will bind to a surface epitope of a human taurine transporter and antibodies directed to the conserved hydrophilic amino acid sequences shown in FIGS. 1A–1D (SEQ ID NOs. 1 and 3) will bind to a surface epitope of a mammalian betaine/GABA transporter. Antibodies directed to mammalian or human transporters may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequences shown in FIGS. 1A–1D (SEQ ID NOs 1 and 2). As a still further alternative, DNA, such as a cDNA or a fragment thereof, may be cloned and expressed and the resulting polypeptide recovered and used as an immunogen. These antibodies are useful to detect the presence of mammalian transporters encoded by the isolated DNA, or to inhibit the function of the transporters in living animals, in humans, or in biological tissues or fluids isolated from animals or humans.

This invention also provides a pharmaceutical composition which comprises an effective amount of an antibody directed to an epitope of the mammalian transporter, effective to block binding of naturally occurring substrates to the transporter, and a pharmaceutically acceptable carrier. A monoclonal antibody directed to a comserved epitope of a human betaine/GABA transporter present on the surface of a cell which has an amino acid sequence substantially the same as an amino acid sequence for a cell surface epitope of the human betaine/GABA transporter included in the amino acid sequences shown in FIGS. 1A–1D (SEQ ID NOs. 1 and 3) is useful for this purpose.

This invention also provides a pharmaceutical composition which comprises an effective amount of an antibody directed to an epitope of the human betaine/GABA transporter, effective to block binding of naturally occurring substrates to the human betaine/GABA transporter, and a pharmaceutically acceptable carrier. A monoclonal antibody directed to an epitope of a human betaine/GABA transporter present on the surface of a cell which has an amino acid sequence substantially the same as an amino acid sequence for a cell surface epitope of the human betaine/GABA transporter included in the amino acid sequences shown in FIGS. 1A–1D (SEQ ID NOs. 1 and 3) is useful for this purpose.

This invention also provides a method of treating abnormalities in a subject which are alleviated by reduction of expression of a mammalian betaine/GABA transporter which comprises administering to the subject an effective amount of the pharmaceutical composition described above effective to block binding of naturally occurring substrates to the mammalian betaine/GABA transporter and thereby alleviate abnormalities resulting from overexpression of the mammalian betaine/GABA transporter. This invention also provides a pharmaceutical composition which comprises an effective amount of an antibody directed to an epitope of a human betaine/GABA transporter, effective to block binding of naturally occurring substrates to the human betaine/GABA transporter, and a pharmaceutically acceptable carrier. A monoclonal antibody directed to a conserved epitope specific to a betaine/GABA transporter present on the surface of a cell which has an amino acid sequence substantially the same as an amino acid sequence for a cell surface epitope of the human betaine/GABA transporter included in the amino acid sequence shown in FIGS. 1A–1D (SEQ ID NOs. 1 and 3) is useful for this purpose. Binding of the antibody to the transporter prevents the transporter from functioning, thereby neutralizing the effects of overexpression. The monoclonal antibodies described above are both useful for this purpose. This invention additionally provides a method of treating an abnormal condition related to an excess of transporter activity which comprises administering to a subject an amount of the pharmaceutical composition described above effective to block binding of naturally occurring substrates to the transporter and thereby alleviate the abnormal condition. Some examples of abnormal conditions associated with abnormal betaine/GABA transporter activity are epilepsy, migraine, ischemia, myoclonus, spasticity, and the treatment of chronic pain.

This invention provides methods of detecting the presence of a betaine/GABA transporter on the surface of a cell which comprises contacting the cell with an antibody directed to the mammalian betaine/GABA transporter or an antibody directed to the human betaine/GABA transporter, under conditions permitting binding of the antibody to the transporter, detecting the presence of the antibody bound to the cell, and thereby the presence of the mammalian betaine/GABA transporter or the human betaine/GABA transporter on the surface of the cell. Such methods are useful for determining whether a given cell is defective in expression of betaine/GABA transporter on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a mammalian betaine/GABA transporter. This invention further provides a transgenic nonhuman mammal expressing DNA encoding a human betaine/GABA transporter. This invention also provides a transgenic nonhuman mammal expressing DNA encoding a mammalian betaine/GABA transporter so mutated as to be incapable of normal transporter activity and not expressing native betaine/GABA transporter activity. This invention further provides a transgenic nonhuman mammal expressing DNA encoding a human betaine/GABA transporter so mutated as to be incapable of normal transporter activity, and not expressing native betaine/GABA transporter.

This invention provides a transgenic nonhuman mammal whose genome comprises DNA encoding a mammalian betaine/GABA transporter so placed as to be transcribed into antisense mRNA which is complementary to mRNA encoding the betaine/GABA transporter and which hybridizes to mRNA encoding the betaine/GABA transporter thereby reducing its translation. This invention further provides a transgenic nonhuman mammal whose genome comprises DNA encoding a human betaine/GABA transporter so placed as to be transcribed into antisense mRNA which is complementary to mRNA encoding a betaine/GABA transporter and which hybridizes to mRNA encoding a betaine/GABA transporter thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1D (SEQ ID NOs. 1). An example of a transgenic animal is a transgenic mouse. Examples of tissue specificity-determining regions are the metallothionein promotor (Low et al., 1986,) and the L7 promotor (Oberdict et al. 1990).

Animal model systems which elucidate the physiological and behavioral roles of mammalian transporters are produced by creating transgenic animals in which the expression of a transporter is either increased or decreased, or the amino acid sequence of the expressed transporter protein is altered, by a variety of techniques. Examples of these techniques include, but are not limited to: 1) Insertion of normal or mutant versions of DNA encoding a mammalian transporter or homologous animal versions of these genes, by microinjection, retroviral infection or other means well known to those skilled in the art, into appropriate fertilized embryos in order to produce a transgenic animal (Hogan et al., 1986) Homologous recombination (Cappechi, M. R., 1989; Zimmer A., and Gruss, P., 1989) of mutant or normal, human or animal versions of these genes with the native gene locus in transgenic animals to alter the regulation of expression or the structure of these transporters. The technique of homologous recombination is well known in the art. It replaces the native gene with the inserted gene and so is useful for producing an animal that cannot express native transporter but does express, for example, an inserted mutant transporter, which has replaced the native transporter in the animal's genome by recombination, resulting in underexpression of the transporter. Microinjection adds genes to the genome, but does not remove them, and so is useful for producing an animal which expresses its own and added transporters, resulting in overexpression of the transporter.

One means available for producing a transgenic animal, with a mouse as an example, is as follows: Female mice are mated, and the resulting fertilized eggs are dissected out of their oviducts. The eggs are stored in an appropriate medium such as M2 medium (Hogan et al. 1986). DNA or cDNA encoding a human betaine/GABA transporter is purified from a vector (such as plasmid pcEXV-hBGT, ATCC Accession No. 75393, described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of transporter-specific drugs is to activate or to inhibit the transporter, the transgenic animal model systems described above are useful for testing the biological activity of drugs directed against these transporters even before such drugs become available. These animal model systems are useful for predicting or evaluating possible therapeutic applications of drugs which activate or inhibit these transporters by inducing or inhibiting expression of the native or trans-gene and thus increasing or decreasing expression of normal or mutant transporters in the living animal. Thus, a model system is produced in which the biological activity of drugs directed against these transporters are evaluated before such drugs become available. The transgenic animals which over or under produce the transporter indicate by their physiological state whether over or under production of the transporter is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less transporter by the affected cells, leading eventually to underexpression. Therefore, an animal which underexpresses transporter is useful as a test system to investigate whether the actions of such drugs which result in under expression are in fact therapeutic. Another use is that if overexpression is found to lead to abnormalities, then a drug which down-regulates or acts as an antagonist to the transporter is indicated as worth developing, and if a promising therapeutic application is uncovered by these animal model systems, activation or inhibition of the GABA transporter is achieved therapeutically either by producing agonist or antagonist drugs directed against these GABA transporters or by any method which increases or decreases the expression of these transporters in man.

Further provided by this invention is a method of determining the physiological effects of expressing varying levels of a mammalian betaine/GABA transporter which comprises producing a transgenic nonhuman animal whose levels of mammalian betaine/GABA transporter expression are varied by use of an inducible promoter which regulates transporter expression. This invention also provides a method of determining the physiological effects of expressing varying levels of mammalian Betaine/GABA transporter which comprises producing a panel of transgenic nonhuman animals each expressing a different amount of the mammalian betaine\GABA transporter. Such animals may be produced by introducing different amounts of DNA encoding a mammalian betaine/GABA transporter into the oocytes from which the transgenic animals are developed.

This invention provides a method of determining the physiological effects of expressing varying levels of a human betaine/GABA transporter which comprises producing a transgenic nonhuman animal whose levels of human betaine/GABA transporter expression are varied by use of an inducible promoter which regulates transporter expression. This invention also provides a method of determining the physiological effects of expressing varying levels of a human betaine/GABA transporter which comprises producing a panel of transgenic nonhuman animals each expressing a different amount of the human betaine/GABA transporter. Such animals may be produced by introducing different amounts of DNA encoding a human betaine/GABA transporter into the oocytes from which the transgenic animals are developed.

This invention also provides a method for identifying a substance capable of alleviating abnormalities resulting from overexpression of a mammalian betaine/GABA transporter comprising administering the substance to a transgenic nonhuman mammal expressing at least one artificially introduced DNA molecule encoding a mammalian betaine/GABA transporter and determining whether the substance alleviates the physical and behavioral abnormalities displayed by the transgenic nonhuman mammal as a result of overexpression of the mammalian betaine/GABA transporter. This invention also provides a method for identifying a substance capable of alleviating abnormalities resulting from overexpression of a human transporter comprising administering the substance to a transgenic nonhuman mammal expressing at least one artificially introduced DNA molecule encoding a human betaine/GABA transporter and determining whether the substance alleviates the physical and behavioral abnormalities displayed by the transgenic nonhuman mammal as a result of overexpression of a human betaine/GABA transporter. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A–1D (SEQ ID NO. 1).

This invention provides a pharmaceutical composition comprising an amount of the substance described supra effective to alleviate the abnormalities resulting from overexpression of a mammalian betaine/GABA transporter and a pharmaceutically acceptable carrier. This invention also provides a pharmaceutical composition comprising an amount of the substance described supra effective to alleviate the abnormalities resulting from overexpression of a human betaine/GABA transporter and a pharmaceutically acceptable carrier.

This invention also provides a method for treating the abnormalities resulting from overexpression of a mammalian betaine/GABA transporter which comprises administering to a subject an amount of the pharmaceutical composition described above effective to alleviate the abnormalities resulting from overexpression of a mammalian betaine/GABA transporter. This invention further provides a method for treating the abnormalities resulting from overexpression of a human betaine/GABA transporter which comprises administering to a subject an amount of the pharmaceutical composition described above effective to alleviate the abnormalities resulting from overexpression of the human betaine/GABA transporter.

This invention provides a method for identifying a substance capable of alleviating the abnormalities resulting from underexpression of a mammalian betaine/GABA transporter comprising administering the substance to the transgenic nonhuman mammal described above which expresses only nonfunctional mammalian transporter and determining whether the substance alleviates the physical and behavioral abnormalities displayed by the transgenic nonhuman mammal as a result of underexpression of a mammalian betaine/GABA transporter. This invention further provides a method for identifying a substance capable of alleviating the abnormalities resulting from underexpression of a human betaine/GABA transporter comprising administering the substance to the transgenic nonhuman mammal described above which expresses only nonfunctional human betaine/GABA and determining whether the substance alleviates the physical and behavioral abnormalities displayed by the transgenic nonhuman mammal as a result of underexpression of a human betaine/GABA.

This invention also provides a pharmaceutical composition comprising an amount of a substance effective to alleviate abnormalities resulting from underexpression of a mammalian betaine/GABA transporter and a pharmaceutically acceptable carrier. This invention also provides a pharmaceutical composition comprising an amount of a substance effective to alleviate abnormalities resulting from underexpression of a human betaine/GABA and a pharmaceutically acceptable carrier.

This invention provides a method for treating the abnormalities resulting from underexpression of a mammalian betaine/GABA transporter which comprises administering to a subject an amount of the pharmaceutical composition described above effective to alleviate the abnormalities resulting from underexpression of a mammalian betaine/GABA transporter. This invention further provides a method for treating the abnormalities resulting from underexpression of a human betaine/GABA transporter which comprises administering to a subject an amount of the pharmaceutical composition described above effective to alleviate the abnormalities resulting from underexpression of a human betaine/GABA transporter.

This invention provides a method for diagnosing a predisposition to a disorder associated with the expression of a specific mammalian betaine/transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a mammalian betaine/GABA transporter and labelled with a detectable marker; e) detecting labelled bands which have hybridized to the DNA encoding a mammalian betaine/GABA transporter labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific mammalian betaine/GABA transporter allele.

This invention provides a method for diagnosing a predisposition to a disorder associated with the expression of a specific human betaine/GABA transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human betaine/GABA transporter and labelled with a detectable marker; e) detecting labelled bands which have hybridized to the DNA encoding a human betaine/GABA labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human betaine/GABA transporter allele.

This invention provides a method of preparing an isolated betaine/GABA transporter which comprises inducing cells to express transporter, recovering the transporter from the resulting cells, and purifying the transporter so recovered. An example of an isolated betaine/GABA transporter is an isolated protein having substantially the same amino acid sequence as the amino acid sequence shown in FIGS. 1A–1D (SEQ ID NO. 1). This invention further provides a method for preparing an isolated human GABA transporter which comprises inducing cells to express the human betaine/GABA transporter, recovering the human betaine/GABA transporter from the resulting cells, and purifying the human betaine/GABA transporter so recovered. An example of an isolated human betaine/GABA transporter is an isolated protein having substantially the same amino acid sequence as the amino acid sequence shown in FIGS. 1A–1D (SEQ ID NOs. 1 and 3). For example, cells can be induced to express transporters by exposure to substances such as hormones. The cells can then be homogenized and the betaine/GABA transporter isolated from the homogenate using an affinity column comprising, for example, GABA, betaine or another substance which is known to bind to the betaine/GABA transporter. The resulting fractions can then be purified by contacting them with an ion exchange column, and determining which fraction contains betaine/GABA transporter activity or binds anti-betaine/GABA transporter antibodies.

This invention provides a method of preparing the isolated mammalian betaine/GABA transporter which comprises inserting nucleic acid encoding the mammalian betaine\GABA transporter in a suitable vector, inserting the resulting vector in a suitable host cell, recovering the transporter produced by the resulting cell, and purifying the transporter so recovered. An example of an isolated betaine/GABA transporter is an isolated protein having substantially the same amino acid sequence as the amino acid sequence shown in FIGS. 1A–1D (SEQ ID NOs 1 and 3). This invention also provides a method of preparing the isolated human betaine/GABA transporter which comprises inserting nucleic acid encoding a human betaine/GABA transporter in a suitable vector, inserting the resulting vector in a suitable host cell, recovering the transporter produced by the resulting cell, and purifying the transporter so recovered. These methods for preparing mammalian or human betaine/GABA transporter uses recombinant DNA technology methods well known in the art. For example, isolated nucleic acid encoding a mammalian or human betaine/GABA transporter is inserted in a suitable vector, such as an expression vector. A suitable host cell, such as a bacterial cell, or a eukaryotic cell such as a yeast cell, is transfected with the vector. Betaine/GABA transporter is isolated from the culture medium by affinity purification or by chromatography or by other methods well known in the art.

This invention provides a method for determining whether a compound not known to be capable of binding to a mammalian betaine/GABA transporter can bind to the mammalian betaine/GABA transporter which comprises contacting a mammalian cell comprising a DNA molecule encoding a mammalian betaine/GABA transporter with the compound under conditions permitting binding of compounds known to bind to the transporter, detecting the presence of any of the compound bound to the betaine/GABA transporter, and thereby determining whether the substrate binds to the betaine/GABA transporter.

This invention provides a method for determining whether a compound not known to be capable of binding to a human betaine/GABA transporter can bind to the human betaine/GABA transporter which comprises contacting a mammalian cell comprising a DNA molecule encoding a human betaine/GABA transporter with the compound under conditions permitting binding of compounds known to bind to the transporter, detecting the presence of any of the compound bound to the betaine/GABA transporter, and thereby determining whether the substrate binds to the betaine/GABA transporter. The DNA in the cell may have a coding sequence substantially the same as the coding sequences shown in FIGS. 1A–1D (SEQ ID NO. 1). Preferably, the mammalian cell is nonneuronal in origin. An example of a nonneuronal mammalian cell is a Cos7 cell or an L tk- cell. The preferred method for determining whether a compound is capable of binding to a mammalian or a human betaine/GABA transporter comprises contacting a transfected nonneuronal mammalian cell (i.e. a cell that does not naturally express any type of transporter, thus will only express such a transporter if it is transfected into the cell) expressing a transporter on its surface, or contacting a membrane preparation derived from such a transfected cell, with the substrate under conditions which are known to prevail, and thus to be associated with, in vivo binding of the substrates to a transporter, detecting the presence of any of the substrate being tested bound to the transporter on the surface of the cell, and thereby determining whether the substrate binds to the transporter. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of mammalian transporters with substrates as described above. Transfection systems are useful as living cell cultures for competitive binding assays between known or candidate drugs and substrates which bind to the transporter and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of the mammalian transporter and/or the human transporter. The transfection system is also useful for determining the affinity and efficacy of known drugs at the mammalian transporter sites and human transporter sites.

This invention also provides a method of screening drugs to identify drugs which specifically interact with, and bind to, the mammalian betaine/GABA transporter on the surface of a cell which comprises contacting a mammalian cell comprising a DNA molecule encoding a mammalian betaine/GABA transporter on the surface of a cell with a plurality of drugs, detecting those drugs which bind to the mammalian cell, and thereby identifying drugs which specifically interact with, and bind to, the mammalian betaine/GABA transporter. This invention also provides a method of screening drugs to identify drugs which specifically interact with, and bind to, a human betaine/GABA transporter on the surface of a cell which comprises contacting a mammalian cell comprising a DNA molecule encoding a human betaine/GABA transporter on the surface of a cell with a plurality of drugs, detecting those drugs which bind to the mammalian cell, and thereby identifying drugs which specifically interact with, and bind to, the human betaine/GABA transporter. The DNA in the cell may have a coding sequence substantially the same as the coding sequences shown in FIGS. 1A–1D (SEQ ID NO. 1). Various methods of detection may be employed. The drugs may be "labeled" by association with a detectable marker substance (e.g., radiolabel or a non-isotopic label such as biotin). Preferably, the mammalian cell is nonneuronal in origin. An example of a nonneuronal mammalian cell is a Cos7 cell or an L tk- cell. Drug candidates are identified by choosing chemical compounds which bind with high affinity to the expressed transporter protein in transfected cells, using radioligand binding methods well known in the art, examples of which are shown in the binding assays described herein. Drug candidates are also screened for selectivity by identifying compounds which bind with high affinity to one particular transporter subtype but do not bind with high affinity to any other transporter subtype or to any other known transporter site. Because selective, high affinity compounds interact primarily with the target transporter site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

Applicants have identified a human betaine/GABA transporter and have described methods for the identification of pharmacological compounds for therapeutic treatments. Pharmacological compounds which are directed against specific transporter subtypes provide effective new therapies with minimal side effects.

Elucidation of the molecular structures of the betaine/GABA transporter is an important step in the understanding of GABAergic neurotransmission. This disclosure reports the isolation, amino acid sequence, and functional expression of a DNA clone from human brain which encodes a betaine/GABA transporter. The identification of this betaine/GABA transporter will play a pivotal role in elucidating the molecular mechanisms underlying GABAergic transmission, and should also aid in the development of novel therapeutic agents.

Complementary DNA clones (designated hS1a, hS13a, hS26a and hS38a) encoding betaine/GABA transporters have been isolated from human brain, and their functional properties have been examined in mammalian cells. The nucleotide sequence of hS1a predicts a protein of 614 amino acids with 12 highly hydrophobic regions compatible with membrane-spanning domains. When incubated with 50 nM [$^3$H]GABA, COS cells transiently transfected with hS1a accumulated approximately 10-fold greater radioactivity as non-transfected control cells. In stable LM tk- cell lines expressing hS1a, a 92 fold enhancement of [$^3$H]GABA uptake was observed, compared to non-transfected cells.

Analysis of the betaine/GABA transporter structure and function provides a model for the development of drugs useful for the treatment of epilepsy, migraine, ischemia, myoclonus, spasticity, and chronic pain.

This invention identifies for the first time a betaine/GABA transporter protein, its amino acid sequence, and its human gene. The information and experimental tools provided by this discovery are useful to generate new therapeutic agents, and new therapeutic or diagnostic assays for this new transporter protein, its associated mRNA molecules or its associated genomic DNAs. The information and experimental tools provided by this discovery will be useful to generate new therapeutic agents, and new therapeutic or diagnostic assays for this new transporter protein, its associated mRNA molecules, or its associated genomic DNAs.

This invention provides a method for screening compounds to identify drugs that interact with, and specifically bind to, a human betaine/GABA transporter, which comprises preparing a cell extract from insect cells, which comprise an expression vector adapted for expression in an insect cell which vector further comprises DNA which expresses a human betaine/GABA transporter on the cell's surface, isolating a membrane fraction from the cell extract, incubating the membrane fraction with a plurality of compounds, determining those compounds which interact with and bind to the human betaine/GABA transporter, and thereby identifying compounds which interact with, and specifically bind to, the human betaine/GABA transporter.

Specifically, this invention relates to the first isolation of cDNAs encoding a betaine/GABA. In addition, the human betaine/GABA transporter has been expressed in Cos7 cells and LM tk- cell by transfecting the cells with the plasmid containing DNA encoding the human betaine/GABA transporter. The pharmacological binding properties of the encoded betaine/GABA has been determined, and its binding properties classify this protein as betaine/GABA transporter. Mammalian cell lines expressing the human betaine/GABA transporter on the cell surface have been constructed, thus establishing the first well-defined, cultured cell lines with which to study the betaine/GABA transporter.

This invention further provides a method of treating an abnormal condition such as epilepsy, migraine, ischemia, myoclonus, spasticity or chronic pain. The abnormal condition may be associated with overexpression or underexpression of the betaine/GABA transporter or may be associated with the presence of excess or deficient amounts of naturally occuring substrates the transport of which is controlled by the betaine/GAB transporter. In the case of overexpression of the transporter, the abnormal condition may be treated by administering, in the form of pharmaceutical composition, a ligand which specifically binds to the betaine/GABA transporter and inhibits the transport of a naturally occuring substrate. In the case of underexpression, the abnormal condition may be treated by administering, in the form of a pharmaceutical composition, a ligand which specifically binds to the transporter and enhances the transport of a natural occuring substrate. In the case of an excess amount of a naturally occuring substrate the abnormal condition may be treated by administering a ligand which competitively inhibits binding, and thus transport, of the natural occuring substrate Finally, in the case of a deficient amount of a naturally occuring substrate the abnormal condition may be treated by either administering a ligand which enhances binding or transport of the natural occuring substrate or binds to the transporter and mimics the biological function of the natural occuring substrate. In all cases the ligand is present in a pharmaceutical acceptable carrier in an amount effective to accomplish the desired effect.

This invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

Abbreviations: ACHC, cis-3-aminocyclohexanecarboxylic acid; GABA, γ-aminobutyric acid; GES, guanidinoethanesulfonic acid; HBS, HEPES-buffered saline; HEPES, N-[2-Hydroxyethyl]piperazine-N'-[2-ethanesulfonic acid]; L-DABA; L-(2,4)diaminobutyric acid); GAT-1, the GABA transporter originally cloned by Guastella et al. (1990) rom rat brain; GAT-2 and GAT-3, additional GABA transporters cloned from rat brain (Borden et al., 1992); hGAT-1 (Nelson et al., 1990) and hGAT-3 (Smith et al., in preparation), the human homologues of rat GAT-1 and rat GAT-3, respectively; BGT-1, the betaine/GABA transporter originally cloned from dog (Yamauchi et al., 1992); human BGT-1, the human homologue of dog BGT-1; mouse BGT-1, the mouse homologue of dog BGT-1 (termed GAT-2 by Lopez-Corcuera et al., 1992); RT-PCR, reverse transcriptase-polymerase chain reaction.

CLONING AND EXPRESSION OF A BETAINE/GABA TRANSPORTER (BGT-1) FROM HUMAN BRAIN

MATERIALS and METHODS

Materials: [$^3$H]GABA (98.9 Ci/mmole) and $^{35}$S-dATP (1200 Ci/mmole) was obtained from New England Nuclear (Boston, Mass.). GABA, betaine, p-alanine, phloretin, quinidine, taurine, hypotaurine, and L-DABA were from Sigma Chemical Corporation (St. Louis, Mo.); guvacine, nipecotic acid, NNC-711, ACHC (cis-3-aminocyclohexanecarboxylic acid), and OH-nipecotic (hydroxynipecotic acid) were from Research Biochemicals International (RBI), 1 Strathmore Rd., Natick, Mass., 01760. GES can be prepared according to the method of Fujii, et al. (1975). Cell culture media were obtained from Specialty Media (Lavallette, N.J.), and serum was from UBI (Lake Placid, N.Y.).

Use of PCR to Identify CDNA Libraries for Screening: Degenerate primers were designed to amplify putative human GAT-2 CDNA clones based on sequence comparisons between conserved regions of several transporters. The sequences of the degenerate primers were 5'-TGGAATTCG (G/C)CAA(C/T)GTTTGG(C/A)GITT(C/T)CCITA (sense) and 5'-TCGCGGCCGCAA(A/G)AAGATCTGIGTTGCIGC (A/G)TC (antisense). PCR reactions were carried out in a buffer containing 20 mM Tris (pH 8.3), 50 mM KCl, 1.5 mM $MgCl_2$, 0.001% gelatin, 2 mM dNTP's, 1 µM each primer, Taq polymerase, and an aliquot of a lambda phage library, water, or a control plasmid for 40 cycles of 94° C. for 2 min., 40° C. for 2 min., and 72°C. for 3 min. PCR products were separated by electrophoresis in 1.2% agarose gels, blotted to nylon membranes (Genescreen Plus; New England Nuclear, Boston, Mass.), and hybridized at high stringency overnight with $^{32}$P-labeled probes representing the rat GAT-2 sequence (overlapping 45 mers: sense, 5'-GTCCTGAAGATCTCAGATGGCATCCAGCACCTGG GGTCCCTGCGC (SEQ ID No. 3); antisense, 5'-GCAGGAGGCACAGGACCAGCTCCCAGCGCAGG GACCCCAGGTGCT (SEQ ID No. 4). Hybridization was at 40° C. in a solution containing 50% formamide, 10% dextran sulfate, 5×SSC, 1×Denhardt's, and 100 µg/ml of sonicated salmon sperm DNA. Blots were washed at high stringency (0.1×SSC, 50° C.) and exposed to Kodak XAR film overnight with one intensifying screen at −70° C.

Isolation and Sequencing of Human Betaine/GABA CDNA Clones: A human striatum cDNA library in the Lambda ZAP II vector (Stratagene, La Jolla, Calif.) identified by PCR was screened under high stringency (50% formamide, 40° C. hybridization; 0.1×SSC, 50° C. wash) with the rat GAT-2 probes described above. Hybridizing lambda phage were plaque purified and converted to phagemids by in vivo excision with f1 helper phage. Nucleotide sequences of double-stranded cDNAs in pBluescript were analyzed by the Sanger dideoxy nucleotide chain-termination method (Sanger, 1977) using Sequenase (U.S. Biochemical Corp., Cleveland, Ohio). A cDNA clone (designated hS1a) identified as representing the entire coding region of a novel human transporter was subcloned into a eukaryotic expression vector (modified from pcEXV-3, Miller and Germain, 1986) as a 3.1 Kb XbaI/SalI fragment.

Transfection: Transient transfections of COS cells were carried out using DEAE-dextran with DMSO according to the method of Lopata et al. (1984), with minor modifications, or according to the method of Smith et al. (1992) with minor modifications. COS cells grown in 75 $cm^2$ or 150 $cm^2$ flasks in DMEM with 10% bovine calf serum, 100 U/ml penicillin G, and 100 µg/ml streptomycin sulfate (37° C., 5% $CO_2$) were transfected using DEAE-dextran. On the day following transfection the cells were split into 24-well assay plates, and transport was measured 24 hours later.

Stable transfection: Stable cell lines expressing hBGT-1 were generated in LM(tk⁻) cells using the calcium phosphate method and selection in G-418, as described previously (Weinshank et al., 1992). Cells were grown under standard conditions (37° C., 5% $CO_2$) in Dulbecco's modified Eagles's medium (GIBCO, Grand Island, N.Y.). Similar results were obtained with transient and stable transfectants.

Northern Blot Analysis of hBGT-1 mRNA: Human brain total RNA was purchased from Clontech (Palo Alto, Calif.). Denatured RNAs (25 µg) were separated by electrophoresis in 1.0% agarose gels containing 2.7% formaldehyde and then transferred to a GeneScreen Plus nylon membrane (Dupont-NEN, Boston, Mass.) by overnight capillary blotting in 10×SSC. Prehybridization was for 1–2 hours at 42° C. in a solution containing 50% formamide, 1M sodium chloride, 10% dextran sulfate and 1.0% SDS. The blot was hybridized overnight at 42° C. with $^{32}$P-labeled randomly-primed probe (1.5 kb NcoI fragment of hBGT-1; Prime-It II Kit, Stratagene, La Jolla, Calif.) in prehybridization mixture containing 100 µg/ml sonicated salmon sperm DNA. The blot was washed successively in 2×SSC/2% SDS for 1 hour, 1×SSC/2% SDS for 45 minutes, and 0.2×SSC/2% SDS for 45 minutes at 65° C., then exposed to Kodak XAR-5 film with one intensifying screen at 80° C. for 10 days.

To determine the regional localization of BGT-1 mRNA, a Northern blot containing mRNA from multiple brain regions (Clontech) was hybridized with the hBGT-1 probe (see above) overnight at 42° C. in a solution containing 5×SSPE, 10×Denhardt's, 50% formamide, 2% SDS, and 100 µg/ml sheared salmon sperm DNA. The blot was washed at room temperature for 40 minutes in 2×SSC/0.05% SDS, then at 50° C. for 40 minutes in 0.1×SSC/0.05% SDS. After overnight exposure to Kodak XAR-5 film, the blot was reprobed for β-actin to confirm that equal amounts of RNA were present in each lane.

Transport assay: Transport by attached cells was measured as described previously (Borden et al. 1992), with the following modifications. Cells grown in 24-well plates (well diameter=18 mm) were washed 3× with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate on a 37° C. slide warmer. After 10 minutes the medium was removed and unlabeled drugs in HBS were added (450 µl/well). Transport was initiated by adding 50 µl per well of a concentrated solution of [$^3$H]GABA in HBS (final concentration=50 nM). Non-specific uptake was defined in parallel wells with 1 mM unlabeled GABA, and was subtracted from total uptake (no competitor) to yield specific uptake; all data represent specific uptake. Plates were incubated at 37° C. for 10 minutes, then washed rapidly 3× with ice-cold HBS, using a 24-position plate washer (Brandel, Gaithersburg, Mass.; model PW-12). Cells were solubilized with 0.05% sodium deoxycholate/0.1N NaOH (0.25 ml/well), an aliquot neutralized with 1N HCl, and radioactivity was determined by scintillation counting. Protein was quantified in an aliquot of the solubilized cells using a BIO-RAD protein assay kit, according to the manufacturer's directions.

Transport was also measured in suspension. Briefly, transient (COS-7) or stable (LM) transfectants were removed from culture plates with trypsin/EDTA, and transferred to suspension culture. The cells were grown in a temperature-controlled shaking incubator, using a medium containing methylcellulose. To measure transport the cells were washed by centrifugation, and resuspended in HBS. The assay was performed in 96-well microtiter plates (total volume=0.25 ml/well). The cells were incubated with 50 nM [$^3$H]GABA and required drugs for 10 minutes at 37° C., then collected using a Brandel harvester. Cell-associated radioactivity retained on the filters was determined by scintillation counting.

Data Analysis: Competition curves were conducted in duplicate, using 10 concentrations of unlabeled drug. $IC_{50}$ values (concentrations resulting in 50% inhibition of uptake) were derived using software from GraphPad Inplot (San Diego, Calif.). Data were not corrected for the concentration of radioligand since [$^3$H]GABA was employed at a concentration well below its $K_M$; however, since initial rates were not studied, data are presented as $IC_{50}$. All data throughout the paper represent means±SEM.

In Situ Hybridization: Male mice (Charles River) were decapitated and the brains rapidly removed and frozen in isopentane. Coronal sections were cut at 11 µm on a cryostat, thaw mounted onto poly-L-lysine coated glass slides and stored at −80° C. until used. Immediately prior to hybridization, the tissues were fixed in 4% paraformaldehyde, treated with 5 mM dithiothreitol, acetylated in 0.1M triethanolamine containing 0.25% acetic anhydride, delipidated with chloroform and dehydrated in graded ethanols.

Antisense and sense oligonucleotide probes (45 mers), corresponding to nucleotides 1894–1938 of the 3'-untranslated region of the mouse betaine transporter (Lopez-Corcuera et al., 1992) were synthesized on a Cyclone Plus DNA Synthesizer (Milligen/Bioresearch) and gel-purified. The probes were 3'-end labeled with $^{35}$S-dATP (1200 Ci/mmol, New England Nuclear, Boston, Mass.) to a specific activity of $10^9$ dpm/µg using terminal deoxynucleotidyl transferase (Boehringer Mannheim; Indianapolis, Ind.). The radiolabeled probes were purified on Biospin 6 chromatography columns (Bio-Rad; Richmond, Calif.), and diluted in hybridization buffer to a concentration of $1.5 \times 10^4$ cpm/µl. The hybridization buffer consisted of 50% formamide, 4× sodium citrate buffer (1×SSC=0.15M NaCl and 0.015M sodium citrate), 1×Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate. One hundred µl of the radiolabeled probe was applied to each section, which was then covered with a Parafilm coverslip. Hybridization was carried out overnight in humid chambers at 42° C. The following day the sections were washed in two changes of 2×SSC for one hour at room temperature, in 2×SSC for 30 min at 50°–60° C., and finally in 0.1×SSC for 30 min at room temperature. Tissues were dehydrated in graded ethanols and apposed to Kodak XAR-5 film for 4 to 11 days at –20° C., then dipped in Kodak NTB3 autoradiography emulsion diluted 1:1 with 0.2% glycerol water. After exposure in light-tight boxes at 4° C. for 3 weeks, the slides were developed in Kodak D-19 developer, fixed, and counterstained with hematoxylin and eosin.

RESULTS

Cloning of the Human Betaine/GABA Transporter

A human striatum library (Stratagene) was screened at high-stringency with probes obtained from the rat GAT-2 transporter cDNA; positive plaques were purified by successive screening at high stringency. Four cDNA clones were isolated (hS1a, hS13a, hS26a, and hS38a) that exhibited significant homology to the nucleotide sequence of rat GAT-2, but were too dissimilar to represent species homologues of this clone. One of these, hS1a, was determined by sequence analysis to contain the full coding region of a novel transporter; the complete nucleotide sequence and predicted amino acid sequence of this clone are shown in FIGS. 1A–1D. The nucleotide sequence of the coding region of hS1a displayed a high degree of identity to dog BGT-1 (89%; Yamauchi et al., 1992) and the related mouse cDNA (86%; Lopez-Corcuera et al., 1992). Translation of a long open reading frame of hS1a predicts a protein of 614 amino acids with 12 putative transmembrane domains. As expected, the predicted amino acid sequence displayed a higher degree of identity with dog BGT-1 (91%) and mouse BGT-1 (87%; Lopez-Corcuera et al., 1992), than with rat GAT-2 (70%) or rat GAT-3 (66%), the next closest relatives (see FIGS. 2A–2G). This finding, and the ability of hS1a to confer high-affinity GABA transport activity following transfection into host cells (see below), together suggest that the new clone represents the human homologue of dog BGT-1; accordingly, we refer to it as human BGT-1.

Two potential sites for N-linked glycosylation are present in the predicted extracellular loop between TMs III and IV of human BGT-1, as in dog and mouse. Despite their high overall amino acid identities, alignment of human, mouse, and dog BGT-1 sequences reveals several non-conservative amino acid substitutions in the human sequence (FIGS. 2A–2G). Differences are also observed in the number and location of potential sites for phosphorylation by casein kinase II and protein kinase C between the three homologues (data not shown). The functional significance of these variations is not yet known, but they could potentially affect the pharmacological properties and/or regulation of the transporter.

Expression and Pharmacological Characterization of Human Betaine/GABA Transporter.

Transient transfection of COS-7 cells with hS1a resulted in a 9-fold increase in the specific uptake of [$^3$H]GABA as compared to non-transfected controls (FIG. 3). The GABA transporter encoded by hS1a was also studied in stably transfected LM(tk$^-$) cells, as described in Methods. The highest level of expression was observed in clone 3 (termed L-hBGT-1-3), which was used for subsequent characterization. As shown in FIGS. 4A–4D, [$^3$H]GABA uptake by L-hBGT-1-3 was increased 20-fold as compared to non-transfected cells. Thus, enhanced uptake of [$^3$H]GABA was observed with both transient and stable transfectants. [$^3$H] GABA uptake by L-hBGT-1-3 was decreased >95% in medium lacking either Na$^{2+}$ or Cl$^-$ (data not shown), similar to results obtained with the dog homologue (Yamauchi et al, 1992). To determine the pharmacological specificity of hS1a, a number of compounds were examined for their ability to inhibit the transport of [$^3$H]GABA by L-hBGT-1-3 (Table 1); the published data for the dog and mouse clones are shown for comparison. GABA itself was the most potent inhibitor, displaying an IC$_{50}$ of 36 µM. The next most potent inhibitors were phloretin, L-DABA, hypotaurine, and NNC-711, with IC$_{50}$ values between 160 and 600 µM. The other compounds tested, including betaine, displayed IC$_{50}$s between 1 and 2 mM. Taurine was the weakest agent tested, with an IC$_{50}$>10 mM.

TABLE 1

Pharmacological profile of betaine/GABA transporters from human, dog, and mouse.

| | IC$_{50}$, µM | | |
|---|---|---|---|
| | hBGT-1[1] | dog VGT-1[2] | mouse GAT-2[3] |
| GABA | 36 ± 3 | 93 | 79 |
| phloretin | 160 ± 18 | 200 | 37 |
| L-DABA | 354 ± 42 | 4,700 | |
| hypotaurine | 380 ± 9 | | |
| NNC-711 | 622 ± 265 | | |
| betaine | 934 ± 22 | 398 | 206 |
| quinidine | 1,190 ± 96 | 325 | 49 |
| β-alanine | 1,320 ± 224 | 2,400 | 1,900 |
| GES | 1,520 ± 88 | | |
| ACHC | 1,850 ± 363 | | |
| guvacine | 1,870 ± 387 | | 2,800 |
| (±)nipecotic acid | 2,350 ± 253 | 4,700 | 8,000 |
| hydroxynipecotic acid | 2,590 ± 324 | | |
| taurine | 10,600 ± 2190 | | |

[1]inhibition of [$^3$H] GABA uptake in stably transfected LM(tk$^-$). Each value is the mean ± standard error of at least three experiments.
[2]inhibition of [$^3$H] GABA uptake in oocytes (Yamauchi et al., 1992); IC$_{50}$ values (except for GABA) are estimated from percent inhibition at a single concentrations
[3]inhibition of [$^3$H] GABA uptake in oocytes (Lopez-Corcuera et al., 1992); IC$_{50}$ values (except for GABA) are estimated from percent inhibition at one or two concentrations

Regional Localization of BGT-1 mRNA in Brain

To define the size of the transcript encoding human BGT-1 we prepared a Northern blot of total human brain RNA. Hybridization with a radiolabeled fragment of hBGT-1 revealed a single ≈3.1 kb transcript (FIG. 4A); this finding, and the pharmacological data, suggest that hS1a represents a full-length cDNA. Detection of the hBGT-1 transcript in total RNA from human brain confirms the differential distribution of BGT-1 mRNA in human and dog (see Yamauchi et al, 1992).

To map the distribution and abundance of hBGT-1 transcripts within the brain, we carried out Northern blot analysis of mRNA isolated from eight human brain regions. The ≈3.1 kb transcript was present at similar abundance in all regions examined (FIG. 4B), revealing a wide pattern of distribution for hBGT-1 in human brain. The transcript was also detected in human kidney mRNA by RT-PCR (data not shown).

Figures 5A, 5B:
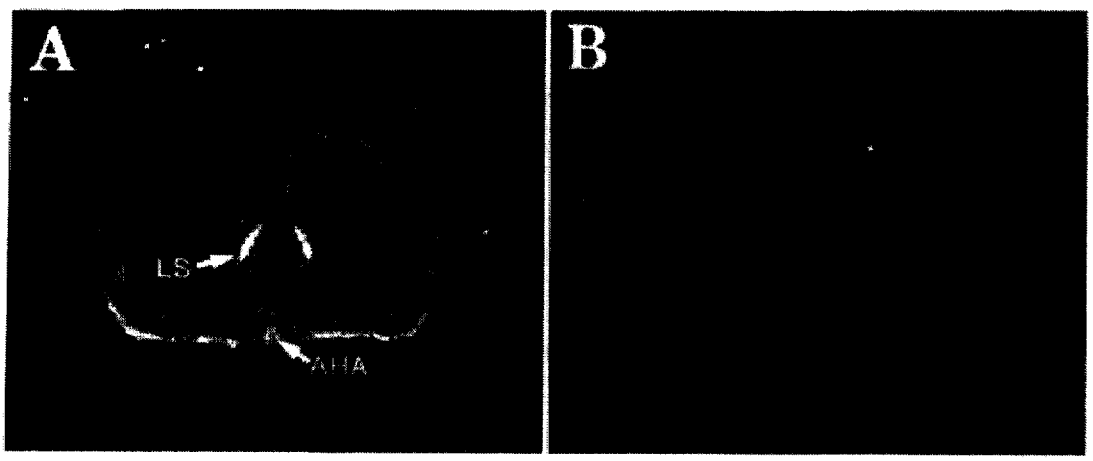
FIG. 5A. Cellular Localization of mouse BGT-1 mRNA. Photomicrographs illustrating the localization of BGT mRNA in the mouse brain as revealed by in situ hybridization histochemistry. Low magnification reversal micrograph of a coronal section hybridized with the BGT antisense oligonucleotide, showing an intense hybridization signal over the septum (LS) and a moderate signal over anterior hypothalamus (AHA). Note that low levels of hybridization signal are present over most of the remainder of the section.
FIG. 5B. Cellular Localization of mouse BGT-1 mRNA. Photomicrographs illustrating the localization of BGT mRNA in the mouse brain as revealed by in situ hybridization histochemistry. Low magnification reversal micrograph of a coronal section hybridized with the BGT sense probe. Only a weak signal is present over the lateral septum.

To determine the localization of BGT-1 mRNA at the cellular level, we employed in situ hybridization. Due to the paucity of well-preserved human brain tissue, we performed the localization studies in mouse brain using oligonucleotide probes to mouse BGT-1, as described in Methods. Hybridization with radiolabeled antisense probes revealed low to moderate labeling in all brain regions (FIG. 5A); in contrast, no autoradiographic signal, either on film or in emulsion-dipped sections, was observed following hybridization with sense probes (FIG. 5B). At the microscopic level, silver grains were observed over many neuronal perikarya, in all regions of the mouse brain. The largest accumulations of grains over individual neurons were seen in the lateral septum (FIG. 5A, C), and the preoptic nucleus of the anterior hypothalamus (FIG. 5A, D).

Figure 5C:
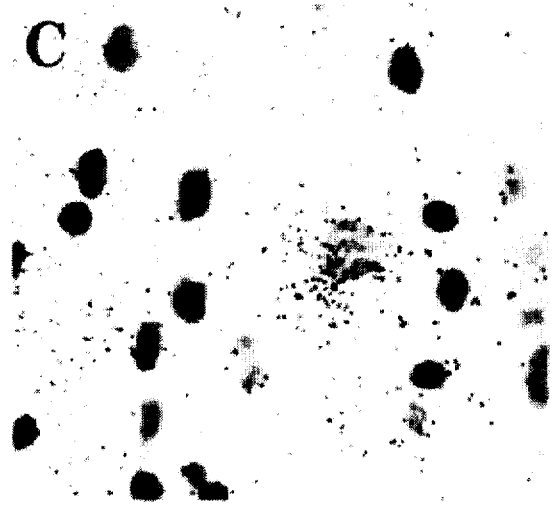
FIG. 5C. High magnification photomicrograph of the hybridization signal over individual neurons in the lateral septum (mouse BGT-1 mRNA antisense probe). The cell nuclei at the left of the panel are clearly visible, with silver grains over the cytoplasm.
Figure 5D:
FIG. 5D. Photomicrograph of the signal observed over individual cells in the anterior hypothalamus (mouse BGT-1 mRNA antisense probe). Marker bar=20 µm and applies to FIG. 4C also.

In the lateral septum, there was a strip of labeled medium-sized neurons (≈11–18 µm in long diameter), which extended ventrolaterally from near the midline to the lateral ventricle (FIG. 5C). In the hypothalamus, the most heavily labeled neurons, 10–13 µm in long diameter, were found in the preoptic nucleus (FIG. 5D). While it is often difficult to determine localization of silver grains over glial cells, due to the small area of cytoplasm, the antisense oligonucleotide probe used in the current study did not appear to hybridize to glial cells in the mouse brain.

Discussion

In this communication we describe the cloning and expression of a human betaine/GABA transporter from a brain CDNA library. This transporter displays 91% and 87% amino acid identity with dog BGT-1 (Yamauchi et al., 1992) and the related mouse clone (Lopez-Corcuera et al., 1992), respectively. These values are similar to the amino acid identities between human, rat, and dog taurine transporters (91–93%), rat and human dopamine transporters (92%), and between rat and human homologues of the GABA transporter GAT-3 (95%), though they are slightly less than the identity between the species homologues of the GABA transporter GAT-1 (97–99%). These data indicate that the dog betaine/GABA transporter, the related mouse clone, and the human clone described here are species homologues; accordingly, we adhere to the original nomenclature of Yamauchi et al. (1992) and refer to all three clones as BGT-1.

The pharmacologic profiles of the three BGT-1 transporters bear some similarities, but also significant differences. The affinities of GABA and β-alanine are similar among the three transporters, varying by only 2- to 3-fold. Similarly, betaine displays 2-fold and 5-fold selectivity for mouse BGT-1 as compared to the dog and human clones, respectively. In contrast, other drugs show greater variation in affinity. For example, phloretin show 4- to 5-fold selectivity for mouse BGT-1 as compared to dog and human BGT-1. Quinidine is the most selective of the compounds tested, displaying potency at mouse BGT-1 that is 7-fold and 25-fold greater than the dog and human BGT-1, respectively. While all three clones show higher affinity for GABA than for betaine (the presumed natural substrates), the selectivity is 3- to 4-fold for the mouse and dog clones, but 26-fold for human BGT-1. The similar affinities of GABA and β-alanine at the three clones suggest that the differences observed for some of the drugs are not due to methodological differences between laboratories, such as the use of fibroblasts or oocytes, or differences in the time and temperature of transport measurements. Rather, they suggest that species differences in transporter structure result in differential drug sensitivities. Pharmacological differences attributable to sequence differences are well known in G-protein-coupled receptors (Adham et al., 1992; Kao et al., 1992; Link et al., 1992). The current data suggest that this phenomenon also occurs in transporters and underscores the importance of using human clones in drug development, as has been discussed previously (Hartig, 1992).

The ability of BGT-1 to utilize both GABA and betaine as substrates (Yamauchi et al., 1992) suggests that it might serve multiple physiological roles. Yamauchi et al. (1992, and references therein) noted that the plasma levels of betaine (180 µM) are considerably higher than those of GABA (1 µM) and thus concluded that, despite the 4-fold higher affinity of the transporter for GABA than for betaine, betaine is the physiological substrate in the renal medulla. Northern blots did not reveal the presence of BGT-1 mRNA in dog brain, suggesting that in this species the action of betaine is limited to that of osmoregulation in the kidney; however, more sensitive techniques such as PCR will be required to determine whether BGT-1 is truly absent from dog brain, or if it is simply present at low levels.

The presence of BGT-1 mRNA in the human and mouse brains suggests that, in these species, betaine also functions in regulating neural function. Betaine has been detected in brain where it is thought to serve an osmoregulatory function (Heilig et al., 1989). It is normally present in low concentrations but levels are increased following salt-loading (Heilig et al., 1989). Because the brain is suspended in a rigid container (ie., the skull), volume regulation is critical to the proper functioning of the central nervous system. It is of interest that hGBT displays a relatively high degree of sequence identity (61%) with the transporter for taurine (Smith et al., 1992b), a major osmoregulator in the central nervous system.

GABA is the major inhibitory neurotransmitter in the mammalian brain and heterogeneity of GABA transporters is well documented (see Introduction). A role for BGT-1 in GABAergic transmission is supported by the presence of BGT-1 mRNA in mouse and human brain and by the finding that, when assayed under identical conditions, the affinity of GABA for hBGT-1 is within 2- to 3-fold of its affinities for GAT-1, GAT-2, and GAT-3 (Borden et al., submitted). Further, as described above, human BGT-1 displays 25-fold higher affinity for GABA than for betaine, and is thus a high-affinity GABA transporter. Since the dog transporter is capable of utilizing both betaine and GABA as substrates, this additional function for BGT-1 in brain would not have required extensive structural changes in the transporter.

In situ hybridization and Northern blot studies revealed a wide-spread distribution of BGT-1 mRNA in the mouse and human brain which does not closely match the localization of GABAergic pathways. This lack of correspondence suggests that BGT-1 might not play a role in terminating the action of GABA at the synapse; rather, it may serve to sequester GABA that has diffused away from synaptic regions, thereby assuring the fidelity of transmission. The development of specific, high-affinity inhibitors of BGT-1 should help elucidate the role of this transporter in nervous function, and may represent novel therapeutic agents.

The cellular localization of BGT-1 in the human brain remains to be determined. It should be noted that in contrast to the localization in mouse brain, which suggests a neuronal distribution, rat BGT-1 mRNA is more abundant in primary rat glial cultures than in primary neuronal cultures (Borden et al., submitted). A transcript with a low copy number per cell distributed among many cells may be difficult to detect by in situ hybridization; therefore, the apparently neuronal distribution of BGT-1 mRNA in mouse brain does not preclude glial expression. The wide distribution of BGT-1 mRNA we observe in human brain would be consistent with BGT-1 expression in brain astrocytes as well as neurons.

Alterations in osmoregulation and in GABAergic transmission have been implicated in a variety of neuropathological and psychiatric conditions. Our cloning of a human betaine/GABA transporter will help elucidate its role in the central nervous system, and will further our understanding of the roles of GABA and betaine in neural function. Additionally, the cloned transporter will aid in the development of specific, high-affinity ligands for this transporter. The use of human gene products in the process of drug development offers significant advantages over those of other species, which may not exhibit the same pharmacologic profiles. The development of such drugs may be useful in a variety of conditions, including (though not restricted to) epilepsy, migraine, ischemia, myoclonus, spasticity, and the treatment of chronic pain.

RE-EVALUATION OF GABA TRANSPORT IN NEURONAL AND GLIAL CELL CULTURES: CORRELATION OF PHARMACOLOGY AND mRNA LOCALIZATION

It is now well established that sodium-dependent neurotransmitter transporters are key components of the synaptic machinery which mediates chemical transmission in the vertebrate nervous system. Neurotransmitter transporters may serve a number of important functions in synaptic transmission including termination of synaptic transmission, prevention of the spread of transmitter (thereby assuring the fidelity of transmission), and reutilization of neurotransmitter (see Krogsgaard-Larsen, 1987 for review). In addition, transporters may also work in reverse, releasing neurotransmitter in a calcium-independent manner (Levi and Raiteri, 1993; Attwell et al., 1993). Available data suggest that neurotransmitter transporters are located on the plasmalemma of presynaptic terminals and surrounding astroglial cells, though the relative contribution of each remains to be established.

Pharmacological inhibition of neurotransmitter transport provides a means for increasing neurotransmitter levels in the synapse, thereby enhancing synaptic transmission. The therapeutic utility of this approach is exemplified by the classical tricyclic antidepressants which inhibit the uptake of the monoamine neurotransmitters such as norepinephrine and serotonin. In contrast, less is known regarding the therapeutic potential of inhibiting the transport of other classes of neurotransmitter, such as the inhibitory amino acid transmitters. γ-Aminobutyric acid (GABA[1]) is the major inhibitory neurotransmitter in the mammalian brain. Modulation of GABAergic activity has important therapeutic benefit as evidenced by drugs such as benzodiazepines and barbiturates which bind to allosteric modulatory sites on the $GABA_A$ receptor, thereby increasing the affinity for GABA. Inhibition of GABA transport represents a novel approach to increasing GABAergic activity which may prove useful in the treatment of epilepsy, anxiety, and other neuropsychological disorders. An important step in the realization of this goal is a more thorough understanding of the properties of GABA transporters.

Cell cultures derived from mammalian brain have proven to be useful models for the study of GABA transport and lead to the classification of distinct neuronal and glial GABA transporter systems (see Krogsgaard-Larsen, 1987 for review). These two transport systems are distinguished by ACHC and L-DABA, which have higher affinity for the neuronal transporter, and by β-alanine, which shows selectivity for the glial transporter. Other transport inhibitors such as nipecotic acid, hydroxynipecotic acid, and guvacine show varying degrees of selectivity for the glial transporter (Krogsgaard-Larsen, 1987).

Molecular biology has greatly increased our understanding of sodium-dependent neurotransmitter transporters (see Amara and Arriza, 1993, for review). The first neurotransmitter transporter to be cloned was a high affinity GABA transporter isolated from rat brain, termed GAT-1 (Guastella et al., 1990), which displays a pharmacological profile consistent with the "neuronal" transporter. Subsequently two additional high-affinity GABA transporters, GAT-2 and GAT-3 were cloned from rat brain (Borden et al., 1992); a clone identical to GAT-3 was described by Clark et al. (1992) and termed GAT-B. An additional member of the GABA transporter family was cloned from dog kidney and transports both the osmolyte betaine and GABA, and was thus referred to as BGT-1 (Yamauchi et al., 1992). We have recently cloned the human homologue of BGT-1 from a human brain cDNA library (L. A. Borden, K. E. Smith, E. L. Gustafson, T. A. Branchek, and R. L. Weinshank, unpublished observations), confirming its expression in the central nervous system. Clones for all four GABA transporters have been identified in mice, although a different nomenclature was employed (Liu et al., 1993).

In contrast to GAT-1, the relationship of GAT-2, GAT-3, and BGT-1 to the pharmacologically characterized neuronal and glial transport systems is not understood. While GAT-2 and GAT-3 display high affinity for β-alanine and low affinity for ACHC, suggesting a similarity to the glial transporter, their overall pharmacological profile indicates that they are distinct from this site. Additionally, the observation that GAT-3/GAT-B is located in neurons (Clark et al., 1992; M. M. Durkin, E. L. Gustafson, K. E. Smith, L. A. Borden, P. R. Hartig, R. L. Weinshank, and T. A. Branchek, unpublished observations) indicates that neuronal transport is not limited to GAT-1, and that β-alanine sensitivity is not unique to glial GABA transport.

An additional level of complexity results from the heterogeneity of astrocytes. Two types of astrocytes, termed Type 1 and Type 2, have been described in cell cultures (for reviews see Raff, 1989; Miller et al., 1989). Interestingly, it has been suggested that Type 2 astrocytes and their precursor, termed O-2A, display a "neuronal-like" GABA transport pharmacology (Levi et al., 1983; Reynolds and Herschkowitz, 1984; Johnstone et al., 1986), suggesting that GAT-1 may not be restricted to neurons. A failure to recognize and/or distinguish these cell types in many older studies complicates their interpretation.

To gain a better understanding of the contribution of the cloned GABA transporters to neuronal and glial transport systems, we have undertaken a combined pharmacological and molecular biological study using cell cultures derived from rat brain. We first defined the pharmacological profile of the four cloned GABA transporters (ie., GAT-1, GAT-2, GAT-3, and BGT-1), and a related member of this family, the taurine transporter (TAUT; Smith et al., 1992). Next, we examined GABA transport activity in neuronal cultures, and in both Type 1 and O-2A/Type 2 astrocytic cell cultures, and compared their profiles to those of the cloned transporters. Last, we examined these cultures for the presence and relative abundance of mRNA for each of the four GABA transporters and TAUT.

MATERIALS AND METHODS

Materials: [$^3$H]GABA$^2$ ($\approx$90 Ci/mmole) and [$^3$H]taurine (21.9 Ci/mmol) were obtained from New England Nuclear (Boston, Mass.). GABA, taurine, hypotaurine, L-DABA (L-2,4)diaminobutyric acid), poly-D-lysine hydrobromide (average molecular weight, 67,700), ara-C and β-alanine were from Sigma Chemical Corporation (St. Louis, Mo.); guvacine, nipecotic acid, hydroxynipecotic acid, and NNC-711 were from RBI (Natick, Mass.). ACHC (cis-3-aminocyclohexanecarboxylic acid) was provided by Research Biochemical International as part of the Chemical Synthesis Program of the National Institute of Mental Health contract 278-90-0007 (BS). GES was a generous gift of Dr. J. Barry Lombardini (Department of Pharmacology, Texas Tech University). Cell culture media were obtained from Specialty Media (Lavallette, N.J.), and serum was from UBI (Lake Placid, N.Y.). Cell cultures were maintained at 37° C. in a humidified 95% air/5% $CO_2$ atmoshere.

Preparation of primary rat astrocyte cell cultures: Primary glial cultures were established from newborn Sprague-Dawley rat brains. Brains minus cerebella were removed aseptically and carefully dissected free of meninges. A single-cell suspension was made by mincing the brains, then incubating them with 0.25% trypsin/1 mM EDTA for 2-3 minutes. Following inactivation of the trypsin by addition of complete medium (DMEM containing 10% fetal calf serum, 100 U/ml penicillin G, and 100 µg/ml streptomycin sulfate), the cells were allowed to settle and the supernatant decanted; this procedure was then repeated. The cells were dissociated by trituration through a serological pipet. Separate procedures were then used for the preparation of Type-1 and O-2A/Type-2 astrocyte cultures, as will now be described.

For the preparation of Type-1 astrocyte cultures, cells were plated onto uncoated 75 cm$^2$ flasks at low density (1 brain per 10 flasks, or approximately 8×10$^4$ cells/cm$^2$). The medium was changed the following day and twice a week thereafter. After 2–3 weeks the Type 1 astrocytes formed a confluent monolayer, with only minimal contamination of O-2A/Type-2 cells. The cells were then split into 24-well plates (typically, each 75 cm$^2$ flask was split into six 24-well plates) and 1–2 weeks later, transport was measured as described above. Such cultures stained heavily with an anti-GFAP antibody (not shown).

Cultures highly enriched in O-2A/Type-2 cells were prepared from mixed astrocyte cultures which consisted of a monolayer of Type 1 cells upon which rested large numbers of O-2A/Type 2 cells. It had previously been shown that O-2A/Type 2 cells could be purified from such cultures by overnight shaking, which releases the O-2A/Type 2 cells into the medium (McCarthy and DeVellis, 1980). However, we found this method to be impractical for the large numbers of cells required for the present study, and thus sought a more rapid method of isolation. The same brain cell suspensions as described above were plated at high density (1 brain per 75 cm$^2$ flask, or approximately 8×10$^5$ cells/cm$^2$) into flasks coated with poly-D-lysine (10 µg/ml). After 24 hours the medium was replaced and the cultures were subsequently fed twice a week. After 2–3 weeks the cultures consisted of a large number of O-2A/Type-2 cells lying on a monolayer of Type-1 astrocytes. The mixed Type-1 and O-2A/Type-2 astrocyte cultures were washed with PBS, then incubated with trypsin/EDTA for 20–30 seconds with vigorous "smacking"; this technique selectively detached the O-2A/Type-2 cells. Complete medium was added to the flasks and the cell suspension was removed gently, care being taken to not disrupt the underlying Type 1 astrocyte monolayer. The cells were pelleted at low speed, resuspended in complete medium, and added to 24-well plates coated with poly-D-lysine (10 µg/ml). Typically, the cells collected from eight 75 cm$^2$ flasks were added to twelve 24-well plates; increasing the cell density resulted in greater contamination of Type-1 astrocytes. The cells were used for transport assays two days later, by which time about 85% of the cells had extended processes with the typical morphology of O-2A/Type-2 astrocytes; such cells displayed varying intensities of staining with an anti-GFAP antibody (not shown), similar to previous results (Lillien and Raff, 1990). No attempt was made to distinguish or separate O-2A precursors from the more differentiated Type 2 astrocytes.

Preparation of primary rat neuronal cell cultures: Primary neuronal cultures were prepared as described previously (Vaysse et al., 1990). Brains were removed aseptically from E17 embryonic Sprague-Dawley rats brains, carefully dissected free of meninges, and kept on ice. A single-cell suspension was made by mincing the brains, followed by trituration through a serological pipet. The large clumps were allowed to settle, and the supernatant diluted with medium (DMEM/F-12 (1:1) containing 10% fetal calf serum, 100 U/ml penicillin G, 100 µg/ml streptomycin sulfate, 10 µg/ml insulin (porcine or bovine), supplemented with 45 mM KCL), and added to 24-well plates (coated with 10 µg/ml poly-D-lysine) at a density of approximately 2×10$^5$ cells/cm$^2$. On day three cytosine β-D-arabinofuransoside (3 µM) was added to control the proliferation of non-neuronal cells. The cultures were used for transport assay approximately one week after plating.

Transient transfection: Transient transfection was carried out in COS cells as previously described (Smith et al., 1992), with the following modifications. COS cells grown in 75 cm$^2$ or 150 cm$^2$ flasks in DMEM with 10% bovine calf serum, 100 U/ml penicillin G, and 100 µg/ml streptomycin sulfate (37° C., 5% $CO_2$) were transfected using DEAE-dextran. On the day following transfection the cells were split into 24-well assay plates coated with poly-D-lysine (10 µg/ml), and transport was measured 24 hours later.

During the course of this work we noted that compounds typically displayed higher affinity in stable transfections in LM(tk$^-$) cell hosts than in transient transfections in COS cell hosts (L. Borden, unpublished observations). The difference in affinity was typically 3–4-fold, though this varied from clone to clone. Importantly, expression levels did not appear to alter the order of potencies. This phenomenon should be considered when comparing data using different expression systems.

Transport in attached cells: GABA transport by attached cells was measured as described previously (Borden et al., 1992), with the following modifications. Cells grown in 24-well plates (well diameter=18 mm) were washed 3× with HEPES-buffered saline (HBS, in mM: NaCl, 150; HEPES, 20; CaCl$_2$, 1; glucose, 10; KCl, 5; MgCl$_2$, 1; pH 7.4) and allowed to equilibrate on a 37° C. slide warmer. After 10 minutes the medium was removed and unlabeled drugs in HBS were added (450 µl/well). Transport was initiated by adding 50 µl per well of a concentrated solution of [$^3$H] GABA in HBS (final concentration=50 nM). Non-specific uptake was defined in parallel wells with 1 unlabeled GABA (10 mM for Type 1 astrocytes), and was subtracted from total uptake (no competitor) to yield specific uptake; all data represent specific uptake. Plates were incubated at 37° C. for 10 minutes, then washed rapidly 3× with ice-cold HBS, using a 24-position plate washer (Brandel, Gaithersburg, Mass.; model PW-12). Cells were solubilized with 0.05% sodium deoxycholate/0.1N NaOH (0.25 ml/well), an aliquot neutralized with 1N HCl, and radioactivity was determined by scintillation counting. Protein was quantified in an aliquot of the solubilized cells using a BIO-RAD protein assay kit, according to the manufacturer's directions.

Brain Aggregate Preparation: Brain aggregates were prepared as described in Forray and El-Fakahany (1990), with minor modifications. Briefly, adult rat brains were removed from the skull and the cerebral cortex was dissected and placed in ice-cold HBS. The tissue was forced through a nylon mesh bag (200 µm pore; Nitex) followed by passage through a second nylon bag (130 µm pore size; Nitex). The preparation was washed once by centrifugation, then resuspended in HBS.

Transport by brain aggregates: GABA transport by brain aggregates was determined in suspension in 96-well microtiter plates (total incubation volume=250 µl), using an assay similar to that employed for membrane receptor binding (see Zgombick et al., 1991). Briefly, [$^3$H]GABA (final concentration=50 nM) and unlabeled drugs were added to 96-well plates (Corning), and transport was initiated by the addition of brain aggregates. Non-specific uptake was determined with 1 mM unlabeled GABA. The reaction was continued for 10 minutes (37° C.), then terminated by rapid filtration through pre-soaked (0.5% polyethyleneimine) GF/B glass fiber filters, using a Brandel48R cell harvester. The filters were washed with ice-cold HBS, punched into vials, and radioactivity determined by scintillation counting. Protein was determined in an aliquot of the aggregate preparation using the BIO-RAD protein assay kit.

Northern Blot Analysis of Transporter mRNAs: Total cellular RNA was isolated from cultured cells using a modification of the method of Chirgwin et al. (1979). Briefly, cells were rinsed with ice-cold phosphate-buffered saline and lysed in guanidine isothiocyanate (5–10 mls/100 mm plate). Lysates were drawn twice through a 20-gauge needle to shear genomic DNA, and RNA was collected by centrifugation through 5.7M cesium chloride (MacDonald et al., 1987). Rat brain poly A$^+$ RNA was purchased from Clontech (Palo Alto, Calif.). Denatured RNA samples (5–25 µg) were separated by electrophoresis in 1.0% agarose gels containing 2.7% formaldehyde. RNAs were transferred to GeneScreen Plus nylon membranes (Dupont-NEN, Boston, Mass.) by overnight capillary blotting in 10×SSC. Northern blots were rinsed and then baked for 2 hours at 80° C. under vacuum. Prehybridization was for 1–2 hours at 42° C. in a solution containing 50% formamide, 1M sodium chloride, 10% dextran sulfate and 1.0% SDS. Blots were hybridized overnight at 42° C. with $^{32}$P-labeled randomly-primed probes (Prime-It II, Stratagene, La Jolla, Calif.) in prehybridization mixture containing 100 µg/ml sonicated salmon sperm DNA. The blots were washed successively in 2×SSC/2% SDS, 1×SSC/2% SDS, and 0.2×SSC/2% SDS at 65° C., then exposed to Kodak XAR-5 film with one intensifying screen at −80° C. for up to one week.

To facilitate quantitative comparisons of signal intensities between transporters, cDNA fragments of the same size (≈1.5 kb) were prepared as templates for random prime labeling of GAT-1, GAT-2, GAT-3, and TAUT cDNAs, and the specific activity of each probe was determined by TCA precipitation (Sambrook et al., 1989) prior to hybridization. Specific activities ranged from 1.5–2.5×10$^9$ dpm/µg DNA for all probes. Since the cDNA encoding the rat betaine/GABA transporter was not available, an ≈450 bp fragment was generated by PCR (see below), subcloned, sequenced, radiolabeled, and used for hybridization of Northern blots as described. Since this fragment of rBGT-1 is much smaller than the other probes, levels of rBGT-1 transcripts cannot be visually compared with those of GAT-1, GAT-2, GAT-3, and TAUT.

After hybridization with transporter cDNAs, all blots were reprobed for the constitutive mRNA encoding cyclophilin (1B15; Danielson et al., 1988) to confirm that equal amounts of RNA were present in each lane. Cloning a fragment of the rat BGT-1: Primers based on the nucleotide sequence of the mouse betaine/GABA transporter (Lopez-Corcuera et al., 1992; termed "GAT2" by authors) were used to amplify a fragment of rBGT-1 from rat brain CDNA using PCR. The primers represent nucleotides 268–296 (sense) and 715–740 (antisense) of the mouse sequence (Lopez-Corcuera et al., 1992). First strand CDNA was synthesized from rat brain poly A+ RNA using Superscript reverse transcriptase (BRL, Gaithersburg, Md.). PCR amplication was carried out in a buffer containing 10 mM Tris (pH 8.3), 50 mM KCl, 1.5 mM MgCl$_2$, 0.01% gelatin, 0.2 mM each dNTP, 1 µM each primer, Taq polymerase, and either first strand cDNA, RNA, or water for 30 cycles of 94° C./2 min, 60° C./2 min, 72° C./3 min. The ≈450 bp PCR product was separated by agarose gel electrophoresis, isolated on DE81 paper and ligated into pUC18. A portion of the reaction was blotted to a nylon membrane (Zeta-Probe GT; Bio-Rad Laboratories, Richmond, Calif.) and hybridized as described below with a $^{32}$P-labeled oligonucleotide (45 mer) representing the mouse BGT-1 (Lopez-Corcuera et al., 1992) to confirm its identity. Sequence analysis of the subcloned fragment confirmed that it encoded a portion of the rBGT-1; the fragment exhibited 85–94% nucleotide identity and 87–96% amino acid identity with dog, human, and mouse BGT-1 cDNAs, but only 72% nucleotide identity (68% amino acid identity) with the next closest relative, rat GAT-2. This fragment was subsequently reisolated from a single transformant and used in Northern blot hybridizations of rBGT-1 mRNA.

Quantitation of Northern Blots: Autoradiograms were scanned using a Color One Scanner (Apple) and analyzed on an Apple Macintosh computer using Image 1.43 software (NIH). Band intensities were corrected for the amount of mRNA as determined by hybridization to the constitutive mRNA encoding cyclophilin, then normalized to the amount of GAT-1 present in neuronal cultures (for neurons and astrocyte cultures), or the amount of GAT-1 present in brain.

Data Analysis: Competition curves were conducted in duplicate, using 10 concentrations of unlabeled drug. Curves were analysed using software from GraphPad Inplot (San Diego, Calif.). Data were not corrected for the concentration of radioligand since [$^3$H]GABA was employed at a concentration well below its $K_M$; however, since initial rates were not studied, data are presented as IC$_5$. Data represent means±SEM.

RESULTS

Pharmacological characterization of cloned GABA transporters

In an attempt to identify the GABA transporters in neuronal and glial cell cultures, we adopted a two-pronged strategy: comparison of their pharmacological profiles with those of cloned transporters, coupled with mRNA localization. To avoid possible complications resulting from species differences, we used GAT-1, GAT-2, GAT-3 and TAUT cloned from rat brain, the same species from which the neuronal and glial cell cultures were prepared. As the rat BGT-1 transporter had not yet been cloned, we used PCR to isolate a fragment of it for use in Northern blot analysis of mRNA (see Methods). However, since the full-length clone of rat BGT-1 was not available, we chose to study the pharmacologic properties of a human betaine/GABA transporter (hBGT-1) which we recently cloned from a human brain cDNA library (L. A. Borden, K. E. Smith, E. L. Gustafson, T. A. Branchek, and R. L. Weinshank, manuscript submitted).

In our original description of GAT-2 and GAT-3 (Borden et al., 1992) and TAUT (Smith et al., 1992), we examined inhibitors at limited concentrations. We have now conducted an extensive analysis using 11 drugs which are known inhibitors of GABA and/or taurine transport. Full competition curves were obtained for each drug using 50 nM [$^3$H]GABA for the high-affinity GABA transporters (GAT-1, GAT-2, GAT-3, and BGT-1) and 50 nM [$^3$H]taurine for TAUT. The results of these studies are summarized in Table 2.

Under the conditions employed, GABA shows similar affinity at all four cloned GABA transporters (Table 2). GAT-1 is distinguished by high affinity for NNC-711 and ACHC, and low affinity for β-alanine. The rank order of potency is NNC-711>nipecotic acid>GABA>guvacine≧(±)-hydroxynipecotic acid>L-DABA≧ACHC>hypotaurine>β-alanine>GES>taurine. The pharmacologic profile of GAT-1 is quite dissimilar from that of the other cloned transporters as can be seen from Table 3, which shows the correlation of the pIC$_{50}$ (-log IC$_{50}$) values of the various cloned transporters with one another. The most selective GAT-1 compound (NNC-711, 1,000-fold) proved useful in distinguishing GAT-1-mediated GABA transport from that mediated by other GABA transporters in neuronal and glial cultures, and in brain aggregates (see below).

GAT-2 and GAT-3 are pharmacologically similar to one another (r=0.97) but distinct from the other cloned transporters (Table 3). In contrast to GAT-1, GAT-2 and GAT-3 have higher affinity for β-alanine than for ACHC and NNC-711. The order of potency for GAT-2 is GABA>hypotaurine>β-alanine>(±)-nipecotic acid>guvacine>L-DABA>hydroxynipecotic acid>GES>NNC-711>taurine>ACHC, while that for GAT-3 is GABA>hypotaurine>β-alanine>(±)nipecotic acid>guvacine>hydroxynipecotic acid>L-DABA>GES>taurine>ACHC. Hypotaurine, a compound classically described as an inhibitor of taurine transporter, is as potent at GAT-2 and GAT-3 as at TAUT.

The pharmacologic profile of hBGT-1 is distinct from that of the other transporters; a modest correlation is observed with GAT-2 and GAT-3 (r=0.53 and 0.50, respectively; Table 3). The order of potency is GABA>L-DABA>hypotaurine>ACHC>β-alanine>guvacine>(±)-nipecotic acid>NNC-711>hydroxynipecotic acid>GES>taurine. Though none of the drugs tested show selectivity for hBGT-1, a distinguishing feature is the similar potency of β-alanine and ACHC.

We also examined the profile of TAUT using [$^3$H]taurine. The order of potency is hypotaurine=taurine>GES>β-alanine>NNC-711>GABA>guvacine>(±)-nipecotic acid>hydroxynipecotic acid >ACHC>L-DABA. The overall profile correlates poorly with the other transporters (Table 3), though TAUT is similar to GAT-2 and GAT-3 in its preference for β-alanine over ACHC. Importantly, the high affinity for taurine distinguishes TAUT from the other transporters.

Figure 6A:
FIG. 6A. Morphology of neuronal cell cultures. Cultures were prepared as described in Methods. Neuronal cultures were stained with an anti-neurofilament antibody (Boehringer-Mannheim, Indianapolis, Ind.) and visualized with horseradish peroxidase.

Preparation of neuronal and glial cell cultures: To examine GABA transport in neurons and astrocytes, we prepared cell cultures highly enriched in each of these cell types (see Methods). Neuronal cultures were established from E17 embryonic brain and were treated with cytosine β-D-arabinofuranoside to inhibit the proliferation of non-neuronal cells (ie., glia and fibroblasts). After one week in vitro the cultures consisted of highly differentiated neurons displaying an intricate network of processes, which stained positively with an anti-neurofilament antibody (FIG. 6A).

Figure 6B:
FIG. 6B. Morphology of Type 1 astrocyte cell culture. Cultures were prepared as described in Methods. Type 1 astrocyte cultures were stained with cresyl violet.
Figure 6C:
FIG. 6C. Morphology of Type O-2A/Type 2 astrocyte cell culture. Cultures were prepared as described in Methods. Type O-2A/Type 2 astrocyte cultures were stained with cresyl violet.
Figure 7:
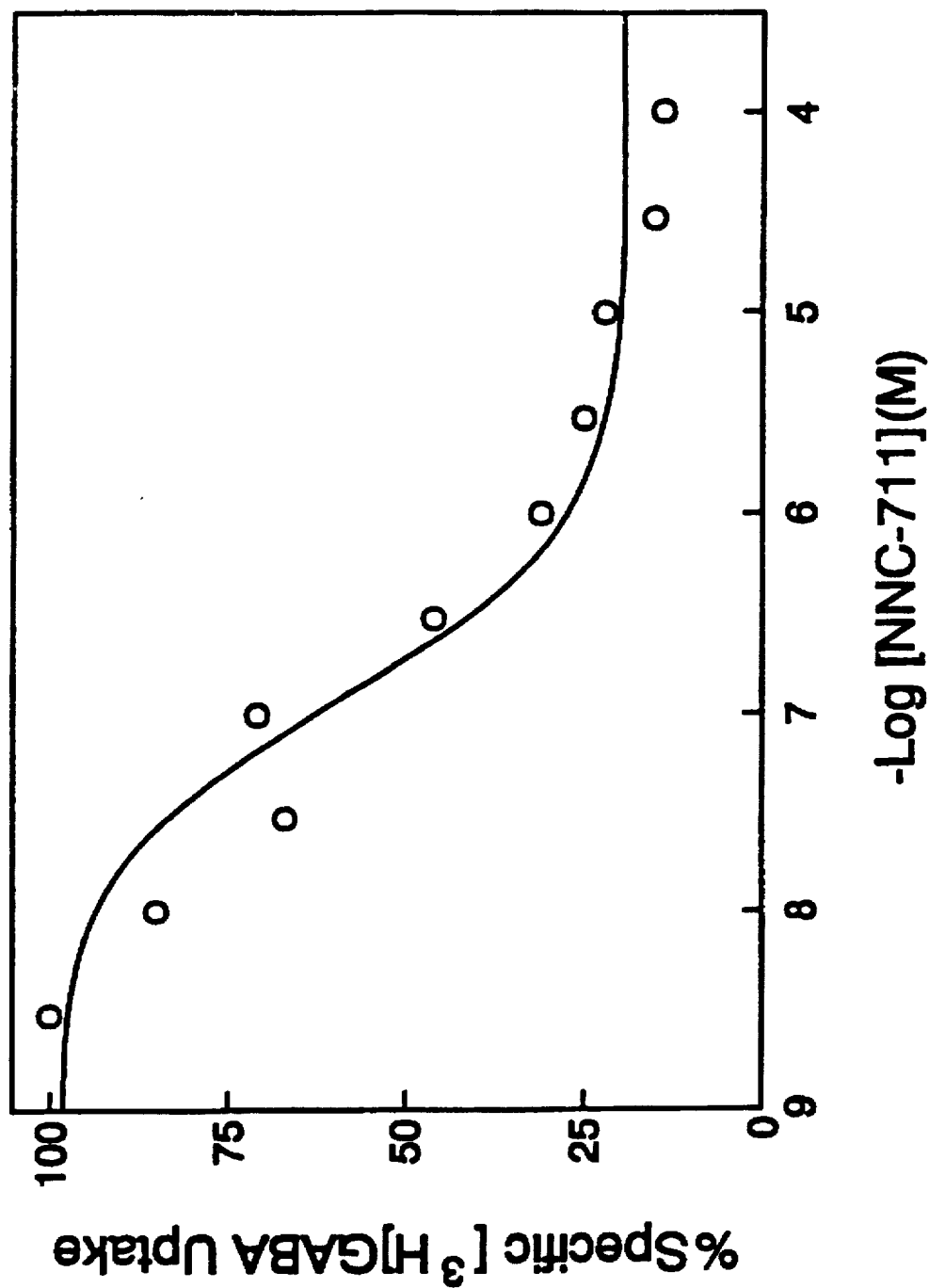
FIG. 7. NNC-711 inhibition of GABA transport in neuronal cultures. Neuronal cultures were incubated with [³H] GABA and the indicated concentrations of NNC-711, as described in Methods. Data show specific uptake, expressed as percent of uptake in the absence of inhibitor. Data are from a single experiment that was repeated at least three times with similar results.

Raff and colleagues have demonstrated that two classes of astrocytes, designated Type 1 and Type 2, can be identified in cell cultures derived from rat optic nerve (Martin et al., 1989; Raff, 1989). These cell types are morphologically and antigenically distinguishable, and are known to arise from distinct precursors (Lillien and Raff, 1990). Type 1 astrocytes are GFAP-positive, flat, cuboidal cells with a large, oval nucleus. In contrast, Type 2 cells are smaller, stellate cells with an eccentric nucleus and multiple processes (Vaysse and Goldman, 1990; Lillien and Raff, 1990). Type 2 cells are derived from an O-2A precursor cell which also gives rise to oligodendrocytes (Raff et al., 1983). Cultures highly enriched in each of these cell types were prepared as described in Methods, and are shown in FIG. 6B (Type 1 astrocytes) and FIG. 6C (O-2A/Type 2 astrocytes). Pharmacological characterization of GABA transporter activity in neuronal cell cultures: Neuronal cultures avidly accumulated [$^3$H]GABA with specific uptake of 42±4 pmoles per mg protein (n=9). Competition curves using unlabeled GABA were consistent with uptake occuring via a single high-affinity site, IC$_{50}$=10±2 μM (n=3). The GAT-1-selective compound NNC-711 was a potent inhibitor (IC$_{50}$≈300 nM) of [$^3$H]GABA uptake but did not inhibit completely the specific uptake even at high concentrations (FIG. 7). When employed at 10 μm, 31±1% (n=6) of the specific uptake persisted. This finding indicates that, under these conditions, about 30% of GABA uptake is mediated via a transporter(s) distinct from GAT-1. To characterize these sites we conducted competition curves in both the absence and presence of 10 μM NNC-711, a concentration sufficient to inhibit transport via GAT-1 almost completely. We used the same 11 drugs used to define the properties of the cloned transporters (Table 2) to allow a direct comparison. As 70% of GABA uptake in neurons is mediated by GAT-1, uptake in the absence of NNC-711 ("NNC-711-sensitive") predominantly reflects transport via this site; in contrast, uptake in the presence of this blocker ("NNC-711-resistant") reflects transport via non-GAT-1 sites. The results of both sets of experiments are shown in Table 4. As expected, GABA transport in the absence of NNC-711 closely resembles the profile of GAT-1: Uptake is sensitive to NNC-711 (see above) and ACHC (IC$_{50}$≈75 M), while β-alanine is a weak inhibitor (IC$_{50}$≈4 mM) (Table 4). The order of potency is NNC-711>GABA>guvacine>(±)-nipecotic acid>hydroxynipecotic acid>ACHC>L-DABA>hypotaurine>GES>β-alanine>taurine, and the profile correlates well with GAT-1 (r=0.99) but poorly with the other transporters (Table 5). These data support the hypothesis that GAT-1 is the predominant GABA transporter in neuronal cultures.

We next examined the affinity of the same drugs in the presence of NNC-711. The affinity of GABA (IC$_{50}$=10 μM) is identical to that observed in the absence of NNC-711 (Table 4), consistent with our observation that GABA uptake in the absence of NNC-711 is well described by a single-site model (see above). Interestingly, the NNC-711-resistant GABA transport is more sensitive to β-alanine (IC$_{50}$≈50 μM) than to ACHC (IC$_{50}$≈2 mM), (Table 3), suggesting that the NNC-711-resistant component is mediated by GAT-2, and/or GAT-3, and/or TAUT. The order of potency is GABA>hypotaurine>β-alanine>(±)-nipecotic acid>guvacine>hydroxynipecotic acid>GES>L-DABA>ACHC>taurine. As shown in Table 5, the highest degree of correlation is with GAT-2 (r=0.87) and GAT-3 (r=0.904). The correlation with hBGT-1 is modest (r=0.69), weaker with GAT-1, and poorest with TAUT. The contribution of these transporters was explored further by Northern blot analysis of neuronal mRNA (see below).

Pharmacological characterization of GABA transporter activity in glial cell cultures: GABA transport was examined separately in Type 1 and O-2A/Type 2 astrocyte cultures.

GABA transport in Type 1 cultures was low, averaging only 1.4±0.3 pmoles/mg protein (n=10), which is about 3% of the uptake observed in neuronal cultures. The order of potency is guvacine>taurine>hypotaurine>β-alanine>GABA>GES> (±)-nipecotic acid>ACHC>hydroxynipecotic acid>NNC-711>L-DABA (Table 4). The finding that GABA is a weak inhibitor ($IC_{50}$≈300 µM) whereas taurine is a potent inhibitor ($IC_{50}$≈50 µM) suggests that GABA uptake in Type 1 astrocytes is mediated by TAUT. Consistent with this idea, the pharmacologic profile correlates most closely with TAUT, although the correlation is only modest (r=0.52); a poor correlation is observed with the other transporters (Table 5).

Unlike Type 1 astrocytes, O-2A/Type 2 astrocytes avidly accumulate [$^3$H]GABA (38±4 pmoles/mg protein; n=7) with high affinity ($IC_{50}$≈4 µM, Table 4). NNC-711 is a potent inhibitor of GABA uptake ($IC_{50}$≈70 nM), but 26±4% (n=7) of the specific uptake persisted in the presence of 10 µM NNC-711 (FIG. 7), similar to the situation in neurons. Accordingly, we examined the pharmacological profile of O-2A/Type 2 astrocytes both in the absence and presence of 10 M NNC-711.

GABA transport in O-2A/Type 2 astrocytes, in the absence of NNC-711, displays high-affinity for NNC-711 ($IC_{50}$≈70 nM) and ACHC ($IC_{50}$≈35 µM), and low-affinity for β-alanine ($IC_{50}$≈2 µM) (Table 4). The order of potency is NNC-711>GABA>guvacine>(±)-nipecotic acid>hydroxynipecotic acid>ACHC>L-DABA>hypotaurine>GES>β-alanine>taurine, and there is an excellent correlation with GAT-1 (r=0.99, Table 5). Thus, in O-2A/Type 2 astrocytes, as in neurons, the majority of GABA transport is mediated via GAT-1.

GABA transport in O-2A/Type 2 astrocytes in the presence of 10 µM NNC-711 displays high-affinity for GABA ($IC_{50}$≈2 µM) and is more sensitive to β-alanine ($IC_{50}$≈25 µM) than to ACHC ($IC_{50}$≈2 mM) (Table 4). The order of potency is GABA>β-alanine>hypotaurine>(±)-nipecotic acid>guvacine>L-DABA>hydroxynipecotic acid>taurine>GES>ACHC, and the data correlate best with GAT-2 (r=0.96) and GAT-3 (r=0.94) (Table 5). The correlation is modest with hBGT-1 (r=0.69), and poor with both GAT-1 and TAUT (<0.25; Table 5). To gain further information regarding the contribution of these transporters, we analysed cultures for the presence of transporter mRNA (see below).

Pharmacological characterization of GABA transporter activity in brain aggregates: To examine GABA transport in freshly isolated rat brain, we employed a suspension assay utilizing dissociated brain aggregates. An advantage of this technique is that, unlike purification techniques which yield selective enrichment of various cell types, the brain aggregates include all the cellular elements in the brain in their original proportions.

Figure 8:
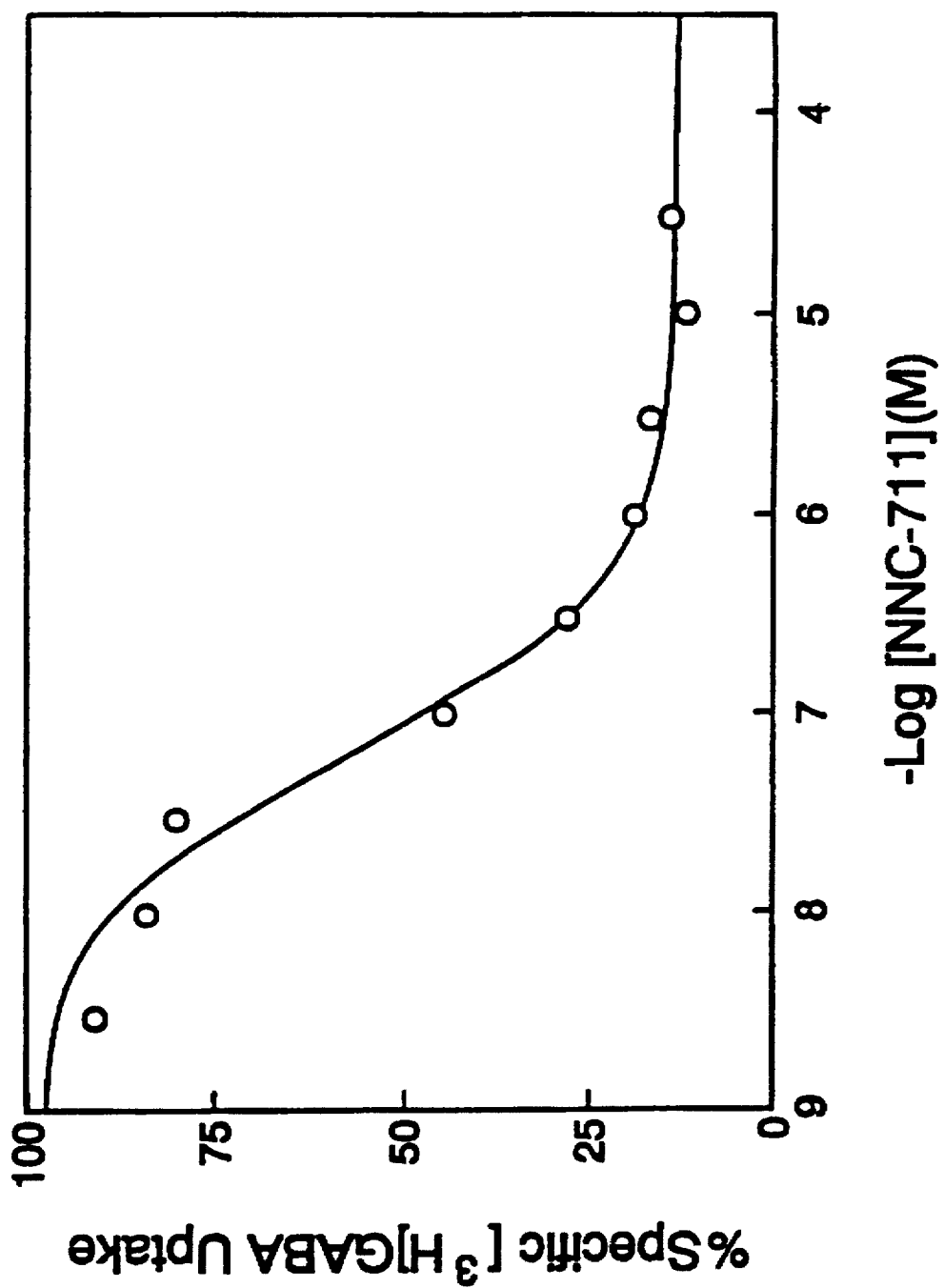
FIG. 8. NNC-711 inhibition of GABA transport in O-2A/Type 2 astrocytic cultures. O-2A/Type 2 astrocytic culturs were incubated with [³H]GABA and the indicated concentrations of NNC-711, as described in Methods. Data show specific uptake, expressed as percent of uptake in the absence of inhibitor. Data are the mean of three experiments.
Figure 10A:
FIGS. 10A–10J Localization of GABA transporter mRNAs.
Figure 10F:
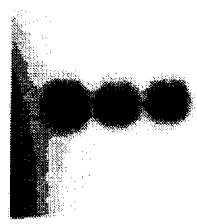
Figure 10B:
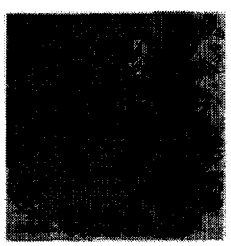
Figure 10G:
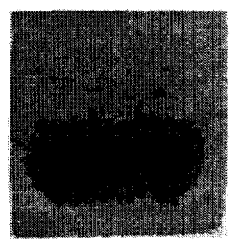
Figure 10C:
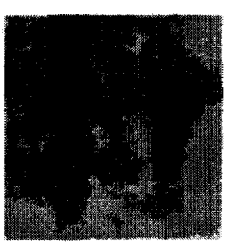
Figure 10H:
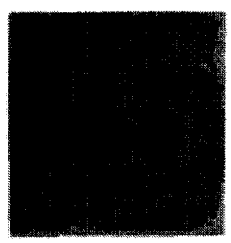
Figure 10D:
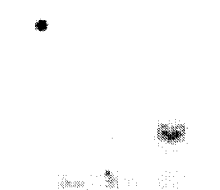
Figure 10I:
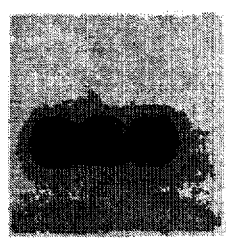
Figure 10E:
Figure 10J:
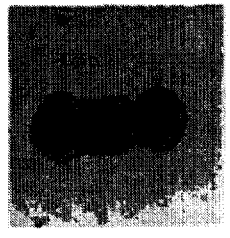

Rat brain aggregates avidly transport [$^3$H]GABA (83±12 pmoles/mg protein, n=9) with high affinity ($IC_{50}$≈10 µM; Table 6). NNC-711 is a potent inhibitor of GABA uptake ($IC_{50}$=90 nM), although 15±2% (n=3) of the uptake persists in the presence of a high concentration (10 µM) of this drug (FIG. 8). Accordingly, we examined the pharmacological profile of brain aggregates both in the absence and presence of 10 µM NNC-711.

In the absence of NNC-711, ACHC ($IC_{50}$=31 µM) is more potent than β-alanine ($IC_{50}$≈3 mM; Table 6). The order of potency is NNC-711>(±)-nipecotic acid>GABA=guvacine=hydroxynipecotic acid>L-DABA>ACHC>hypotaurine>GES>β-alanine>taurine, and there is an excellent correlation with GAT-1 (r=0.99) (Table 7). The NNC-711-resistant component of transport has high affinity for β-alanine ($IC_{50}$=33 µM) and low affinity for ACHC ($IC_{50}$≈2.5 mM). The order of potency is GABA>guvacine>hypotaurine>β-alanine>(±)-nipecotic acid>hydroxynipecotic acid>L-DABA>NNC-711>GES>taurine>ACHC (Table 6), and the data correlate best with GAT-2 and GAT-3 (r=0.96 and 0.95, respectively) (Table 7).

Localization of mRNA: We next employed Northern blot analysis to examine the distribution of transporter mRNA in neuronal and glial cultures and in total brain. Probes for GAT-1, GAT-2, GAT-3 and TAUT were labeled to similar specific activities to allow a direct comparison, and Northern blots were reprobed for 1B15 (cyclophilin) for the purpose of normalization; however, as only a fragment of rBGT-1 was available the data obtained with this probe can be compared only semi-quantitatively to the other transporters (see Methods). Representative Northern blots are shown in FIG. 10 and the data are quantified in Table 8. As expected from the pharmacology, GAT-1 mRNA is abundant in neurons, whereas Northern blots failed to detect GAT-2 mRNA in neuronal cultures. GAT-3 mRNA is also present in neuronal cultures but the levels are about one third those of neurons. mRNA for rBGT-1 is not detected by densitometry in neuronal cultures, though visual inspection of the autoradiograms sometimes reveals the presence of a faint band. TAUT mRNA is present at levels about 1.5-fold higher than GAT-1.

In Type 1 astrocyte cultures, mRNAs for GAT-1, GAT-2, and GAT-3 are not detectable by Northern blot analysis (FIGS. 10A–10J, and Table 8). In contrast, mRNAs for rBGT-1 and TAUT are fairly abundant.

Levels of transporter mRNA expression in O-2A/Type 2 astrocytes are more variable than in the other cell types. GAT-1 mRNA was abundant in these cultures (FIGS. 10A–10J, Table 8), with levels approximately half those in neurons. GAT-2 mRNA is the most abundant GABA transporter with levels approximately 4-fold greater than GAT-1 mRNA. GAT-3 mRNA is present at levels about half those of GAT-1. mRNA for rBGT-1 and TAUT are also present in O-2A/Type 2 astrocytes, at levels similar to that of GAT-1. Thus, O-2A/Type 2 cultures contain all the known GABA transporters.

In summary, GAT-1 mRNA is present in neurons and O-2A/Type 2 astrocytes, as is GAT-3. GAT-2 mRNA is present in O-2A/Type 2 astrocytes, but not in neurons or Type 1 astrocytes. Type 1 astrocytes also lack GAT-1 and GAT-3. rBGT-1 mRNA is present in Type 1 and O-2A/Type 2 astrocyte cultures, but is rarely observed in neurons, and then at low levels. TAUT mRNA is present in all cell types examined, with the highest abundance in Type 1 astrocytes.

Using poly A$^+$ RNA from total rat brain, all four high-affinity GABA transporters, and TAUT, were detected by Northern blots (not shown). GAT-1 and GAT-3 mRNAs were both quite abundant, while the levels of GAT-2 mRNA were about 20% of GAT-1 (Table 8). In contrast, BGT-1 and TAUT mRNA were relatively scarce, with levels ≈10% those of GAT-1 mRNA (Table 8).

TABLE 2

Pharmacological profile of cloned GABA and taurine transporters. Data show the $IC_{50}$ (in µM) for inhibition of [$^3$H] GABA uptake (GAT-1, GAT-2, GAT-3 hBGT-1) or [$^3$H] taurine uptake (TAUT) at the indicated cloned transporters. Values represent means ± SEM of at least three experiments.

| Clone/ drug | $IC_{50}$, µM | | | | |
|---|---|---|---|---|---|
| | rGAT-1 | rGAT-2 | rGAT-3 | hBGT-1 | TAUT |
| GABA | 30 ± 8 | 17 ± 6 | 33 ± 10 | 42 ± 12 | 720 ± 170 |
| ACHC | 132 ± 44 | 25,900 ± 12,600 | 55,100 ± 25,000 | 1,070 ± 508 | 9,230 ± 2,620 |

TABLE 2-continued

Pharmacological profile of cloned GABA and taurine transporters. Data show the $IC_{50}$ (in μM) for inhibition of [$^3$H] GABA uptake (GAT-1, GAT-2, GAT-3 hBGT-1) or [$^3$H] taurine uptake (TAUT) at the indicated cloned transporters. Values represent means ± SEM of at least three experiments.

| Clone/ drug | $IC_{50}$, μM | | | | |
|---|---|---|---|---|---|
| | rGAT-1 | rGAT-2 | rGAT-3 | hBGT-1 | TAUT |
| guvacine | 39 ± 6 | 228 ± 38 | 378 ± 18 | 1,420 ± 201 | 1,030 ± 213 |
| hydroxy-nipecotic | 44 ± 8 | 567 ± 50 | 467 ± 53 | 3,840 ± 688 | 4,810 ± 653 |
| (±)-nipecotic acid | 24 ± 6 | 113 ± 33 | 159 ± 30 | 2,350 ± 253 | 2,030 ± 429 |
| NNC-711 | 0.38 ± 0.07 | 729 ± 319 | 349 ± 151 | 3,570 ± 1,140 | 207 ± 59 |
| hypotaurine | 1,010 ± 135 | 52 ± 6 | 73 ± 7 | 536 ± 41 | 47 ± 5 |
| β-alanine | 2,920 ± 197 | 66 ± 9 | 110 ± 40 | 1,100 ± 66 | 176 ± 34 |
| GES | 4,840 ± 1,200 | 696 ± 110 | 915 ± 49 | 4,800 ± 910 | 129 ± 34 |
| L-DABA | 128 ± 12 | 300 ± 51 | 710 ± 237 | 528 ± 62 | 41,800 ± 29,100 |
| taurine | 32,300 ± 12,000 | 1,270 ± 40 | 2,860 ± 358 | 13,200 ± 1250 | 48 ± 11 |

TABLE 3

Correlation of GABA transport activity of cloned transporters. The $pIC_{50}$ values for inhibition of [$^3$H] GABA uptake (GAT-1, GAT-2, GAT-3, hBGT-1) or [$^3$H] taurine uptake (TAUT) at each of the cloned transporters was correlated with the values at the other transporters (data from Table 2). Data represent r values.

| clone | rGAT-1 | rGAT-2 | rGAT-3 | hBGT-1 |
|---|---|---|---|---|
| rGAT-2 | −0.07 | | | |
| rGAT-3 | 0.22 | 0.97 | | |
| hBGT-1 | 0.27 | 0.53 | 0.50 | |
| TAUT | −0.41 | 0.26 | 0.28 | −0.26 |

TABLE 4

Pharmacological profile of GABA transport in rat neuronal and glial cell cultures. Data show the $IC_{50}$ (in μM) for inhibition of [$^3$H] GABA uptake in neuronal and glial cultures, in the absence and presence of NNC-711. Values represent means ± SEM of at least three experiments.

| assay condtion/ drug | Neurons | Neurons with NNC-711[1] | Type 1 astrocytes | O-2A/ Type 2 astrocytes | O-2A/ Type 2 astrocytes with NNC-711[1] |
|---|---|---|---|---|---|
| GABA | 10 ± 2 | 10 ± 1 | 294 ± 100 | 4 ± 0.2 | 2 ± 0.4 |
| ACHC | 77 ± 8 | 1,950 ± 1,000 | 400 ± 200 | 35 ± 4 | 2,360 ± 500 |
| guvacine | 14 ± 2 | 136 ± 45 | 23 ± 10 | 8 ± 0.9 | 81 ± 30 |
| hydroxy-nipecotic acid | 22 ± 2 | 304 ± 100 | 1,610 ± 500 | 17 ± 3 | 197 ± 20 |
| (±)-nipecotic acid | 18 ± 5 | 119 ± 20 | 315 ± 100 | 12 ± 2 | 61 ± 20 |
| NNC-711 | 0.28 ± 0.1 | ND[2] | 2 ± 0.3 | 0.07 ± 0.01 | ND |
| hypotaurine | 742 ± | 25 ± 2 | 69 ± 30 | 620 ± | 29 ± 15 |

TABLE 4-continued

Pharmacological profile of GABA transport in rat neuronal and glial cell cultures. Data show the $IC_{50}$ (in μM) for inhibition of [$^3$H] GABA uptake in neuronal and glial cultures, in the absence and presence of NNC-711. Values represent means ± SEM of at least three experiments.

| assay condtion/ drug | Neurons | Neurons with NNC-711[1] | Type 1 astrocytes | O-2A/ Type 2 astrocytes | O-2A/ Type 2 astrocytes with NNC-711[1] |
|---|---|---|---|---|---|
| | | 200 | | 200 | |
| β-alanine | 4,060 ± 2,000 | 48 ± 10 | 100 ± 30 | 2,030 ± 300 | 24 ± 8 |
| GES | 2,110 ± 600 | 508 ± 60 | 310 ± 60 | 1,560 ± 300 | 603 ± 300 |
| L-DABA | 165 ± 20 | 861 ± 225 | 3,400 ± 2,000 | 74 ± 10 | 91 ± 30 |
| taurine | 8,300 ± 3,000 | 2,490 ± 900 | 47 ± 10 | 13,000 ± 6,000 | 328 ± 200 |

[1] determined in the presence of 10 μM NNC-711
[2] not determined

TABLE 5

Correlation of GABA transport activity in neuronal and astrocyte cultures with cloned GABA and taurine transporters. The $pIC_{50}$ values for inhibition of [$^3$H] GABA transport in neuronal and astrocyte cultures (from Table 4) were correlated with the $pIC_{50}$ values at each of the cloned transporters (data from Table 2). Data represent r values.

| clone/ assay condition | GAT-1 | GAT-2 | GAT-3 | hBGT-1 | TAUT |
|---|---|---|---|---|---|
| neurons | 0.99 | 0.04 | 0.19 | 0.20 | −0.35 |
| neurons with NNC-711 | 0.36 | 0.87 | 0.90 | 0.69 | 0.24 |
| Type 1 astrocytes | 0.29 | −0.12 | −0.02 | −0.16 | 0.52 |
| O-2A/Type 2 astrocytes | 0.99 | 0.7 | 0.22 | 0.30 | −0.35 |
| O-24A/Type 2 astrocytes with NNC-711 | 0.24 | 0.96 | 0.94 | 0.69 | 0.25 |

TABLE 6

Pharmacological profile of GABA transport in rat brain aggregates. Data show the $IC_{50}$ (in μM) for inhibition of [$^3$H] GABA uptake. Values represent means ± SEM of at least three experiments.

| assay condition/ drug | $IC_{50}$, μM | |
|---|---|---|
| | control | with NNC-711[1] |
| GABA | 10 ± 2 | 4 ± 0.8 |
| ACHC | 31 ± 4 | 2,590 ± 600 |
| guvacine | 10 ± 2 | 97 ± 30 |
| hydroxy-nipecotic acid | 10 ± 1 | 69 ± 10 |
| (±)-nipecotic acid | 7 ± 0.8 | 48 ± 10 |
| NNC-711 | 0.09 ± 0.01 | 323 ± 70 |
| hypotaurine | 692 ± 100 | 25 ± 10 |

TABLE 6-continued

Pharmacological profile of GABA transport in rat brain aggregates. Data show the $IC_{50}$ (in μM) for inhibition of [$^3$H] GABA uptake. Values represent means ± SEM of at least three experiments.

| assay | $IC_{50}$, μM | |
|---|---|---|
| condition/ drug | control | with NNC-711[1] |
| β-alanine | 2,930 ± 500 | 33 ± 8 |
| GES | 1,340 ± 100 | 410 ± 100 |
| L-DABA | 22 ± 3 | 144 ± 30 |
| taurine | 64,000 ± 20,000 | 730 ± 200 |

[1]determined in the presence of 10 μM NNC-711

TABLE 7

Correlation of GABA transport activity in rat brain aggregates with cloned GABA and taurine transporters. The $pIC_{50}$ values for inhibition of GABA transport in brain aggregates (data from Table 6) were correlated with the $pIC_{50}$ values at each of the cloned transporters (data from Table 2). Data represent r values.

| clone assay condition | GAT-1 | GAT-2 | GAT-3 | hBGT-1 | TAUT |
|---|---|---|---|---|---|
| control | 0.99 | 0.03 | 0.19 | 0.28 | −0.50 |
| 10 μM NNC-711 | 0.13 | 0.96 | 0.95 | 0.63 | 0.13 |

TABLE 8

Quantitation of GABA transporter mRNA localization. Autoradiograms of Northern blots (such as those shown in FIG. 10) were quantitated by densitometry, then corrected for the amount of mRNA as determined by hybridazation to the constitutive mRNA encoding cyclophilin. Data are expressed as a fraction of GAT-1 mRNA present in neuronal cultures (for cell cultures), or total brain. Data for neurons, Type 1 astrocytes, and O-2/Type 2 astrocytes are means of 3 or 4 independent platings, assayed on separate gels.

| cell culture/ clone | Neurons | Type 1 astrocytes | O-2A/Type 2 astrocytes | brain |
|---|---|---|---|---|
| GAT-1 | 1[1] | 0 | 0.4 | 1[1] |
| GAT-2 | 0 | 0 | 1.7 | 0.2 |
| GAT-3 | 0.3 | 0 | 0.2 | 1.2 |
| BGT-1[2] | 0 | 0.6 | 0.3 | 0.1 |
| TAUT | 1.6 | 2.2 | 0.6 | 0.1 |

[1]by definition
[2]The specific activity of the rat BGT-1 probe was lower than that of the other probes (see Methods), thus the data underestimate the actual abundance

DISCUSSION

The application of molecular biology to the study of GABA transporters has provided considerable insight into this important class of synaptic proteins, but has also raised a number of questions. For example, it has not been clear which transporters are expressed in neurons and which in glia, nor what role each plays in regulating synaptic transmission. Particularly confusing is the apparent lack of correspondence between the newly cloned transporters and the classically described glial transport systems (see Introduction). In an attempt to resolve these issues we have combined pharmacological studies with mRNA localization, employing primary cultures of neurons, and Type 1 and O-2A/Type 2 astrocytes. The results for each of these cell types will be discussed individually.

As expected from earlier studies, the majority of GABA transport activity in neuronal cultures has the properties of GAT-1, most notably high affinity for NNC-711 and ACHC, and low affinity for β-alanine. Consistent with these pharmacological results, we found that GAT-1 mRNA was abundant in neuronal cultures. These results are also consistent with in situ hybridization studies which demonstrate that GAT-1 mRNA is abundant in many GABAergic neurons in the rat brain (Rattray and Priestley 1993; M. M. Durkin, E. L. Gustafson, K. E. Smith, L. A. Borden, P. R. Hartig, R. L. Weinshank, and T. A. Branchek, manuscript submitted).

Interestingly, we observed that in neuronal cultures approximately 30% of GABA uptake is mediated by a non-GAT-1 mechanism, a finding not recognized by earlier investigators. The pharmacologic profile of this activity correlated well with GAT-2 and GAT-3, whose profiles are similar. However, Northern blot analysis revealed the presence in these cultures of mRNA for GAT-3 but not GAT-2, suggesting that GAT-3 mediates the uptake. The correlation with BGT-1 (r=0.687) was only slightly better than the correlation between GAT-3 and BGT-1 (0.503), suggesting that rBGT-1 makes only a minor contribution to the observed GABA transport. Consistent with this hypothesis, rBGT-1 mRNA was either absent, or present at very low levels in neuronal cultures. A role for GAT-3 in neuronal cultures is consistent with in situ hybridization studies which demonstrate that GAT-3 mRNA is present in rat brain neurons (Clark et al., 1992; M. M. Durkin, E. L. Gustafson, K. E. Smith, L. A. Borden, P. R. Hartig, R. L. Weinshank, and T. A. Branchek, unpublished observations), though it is less abundant than GAT-1. Taken together, these data indicate clearly that neuronal GABA transport is heterogeneous, though it is not yet known whether both GABA transporters are expressed in individual neurons.

In contrast to neurons, Type 1 astrocytes transport only low levels of GABA and the transport is sensitive to β-alanine, in agreement with earlier autoradiographic studies (Reynolds and Herschkowitz, 1984). However, we found that the transport activity had low affinity for GABA and high affinity for taurine, suggesting that uptake is mediated by TAUT. It is interesting that we have recently observed similar results with a variety of glial cell lines (L. A. Borden, unpublished observations). Northern blots of Type 1 astrocytes demonstrated the presence of mRNA for TAUT and rBGT-1, but the absence of mRNA for GAT-1, GAT-2, and GAT-3. GABA transport activity correlated best with TAUT, though the correlation was only modest (r=0.523). There was essentially no correlation with BGT-1, despite the relative abundance of rBGT-1 mRNA.

This discrepancy might reflect pharmacologic differences between rat and human BGT-1, as we have observed between human, mouse, and dog BGT-1 (L. A. Borden, K. E. Smith, E. L. Gustafson, T. A. Branchek, and R. L. Weinshank, unpublished observations); confirmation of this issue must await cloning of a full length cDNA for rBGT-1. Alternatively, we cannot rule out the existence in Type 1 astrocytes of an as-yet uncloned transporter. None-the-less, the low level of [$^3$H]GABA transport in Type 1 astrocytes, and the low affinity for GABA, suggest that BGT-1 makes little contribution to GABA transport in these cells, despite the presence of rBGT-1 mRNA. It is possible that this discrepancy is an artifact of cell culture and that BGT-1 is expressed at high levels in vivo. A similar phenomenon has been reported in GH3 cells which have been shown to produce mRNA for the dopamine D2 receptor, although receptor binding is not detectable (Missale et al., 1991).

GABA transport in O-2A/Type 2 astrocytes differed considerably from that in Type 1 astrocytes, as expected from earlier autoradiographical studies. Previous investigations of GABA transport in astrocytes of the O-2A/Type 2 revealed these cells to have a "neuronal-like" pharmacology, based on their sensitivity to ACHC and insensitivity to β-alanine (Levi et al., 1983; Reynolds and Herschkowitz, 1984; Johnstone et al., 1986). However, precise interpretation of these data was complicated by the use of single concentrations of inhibitor and the qualitative nature of the assay (Reynolds and Herschkowitz, 1984; Johnstone et al., 1986), or the use of mixed astrocyte cultures (Levi et al., 1983). Our combined pharmacological and mRNA analyses establish unequivocally not only that GAT-1 is present in O-2A/Type 2 astrocyte cultures but that it is abundant in these cells, as it is in neurons. These results are in agreement with those of Mabjeesh et al. (1992) who observed GAT-1-like immunoreactivity in cultured astrocytes with an O-2A/Type 2 morphology. Importantly, the data are also consistent with those of Radian et al. (1990), who observed GAT-1 immunoreactivity in glial processes in sections of rat brain.

We also observed that approximately 25% of GABA transport in O-2A/Type 2 astrocytes was resistant to NNC-711 and was thus mediated by a transporter distinct from GAT-1. The pharmacological profile correlated best with GAT-2 and GAT-3, and Northern blots revealed the presence in these cells of mRNA for both of these transporters. The levels of GAT-2 mRNA were greater than those for GAT-1, whereas GAT-3 mRNA was present at lower levels. Thus, despite quantitative differences, there is qualitative agreement between the pharmacology and mRNA localization. mRNA for rBGT-1 was also fairly abundant though the correlation with hBGT-1 (r=0.685) was only slightly greater than would be expected were the transport activity mediated solely by GAT-2 and/or GAT-3 (see Table 3). Taken together, the data suggest that the NNC-711-resistant uptake in O-2A/Type 2 astrocytes is mediated primarily by GAT-2 though GAT-3 and to a lesser extent rBGT-1, may also contribute. It is interesting to note that O-2A/Type 2 astrocytes exhibit the greatest heterogeneity in expression of GABA transporters, with all five present.

In brain aggregates, 85% of GABA uptake has a GAT-1-like pharmacology and GAT-1 mRNA is abundant. mRNA for GAT-2, GAT-3, and BGT-1 are all present though suprisingly, these transporters together account for approximately 15% of total GABA transport, thus suggesting a mismatch between protein and mRNA levels. Previous autoradiographic studies in which brain slices were incubated with [³H]GABA suggested that glial cells make only a minor contribution to overall GABA uptake in vivo (Iversen and Bloom, 1972; Martin, 1976). This is consistent with our finding of low GABA uptake in Type 1 astrocytes but is in contrast to O-2A/Type 2 astrocytes, which avidly accumulate GABA. However, it has been suggested (Marritott and Wilkin, 1993) that Type 2 astrocytes cotrespond to reactive astrocytes which proliferate in response to brain injury, but which are rare in the normal (i.e., non-injured) brain. A similar situation has been demonstrated for nerve growth factor mRNA which is not present in adult glia, but whose expression is high during development and following injury, as well as in actively growing astrocytes in vitro (Lu et al., 1991). The hypothesis that glial cells make only a minor contribution to GABA uptake in vivo is supported by in situ hybridization studies of transporter mRNAs which reveal little (M. M. Durkin, E. L. Gustafson, K. E. Smith, L.A. Borden, P. R. Hartig, R. L. Weinshank, and T. A. Branchek, unpublished observations) or no labeling in glial cells (Rattray and Priestley, 1993; Clark et al., 1992), despite heavy labeling in many populations of neurons. It is possible that GABA transporter mRNAs are present in glial cells but at low copy numbers, which are below the limits of detection by in situ hybridization. Amplification of the signal by in situ PCR may be required to visualize these transporters in glial cells. Alternatively, the apparent absence of GABA transporter mRNA in glial cells may be a technical problem relating to the small size of glial cells, since silver grains are more readily observed in large cells. It is clear that further experiments are required to resolve this critical issue.

Numerous animal studies (reviewed in Krogsgaard-Larsen et al., 1987) and more recently, clinical studies with human patients (Chadwick et al., 1991), indicate that inhibitors of GABA transport possess anti-convulsive activity, presumably by increasing GABAergic transmission. It has been argued that glial transporters are the preferred target since inhibition of neuronal transport would be expected to result in depletion of GABA in the nerve terminal; the net effect of this depletion would be an eventual decrease in GABAergic transmission (Krogsgaard-Larsen et al., 1987). However, the findings that 1. GAT-1 is not restricted to neurons; 2. neuronal transport appears to predominate over glial transport; and 3. β-alanine-sensitive transporters are observed in neurons, as well as glia, suggest a re-evaluation of the role of neuronal and glial transporters in the treatment of convulsive disorders. It should be emphasized that the presence of GAT-1 in neurons and glia precludes the development of a glial- (or neuronal) selective drug directed towards this site.

In conclusion, we have utilized a combined pharmacological and molecular biological approach to re-examine GABA transport in neuronal and glial cell cultures. The salient points of these studies may be summarized as follows: 1. GAT-1 mRNA is present in both neurons and O-2A/Type 2 astrocytes, and appears to account for the majority of GABA transport in both cell types; 2. GAT-3 mRNA is observed in neurons and O-2A/Type 2 astrocytes, though at levels below those of GAT-1 or GAT-2; 3. GAT-2 mRNA is present in O-2A/Type 2 cells, but is not detectable (by Northern blots) in neurons; 4. Type 1 astrocytes exhibit very low levels of GABA transport, and this activity has low affinity for GABA but high affinity for taurine. mRNAs for TAUT and BGT-1 are present in these cultures, whereas those for GAT-1, GAT-2 and GAT-3 are not detected. 5. the pharmacologic data in glial cells can be explained by the presence of various combinations of the known cloned transporters, and no evidence was obtained for the existence of the classical "glial transporter". These findings provide new insight into the regulation of GABAergic transmission in the central nervous system and should aid in the development of novel therapeutic agents acting at GABA transporters.

Determination of Tiagabine, SK&F 89976-A, CI-966, and NNC-711 Selectivity for the Cloned GABA Transporters GAT-1, GAT-2, GAT-3 and hBGT-1.

γ-Aminobutyric acid (GABA) is the major inhibitory neurotransmitter in the mammalian central nervous system. Drugs that modulate GABAergic activity, such as the benzodiazepines and barbiturates, are efficacious in the treatment of a variety of neuropsychiatric disorders, in particular epilepsy and anxiety (Twyman and Macdonald, 1991; Goodchild, 1993).

Following its release into the synapse, GABA is rapidly transported into presynaptic terminals and surrounding astroglial cells by high-affinity, sodium-dependent transporters; this process aids in the termination of GABA action and also prevents the spread of neurotransmitter, thereby assuring the fidelity of neurotransmission (for reviews see Krogsgaard-Larsen et al., 1987; Kanner and Schuldiner, 1987). Pharmacologic inhibition of uptake provides a novel mechanism for sustaining levels of neurotransmitter in the synapse and thereby increasing synaptic transmission.

Determining the efficacy of GABA transport inhibitors such as nipecotic acid in vivo has been hampered by their poor penetration of the blood-brain barrier, a property attributable to their high degree of hydrophilicity. In an effort to overcome this problem, Ali et al. (1985) examined the effect of adding lipophilic side chains to the nitrogen atom of various GABA transport blockers. Surprisingly, the addition of 4,4-diphenyl-3-butenyl side chains to nipecotic acid and guvacine (SK&F 89976-A and SK&F 100330-A, respectively) resulted in a 20-fold increase in potency, when tested in brain synaptosomes. Since the original report, a number of other groups have synthesized similar derivatives such as CI-966 (Bjorge et al., 1990) and Tiagabine (Andersen et al., 1993). Importantly, these compounds all display anticonvulsive activity in laboratory animals (Yunger et al., 1984; Swinyard et al., 1991; Nielsen et al., 1991; Taylor et al., 1990; Suzdak et al., 1992).

Determining the site of action of the lipophilic GABA transport inhibitors is essential to understanding their mechanism of action, but is complicated by the heterogeneity of GABA transport. Early studies with cell culture systems suggested the existence of distinct neuronal and glial GABA transport systems (reviewed in Krogsgaard-Larsen et al., 1987). More recently, molecular cloning has identified four distinct GABA transporters termed GAT-1 (Guastella et al., 1990), GAT-2 (Borden et al., 1992), GAT-3 (Borden et al., 1992), and BGT-1, the latter transporting both GABA and the osmolyte betaine (Yamauchi et al., 1992). A clone identical to GAT-3 was described by Clark et al. (1992) and termed GAT-B. Clones for all four GABA transporters have been identified in mice (Liu et al., 1993), though a different terminology was employed: mouse GAT-1 is the homologue of rat GAT-1; mouse GAT-2 is the homologue of BGT-1; mouse GAT-3 is the homologue of rat GAT-2; and mouse GAT-4 is the homologue of rat GAT-3.

In the present report, we have examined the potency of four lipophilic transport inhibitors at each of the four cloned GABA transporters. We find that they all show a high degree of selectivity for GAT-1, indicating that their anticonvulsive activity is mediated via inhibition of GABA transport by this site. This information should be useful in understanding the role of GABA in brain function and in the design of novel transport inhibitors.

2. MATERIAL AND METHODS

2.1 Materials

[$^3$H]GABA (98.9 Ci/mmole) was obtained from New England Nuclear (Boston, Mass.). GABA was from Sigma Chemical Corporation (St. Louis, Mo.); (R,S)-nipecotic acid, guvacine, and NNC-711 were from Research Biochemical Incorporated (Natick, Mass.). CI-966 (Bjorge et al., 1990) and SK&F-89976-A (Ali et al., 1985) were synthesized as described previously. Tiagabine was synthesized as described by Andersen et al. (1993).

2.2 Methods

2.2.1 Stable transfection

Stable cell lines for human GAT-1, rat GAT-2, human GAT-3, and human BGT-1 were generated in LM(tk$^-$) cells using the calcium phosphate method and selection in G-418, as described previously (Weinshank et al., 1992). Cells were grown under standard conditions (37° C., 5% $CO_2$) in DMEM (Dulbecco's modified Eagles's medium; GIBCO, Grand Island, N.Y.). Human GAT-1 is the human homologue of the rat transporter GAT-1 (Nelson et al., 1990) which we recloned. Human GAT-3 and human BGT-1 are the human homologues of rat GAT-3 (Borden et al., 1992) and dog BGT-1 (Yamauchi et al., 1992); a more complete description of these homologues will be described in subsequent communications (Borden et al., in preparation).

2.2.2 Transient transfection

GABA transport by rat GAT-1 and rat GAT-3 was examined in transiently transfected cells. Transient transfections were conducted as previously described (Smith et al., 1992), with the following modifications: COS cells grown in 75 cm$^2$ or 150 cm$^2$ flasks in DMEM with 10% bovine calf serum, 100 U/ml penicillin G, and 100 µg/ml streptomycin sulfate (37° C., 5% $CO_2$) were transfected using DEAE-dextran. On the day following transfection the cells were split into 24-well assay plates (well diameter=18 mm) coated with poly-D-lysine (10 µg/ml), and transport was measured 24 hours later.

2.2.3 Transport assay

Transport by attached cells was measured as described previously (Borden et al., 1992), with the following modifications. Cells grown in 24-well plates were washed 3× with HEPES-buffered saline (HBS, in mM: NaCl, 150; HEPES, 20; $CaCl_2$, 1; glucose, 10; KCl, 5; $MgCl_2$1; pH 7.4) and allowed to equilibrate on a 37° C. slide warmer. After 10 minutes the medium was removed and unlabeled drugs in HBS were added (450 µl/well). Transport was initiated by adding 50 µl per well of a concentrated solution of [$^3$H] GABA in HBS (final concentration=50 nM). Non-specific uptake was defined in parallel wells with 1 mM unlabeled GABA, and was subtracted from total uptake (no competitor) to yield specific uptake; all data represent specific uptake. Plates were incubated at 37° C. for 10 minutes, then washed rapidly 3× with ice-cold HBS, using a 24-position plate washer (Brandel, Gaithersburg, Mass.; model PW-12). Cells were solubilized with 0.05% sodium deoxycholate/0.1N NaOH (0.25 ml/well), an aliquot neutralized with 1N HCl, and radioactivity was determined by scintillation counting. Protein was quantified in an aliquot of the solubilized cells using a BIO-RAD protein assay kit, according to the manufacturer's directions.

Lipophilic inhibitors were dissolved in methylsulfoxide (DMSO). The final concentration of DMSO in the transport assay was ≦2%, and control experiments demonstrated that this concentration had no significant effect on transport.

2.2.4 Data Analysis

Competition curves were conducted in duplicate, using 10 concentrations of unlabeled drug. $IC_{50}$ values (concentrations resulting in 50% inhibition of uptake) were derived using software from GraphPad Inplot (San Diego, Calif.). Data were not corrected for the concentration of radioligand since [$^3$H]GABA was employed at a concentration well below its $K_M$; however, since initial rates were not studied, data are presented as $IC_{50}$. All data throughout the paper represent means±S.E.M.

3. RESULTS

Figure 11:
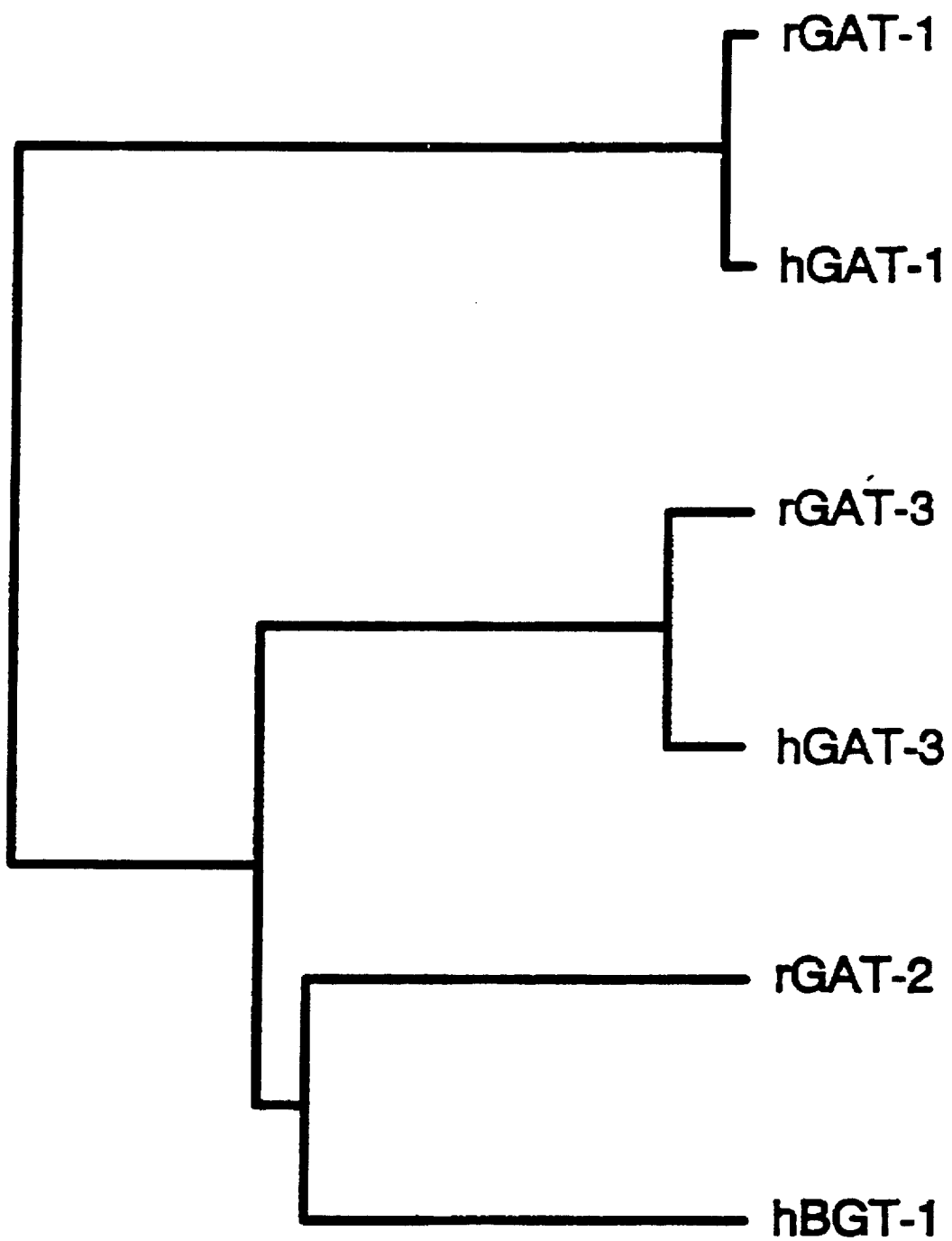
FIG. 11. Amino acid relationships of cloned GABA transporters. The amino acid sequences of rat GAT-1 (Guastella et al., 1990), human GAT-1 (Nelson et al., 1990), rat GAT-2 (Borden et al., 1992), rat GAT-3 (Borden et al., 1992), human GAT-3 (Borden et al., submitted), and human BGT-1 (Borden et al., submitted) were compared using the Pileup program (Genetics Computer Group, Inc., Madison, USA). The lengths of the lines indicate the reciprocal of the sequence similarities.

In the present study we used transfected cell lines expressing rat and human GAT-1, rat GAT-2, rat and human GAT-3, and human BGT-1. FIG. 11 shows a dendrogram describing the amino acid relationships between these transporters. As described previously (Borden et al., 1992), GAT-2 and GAT-3 are more closely related to each other than to GAT-1.

Human BGT-1 is most related to GAT-2, and least to GAT-1. As expected, species homologues are highly related to one another.

FIG. 12 shows the structures of the lipophilic compounds examined in this study, as well as the parent compounds (±)-nipecotic acid and guvacine. SK&F 89976-A (N-(4,4-diphenyl-3-butenyl)-3-piperidinecarboxylic acid) is a nipecotic derivative with a 4,4-diphenyl-3-butenyl moiety attached to the ring nitrogen (Yunger et al., 1984). Tiagabine ((R)-1-[4,4-Bis(3-methyl-2-thienyl)-3-butenyl]-3-piperidencarboxylic acid) is similar to SK&F 89976-A but has a bis-3-methylthienyl substituent instead of the two phenyl groups (Andersen et al., 1993). CI-966 ([1-[2-[bis4-(trifluoromethyl)phenyl]methoxy]ethyl]-1,2,5,6-tetrahydro-3-pyridinecarboxylic acid) is a guvacine derivative and differs from the previous two compounds in having a para-substituted trifluromethyl biphenyl ether moiety attached to the ring nitrogen via an ethylene bridge (Bjorge et al., 1990). NNC-711 (1-(2-(((diphenylmethylene)amino)oxy)ethyl)-1,2,4,6-tetrahydro-3-pyridinecarboxylic acid hydrochloride) is also a guvacine derivative with a biphenylmethyleneoxime unit attached to the ring nitrogen, also via an ethylene bridge (Suzdak et al., 1992).

Table 9 shows the potency of GABA and the hydrophilic inhibitors nipecotic acid, guvacine, and β-alanine at each of the four cloned GABA transporters. GABA displays similar high-affinity ($IC_{50} \approx 5$ μM) at human GAT-1, rat GAT-2, and human GAT-3, but is approximately 7-fold less potent at human BGT-1. The lower affinity of GABA at rat GAT-1 and rat GAT-3 is due, at least in part, to the use of transient transfection for these clones (L. Borden, unpublished) and perhaps to species differences in transporter structure that may alter drug affinities. Table 9 also shows that (±)-nipecotic acid and guvacine display modest selectivity for GAT-1 ($IC_{50}s=14-39$ μM) as compared to GAT-2 and GAT-3 ($IC_{50}s=102-378$ μM), whereas both compounds have low affinity at hBGT-1 ($IC_{50}>1$ mM). (R)-nipecotic acid is more potent than (S)-nipecotic acid, and accounts for most of the activity of the racemate. As described previously (Borden et al., 1992), β-alanine has greater potency at GAT-2 and GAT-3 ($IC_{50}s=19-110$ μM) than at GAT-1, regardless of species; β-alanine also displays low potency ($IC_{50}>1$ mM) at hBGT-1.

Figure 13:
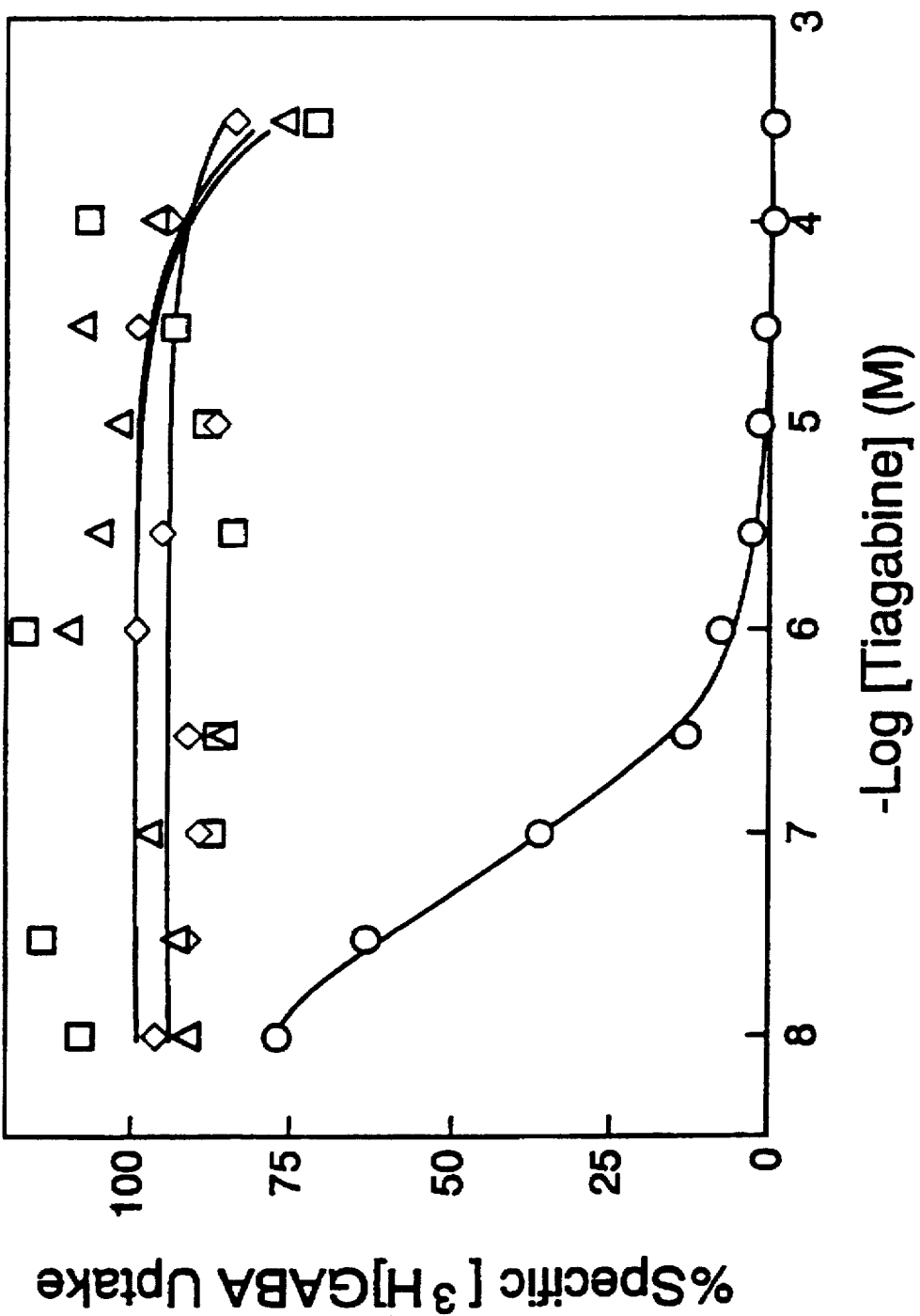
FIG. 13. Potency of Tiagabine at cloned GABA transporters. Cell lines expressing hGAT-1 (○), rGAT-2 (□), hGAT-3 (△) and hBGT-1 (◇) were incubated with [$^3$H] GABA and the indicated concentrations of Tiagabine. Data show specific uptake, expressed as percent of uptake in the absence of inhibitor. Standard deviations, omitted for clarity, were ≦15%. This experiment was repeated with similar results.

The data for the potency of the lipophilic compounds at the cloned transporters are summarized in Table 9, and a representative experiment for Tiagabine is shown in FIG. 13. The $IC_{50}$ values of the lipophilic compounds at GAT-1 range between 26 and 260 nM at GAT-1 (Table 9); these compounds are thus 50- to 200-fold more potent at this transporter than are (±)-nipecotic acid and guvacine. The compound with the highest affinity at human GAT-1 is NNC-711, followed by Tiagabine, SK&F 89976-A, and CI-966. A similar order of potency is observed at rat GAT-1 although the absolute affinities are somewhat lower.

In contrast to GAT-1, the lipophilic compounds all display low affinity at GAT-2, GAT-3, and BGT-1. As shown in Table 9, the $IC_{50}$ values at these transporters range from about 300 μM to greater than 1 mM, regardless of species (rat or human) or type of transfectant (stable or transient). Thus, all four lipophilic compounds display specificity for GAT-1 of nearly three orders of magnitude when compared to the other cloned GABA transporters. These findings confirm and extend the report by Clark et al. (1992) that NNC-711 has higher affinity for GAT-1 than GAT-3.

TABLE 9

Affinity of transport inhibitors at cloned GABA transporters.
The compounds shown were examined for their ability to inhibit uptake of [$^3$H] GABA by each of the cloned GABA transporters, as described in Methods. Data show the $IC_{50}$ for inhibition of [$^3$H] GABA uptake, in μM and represent means ± S.E.M.; the values in parentheses indicate the number of experiments.

| clone/ compound | human GAT-1 | rat GAT-1 | rat GAT-2 | human GAT-3 | rat GAT-3 | human BGT-1 |
|---|---|---|---|---|---|---|
| GABA | 5 ± 1 (3) | 30 ± 8 (3) | 5 ± 2 (3) | 7 ± 1 (4) | 33 ± 10 (3) | 36 ± 3 (4) |
| (R,S)-nipecotic acid | 8 ± 0.4 (3) | 24 ± 6 (3) | 38 ± 4 (4) | 106 ± 13 (3) | 159 ± 30 (3) | 2370 ± 617 (4) |
| (R)-nipecotic acid | 5.96 ± 0.8 (3) | ND* | 19 ± 2 (3) | 51 ± 6 (4) | ND | 2310 ± 114 (3) |
| (S)-nipecotic acid | 116 ± 8 (3) | ND | 763 ± 55 (3) | 2320 ± 86 (4) | ND | 6410 ± 213 (3) |
| guvacine | 14 ± 3 (3) | 39 ± 6 (3) | 58 ± 5 (4) | 119 ± 24 (3) | 378 ± 175 (3) | 1870 ± 387 (3) |
| β-alanine | 5690 ± 1890 (3) | 2920 ± 197 (3) | 19 ± 7 (3) | 58 ± 3 (3) | 110 ± 40 (3) | 1320 ± 224 (3) |
| CI-966 | 0.26 ± 0.05 (4) | 1.2 ± 0.2 (5) | 297 ± 34 (3) | 333 ± 76 (3) | 1140 ± 337 (3) | 300 ± 10 (3) |
| Tiagabine | 0.07 ± 0.007 (7) | 0.64 ± 0.15 (5) | 1410 ± 250 (3) | 917 ± 193 (3) | 2040 ± 107 (3) | 1670 ± 722 (3) |
| SK&F 89976-A | 0.13 ± 0.01 (3) | 0.64 ± 0.19 (5) | 550 ± 225 (4) | 944 ± 259 (3) | 4390 ± 1420 (3) | 7210 ± 3630 (4) |
| NNC-711 | 0.04 ± 0.01 (4) | 0.38 ± 73 (4) | 171 ± 53 (5) | 1700 ± 252 (3) | 349 ± 151 (3) | 622 ± 265 (4) |

*ND not determined

4. DISCUSSION

Molecular cloning has revealed a surprising diversity of GABA transporters. However, little is known regarding the relative contribution of the four cloned GABA transporters to GABAergic transmission. The lipophilic compounds SK&F 89976-A, Tiagabine, CI-966, and NNC-711 all display anticonvulsive activity in animals (Yunger et al., 1984; Swinyard et al., 1991; Nielsen et al., 1991; Taylor et al., 1990; Suzdak et al., 1992). Further, Tiagabine has demonstrated anti-seizure activity in patients in Phase II clinical trials (Richens et al., 1992; Crawford et al., 1993; Rowan et al., 1993), thus demonstrating the therapeutic utility of inhibiting GABA transport. Our finding that these compounds are highly selective for GAT-1 demonstrates clearly that their anticonvulsive activity is mediated via actions at this site. It should be noted that GAT-1 is the predominant GABA transporter in the rat brain, accounting for approximately 85% of GABA transport when assayed in vitro (Borden et al., submitted).

Severe adverse effects were noted in human volunteers after administration of CI-966 (Sedman et al., 1990), but were not observed with Tiagabine (Richens et al., 1992; Rowan et al., 1993; Crawford et al., 1993). The finding that both compounds display a similar selectivity at the cloned GABA transporters suggests a common site of action in the brain. The untoward side-effects of CI-966 may have resulted from the high doses employed in the trials; alternatively, they may reflect interactions of either the parent compound, or a toxic metabolite, with sites distinct from GABA transporters (for further discussion, see Suzdak, 1993).

Due to their high degree of selectivity for GAT-1, the lipophilic compounds described above are important tools for the study of this transporter but offer little insight into the functions of the other cloned GABA transporters; future experiments will be aimed at the development of lipophilic ligands for these sites. Further study of the lipophilic GABA transport inhibitors should increase our understanding of GABA transporters and the role they play in regulating GABAergic activity, and may result in the development of novel therapeutic agents for anxiety, epilepsy, and other neuropsychiatric disorders.

REFERENCES

Adham, N., Roamienko, P., Hartig, P., Weinshank, R. L., and Branchek, T. A. (1992) The rat 5-hydroxytryptamine$_{1B}$ receptor is the species homologue of the human 5-hydroxytryptamine$_{1D\beta}$ receptor. Molecular Pharmacol. 41, 1–7.

Ali, F. E., W. E. Bondinell, P. A. Dandridge, J. S. Fraze, E. Garvey, G. R. Girard, C. Kaiser, T. W. Ku, J. L. Lafferty, G. I. Moonsammy, H. J. Oh, J. A. Rush, P. E. Setler, O. D. Stringer, J. W. Venslavsky, B. W. Volpe, L. M. Yunger and C. L. Zirkle C L, 1985, Orally active and potent inhibitors of γ-aminobutyric acid uptake. J. Med. Chem. 28, 653.

Amara, S.G. (1992) A tale of two families. Nature 360, 420–421.

Amara, S.G. and Arriza, J.L. (1993) Neurotransmitter transporters: three distinct gene families. Current Opinion on Cell Biology 3: 337–344.

Andersen, K. E., C. Braestrup, F. C. Gronwald, A. S. Jorgenesen, E. B. Nielsen, P. D. Sonnewald, P. D. Suzdak and L. J. S. Knutsen, 1993, The synthesis of novel GABA uptake inhibitors: 1. Elucidation of the structure-activity studies leading to the choice of (R)-1-[4,4-Bis(3-methyl-2-thienyl)-3-butenyl]-3-piperidencarboxylic acid (Tiagabine) as an anticonvulsant candidate. J. Med. Chem. 36, 1716.

Attwell, D., Barbour, B., and Szatkowski, M (1993) Nonvesicular release of neurotransmitter. Neuron 11: 401–407.

Blakely, R. D., Berson, H. E., Fremeau, Jr., R. T., Caron, M. G., Peek, M. M., Prince, H. K., and Bradley, C. C. (1991) Cloning and expression of as functional serotonin transporter from rat brain. Nature 354, 66–70.

Bjorge, S., A. Black, H. Bockbrader, T. Chang, V. E. Gregor, S. J. Lobbestael, D. Nugiel, M. R. Pavia, L. Radulovic and T. Woolf, 1990, Synthesis and metabolic profile of CI-966, Drug Development Research 21, 189.

Borden, L. A., Smith, K. E., Hartig, P. R., Branchek, T. A., and Weinshank, R. L. (1992) Molecular heterogeneity of the y-aminobutyric acid (GABA) transport system. J. Biol. Chem. 267(29), 21098–21104.

Capecchi, M. R., (1989) Science 244: 1288–1292.

Chadwick, D., Richens, A., Duncan, J., Dam, M., Gram, L., Morrow, J., Mengel, H., Shu, V., McKelvy, J. F., and Pierce, M. W. (1991) Tiagabine HCl: Safety and efficacy as adjunctive treatment for complex partial seizures. Epilepsia 32, suppl. 3: 20.

Chirgwin, J. M., Przybyla, A. E., MacDonald, R. J., and Rutter, W. J. (1979) Isolation of biologically active ribonucleic acid from sources enriched in ribonuclease. Biochemistry 18(24): 5294–5299.

Christensen, H. N. (1984) Amino acid transport in isolated rat hepatocytes. Biochim. Biophys. Acta 779, 255–269.

Clark, J. A., Deutch, A. Y., Gallipoli, P. Z., and Amara, S. G. (1992) Functional expression and CNS distribution of a β-alanine-sensitive neuronal GABA transporter. Neuron 9, 337–348.

Cohen, J. S., (1989) Trends in Pharm. Sci. 10:435.

Crawford, P. M., M. Engelsman, S. W. Brown, T. W. Rentmeester, B. Pedersen, C. E. Clarke, R. Hoornstra, J. Overweg, M. Jongsma, M. V. Rademaker, D. G. A. Kasteleijn-Nolst Trenite, H. Meinardi, E. R. Newton, A. MacDonald, J. Hulsman, L. C. Lassen, D. Edwards, S. Snel and H. B. Mengel, 1993, Tiagabine: Phase II study of efficacy and safety in adjunctive treatment of partial seizures, Epilepsia 34, suppl. 2, 182.

Danielson, P. E., Forss-Pettr, S., Brow, M. A., Calavetta, L., Douglas, J., Milner, R. J., and Sutcliffe, J. G. (1988) p1B15: A cDNA clone of the rat mRNA encoding cyclophilin. DNA 7, 261–267.

Forray, C. and El-Fakahany, S. E. (1990) On the involvement of multiple muscarinic receptor subtypes in the activation of phosphoinositide metabolism in rat cerebral cortex. Molec. Pharmacol. 37, 898–902.

Fremeau, Jr., R. T., Caron, M. G., and Blakely, R. D. (1992) Molecular cloning and expression of a high affinity L-proline transporter expressed in putative glutamatergic pathways of rat brain. Neuron 8, 915–926.

Fujii., A. and Cook, E. S. (1975) Journal of Medicinal Chemistry 18:502–505.

Giros, B., El Mestikawy, S., Godinot, N., Zheng, K., Han, H., Yang-Fen, T., and Caron, M. G. (1992) Cloning, pharmacological characterization, and chromosome assignment of the human dopamine transporter. Molec. Pharmacol. 42, 383–390.

Goodchild, C.S., 1993, GABA receptors and benzodiazepines, Br. J. Anaesthesia 71, 127.

Guastella, J., Nelson, N., Nelson, H., Czyzyk, L., Keynan, S., Miedel, M. C., Davidson, N., Lester, H.A., and Kanner, B.I. (1990) Cloning and expression of a rat brain GABA transporter. Science 249, 1303–1306.

Guastella, J., Brecha, N., Weigmann, C., and Lester, H. A. (1992) Cloning, expression, and localization of a rat brain high-affinity glycine transporter. Proc. Natl. Acad. Sci. USA 89, 7189–7193.

Hartig, P. R. (1992) Can cloned receptors aid drug research? Proc. Royal Soc. Edinburgh 99B(1/2), 1925.

Heilig, C. W., Stromski, M. E., Blumenfeld, J. D., Lee, J. P., and Gullans, S. R. (1989) Characterization of the major brain osmolytes that accumulate in salt-loaded rats. Am J. Physiol. 257, F1108–1116.

Hoffman, B. J., Mezey, E., and Brownstein, M. J. (1991) Cloning of a serotonin transporter affected by antidepressants. Science 254, 9–580.

Hogan, B., et al., (1986) Manipulating the Mouse Embryo, A Laboratory Manual, Cold Spring Laboratory.

Iversen, L.L. and Bloom, F.E. (1972) Studies of the uptake of $^3$H-GABA and $^3$H-glycine in slices and homogenates of rat brain and spinal cord by electron microscope autoradiography. Brain Res. 41, 131–143.

Jhiang, S. M., Fithian, L., Smanik, P., McGill, J., Tong, Q., and Mazzaferri, E. L. (1993) Cloning of the human taurine transporter and characterization of taurine uptake in thyroid cells. FEBS 318(2), 139–144.

Johnstone, S. R., Levi, G., Wilkin, G. P., Schneider, A., and Ciotti, M. T. (1986) Subpopulations of rat cerebellar astrcoytes in primary culture: Morphology, cell surface antigens and [$^3$H]AGBA transport. Developmental Brain Res. 24, 63–75.

Kanai, Y. and Hediger, M. A. (1992) Primary structure and functional characterization of a high-affinity glutamate transporter. Nature 360, 467–471.

Kanner, B. I. and Schuldiner, S. (1987) Mechanism of transport and storage of neurotransmitter; in CRC Critical Reviews in Biochemistry 22(1), 1–38.

Kao, H.-T., Adham, N., Olsen, M. A., Weinshank, R. L., Branchek, T. A., and Hartig, P. R. (1992) Site-directed mutagenesis of a single residue changes the binding properties of the serotonin 5-HT$_2$ receptor from a human to a rat pharmacology. FEBS 307(3), 324–328.

Kilty, J.E., Lorang, D., and Amara, S. G. (1991) Cloning and expression of a cocaine-sensitive rat dopamine transporter. Science 254, 578–579.

Krogsgaard-Larsen, P., Falch, E., Larsson, O. M., and Schousboe, A. (1987) GABA uptake inhibitors: relevance to antieplieptic drug research. Epilepsy Res. 1, 77–93.

Levi, G. and Raiteri, M. (1993) Carrier-mediated release of neurotransmitters. TINS 16(10), 415–419.

Levi, G., Wilkin, G. P., Ciotti, M. T., and Johnstone, S. (1983) Enrichment of differentiated, stellate astrocytes in cerebellar interneuron cultures as studied by GFAP immunofluorescence and autoradiographic uptake patterns with [$^3$H]D-aspartate and [$^3$H]GABA. Developmental Brain Res. 10, 227–241.

Lillien, L. E. and Raff, M. (1990) Analysis of the cell-cell interactions that control Type-2 astrocyte development in vitro. Neuron 4, 525–534.

Link, R., Daunt, D., Barsh, G., Chruscinski, A., and Kobilka, B. (1992) Cloning of two mouse genes encoding $\alpha_2$-adrenergic receptor subtypes and identification of a single amino acid in the mouse $\alpha_2$-C10 homolog responsible for an interspecies variation in antagonist binding. Molecular Pharmacol. 42, 16–27.

Liu, Q.-R., Mandiyan, S., Nelson, H., and Nelson, N. (1992a) A family of genes encoding neurotransmitter transporters. Proc. Natl. Acad. Sci. USA 89, 6639–6643.

Liu, Q.-R., Nelson, H., Mandiyan, S., Lopez-Corcuera, B., and Nelson, N. (1992b) Cloning and expression of a glycine transporter from mouse brain. FEBS 305(2), 110–114.

Liu, Q.-R., Lopez-Corcuera, B., Nelson, H., Mandiyan, S., and Nelson, N. (1992c) Cloning and expression of a cDNA encoding the transporter of taurine and β-alanine in mouse brain. Proc. Natl. Acad. Sci. 89, 12145–12149.

Liu, Q.-R., Lopez-Corcuera, B., Mandiyan, S., Nelson, H., and Nelson, N. (1993) Molecular characterization of four pharmacologically distinct α-aminobutyric acid transporters in mouse brain. J. Biol. Chem. 268(3), 2106–2112.

Lopata, M. A., Cleveland, D. W., and Sollner-Webb, B. (1984). Nucl. Acids Res. 12, 5707–5717.

Lopez-Corcuera, B., Liu, Q.-R., Mandiyan, S., Nelson, H., and Nelson, N. (1992) Expression of mouse cDNA encoding a novel γ-aminobutyric acid transporter. J.Biol. Chem. 267(25), 17491–17493.

Low, M. J., R. M. Lechan and R. E. Hammer, (1986) Science 231: 1002–1004.

Lu, B., Yokoyama, M., Dreyfus, C. F., and Black, I. B. (1991) NGF gene expression in actively growing brain glia. J. Neurosci. 11(2), 318–326.

Mabjeesh, N. J., Frese, M., Rauen, T., Jeserich, G., and Kanner, B. I. (1992) Neuronal and glial γ-aminobutyric acid transporters are distinct proteins. FEBS 299(1), 99–102.

MacDonald, R. J., Swift, G. H., Przybyla, A. E., and Chirgwin, J. M. (1987) Isolation of RNA using guanidinium salts. In Methods Enzymol. Vol. 152, Guide to Molecular Cloning Techniques, eds. S. L. Berger and A. R. Kimmel, pp. 219–227.

Mager, S., Quick, M., Labarca, C., Davidson, N., and Lester, H. A. Neuron, in press Maniatis, T., E. F. Fritsch, and J. Sambrook, Molecular Cloning Manual, Cold Spring Harbor Laboratory, Cold Spring Harbor N.Y. (1982).

Marriott, D. R. and Wilkin, G. P. (1993) Substance P receptors on O-2A progenitor cells and Type-2 astrocytes in vitro. J. Neurochem. 61, 826–834.

Martin, D. L. (1976) Carrier-mediated transport and removal of GABA from synaptic regions. In GABA in nervous sytem function, eds. E. Roberts, T. N. Chase, and D.B. Tower, Raven Press, NY, pp. 347–386.

McCarthy, K. D. and DeVellis, J. (1980) Preparation of separate astroglial and oligodendroglial cell cultures from rat cerebral tissue. J. Cell Biol. 85, 890–902.

Miller, J. and Germain, R. N. (1986) Efficient cell surface expression of class II MHC molecules in the absence of associated invariant chain. J. Exp. Med. 164, 1478–1489.

Miller, R. H., ffrench-Constant, C., and Raff, M. C. (1989) The macroglial cells of the rat optic nerve. Ann. Rev. Neurosci. 12, 517–534.

Missale, C., Boroni, F., Castelletti, L., Dal Toso, R., Gabellini, N., Sigala, S., and Spano, P. (1991) Lack of coupling of D-2 receptors to adenylate cyclase in GH-3 cells exposed to epidermal growth factor. J. Biol. Chem. 266(34), 23392–23398.

Nelson, H., Mandiyan, S., and Nelson, N. (1990) Cloning of the human brain GABA transporter. FEBS 269(1), 181–184.

Nielsen, E. B., P. D. Suzdak, K. E. Andersen, L. J. S. Knutsen, U. Sonnewald, and C. Braestrup, 1991, Characterization of tiagabine (NO-328), a new potent and selective GABA uptake inhibitor, Eur. J. Pharmacol. 196, 257.

Oberdick, J., Smeyne, R. J., Mann, J. R., Jackson, S. and Morgan, J. I. (1990) Science 248: 223–226.

Pacholczyk, T., Blakely, R. D., and Amara, S. G. (1991) Expression cloning of a cocaine- and antidepressant-sensitive noradrenaline transporter. Nature 350, 350–354.

Pines, G., Danboldt, N. C., Bjoras, M., Zhang, Y., Bendahan, A., Eide, L., Koepsell., H., Storm-Mathisen, J., Seeberg, E., and Kanner, B. I. (1992) Cloning and expression of a rat brain L-glutamate transporter. Nature 360, 464–467.

Radian, R., Ottersen, O. P., Storm-Mathisen, J., Castel, M., and Kanner, B. I. (1990) Immunocytochemical localization of the GABA transporter in rat brain. J. Neuroscience 10(4), 1319–1330.

Raff, M. C. (1989) Glial cell diversification in the rat optic nerve. Science 243, 1450–1455.

Raff, M. C., Miller, R. H., and Noble, M. (1983) A glial progenitor cell that develops in vitro into an astrocyte or an oligodendrocyte depending on culture medium. Nature 303, 390–396.

Rattray, M. and Priestley, J. V. (1993) Differential expression of GABA transport-1 messenger RNA in subpopulations of GABA neurones. Neuroscience Letters 156, 163–166.

Reynolds, R. and Herschkowitz, N. (1984) Uptake of [$^3$H] GABA by oligodendrocytes in dissociated brain cell culture: A combined autoradiographic and immunocytochemical study. Brain Res. 322, 17–31.

Richens, A., D. Chadwick, J. Duncan, M. Dam, J. Morrow, L. Gram, H. Mengel, V. Shu, M. Pierce, C. Rask and B. Hightower, 1992, Safety and efficacy of Tiagabine HCl as adjunctive treatment for complex partial seizures. Epilepsia 33, suppl. 3, 119.

Rowan, A. J., P. Ahmann, B. Wannamaker, S. Schacter, C. Rask and B. Uthman, 1993, Safety and efficacy of three dose levels of Tiagabine HCl versus placebo as adjunctive treatment for complex partial seizures, Epilepsia 34, suppl. 2, 157.

Sambrook, J., Fritsch, E. F., Maniatis, T. (1989), in Molecular Cloning, A Laboratory Manual, Cold Spring Harbor Laboratory Press, 1989.

Sanger, F., Nicklen, S., and Coulsen, A. R. (1977) DNA sequencing with chain-terminating inhibitors. Proc. Natl. acad. Sci. USA 74, 5463–5467.

Sarver, N., (1990) Science 247, 1222.

Sedman, A. J., G. P. Gilmet, A. J. Sayed and E. L. Posvar, 1990, Initial human safety and tolerance study of a GABA inhibitor, CI-966: Potential role as a mediator in the pathogenesis of schizophrenia and mania, Drug Development Research 21, 235.

Shimada, S., Kitayama, S., Lin, C.-L., Patel, A., Nanthakumar, E., Gregor, P., Kuhar, M., and Uhl, G. (1991) Cloning and expression of a cocaine-sensitive dopamine transporter complementary DNA. Science 254, 576–578.

Silverman, M. (1991) Annu. Rev. Biochem. 60:757794.

Smith, K. E., Borden, L. A., Hartig, P. R., Branchek, T., and Weinshank, R. L. (1992a) Cloning and expression of a glycine transporter reveal colocalization with NMDA receptors. Neuron 8, 927–935.

Smith, K. E., Borden, L. A., Wang, C.-H. D., Hartig, P. R., Branchek, T. A., and Weinshank, R. L. (1992b) Cloning and expression of a high affinity taurine transporter from rat brain. Mol. Pharmacol. 42, 563–569.

Storck, T., Schulte, S., Hofmann, K., and Stoffel, W. (1992) Structure, expression, and functional analysis of a Na$^+$-dependent glutamate/aspartate transporter from rat brain. Proc. Natl. Acad. Sci. USA 89, 10955–10959.

Suzdak, P. D., K. Frederiksen, K. E. Andersen, P. O. Sorensen, L. J. S. Knutsen and E. B. Nielsen, 1992, NNC-711, a novel potent and selective γ-aminobutyric acid uptake inhibitor: pharmacological characterization, Europ. J. Pharmacol. 223, 189.

Suzdak, P. D., 1993, Lipophilic GABA uptake inhibitors: Biochemistry, pharmacology and therapeutic potential, Drugs of the Future 18 (12), 1129.

Swinyard, E. A., H. S. White, H. H. Wolf and W. E. Bondinell, 1991, Anticonvulsant profiles of the potent and orally active GABA uptake inhibitors SK&F 89976-A and SK&F 100330-A and four prototype antiepileptic drugs in mice and rats, Epilepsia 32(4), 569.

Taylor, C. P., M. G. Vartanian, R. D. Schwarz, D. M. Rock, M. J. Callahan, and M. D. Davis, 1990, Pharmacology of CI-966: A potent GABA uptake inhibitor, in vitro and in experimental animals, Drug Development Research 21.

Twyman, R. E. and R. L. Macdonald, 1991, Antiepileptic Drug Regulation of GABA Receptor Channels, in: GABA Mechanisms in Epilepsy, ed. G. Tunnicliff and B. U. Raess (Wiley-Liss, New York) p. 89.

Uchida, S., Kwon, H. M., Yamauchi, A., Preston, A. S., Marumo, F., and Handler, J. S. (1992) Molecular cloning of the cDNA for an MDCK cell Na$^+$- and Cl$^-$-dependent taurine transporter that is regulated by hypertonicity. Proc. Natl. Acad. Sci. USA 89, 8230–8234.

Uhl, G. R. (1992) Neurotransmitter transporters (plus): a promising new gene family. Trends in Neurosci. 15(7), 265–268.

Uhl, G. R. and Hartig, P. R. (1993) Transporter explosion: update on uptake. Trends in Pharmacol. Sci. 13, 421–425.

Usdin, T. B., Mezey, E., Chen, C., Brownstein, M. J., and Hoffman, B. J. (1991) Proc. Natl. Acad. Sci. 88: 11168–11171.

Vaysse, P. J.-J., Zukin, R. S., Fields, K. L., and Kessler, J. A. (1990) Characterization of opiod receptors in cultured neurons. J. Neurochem. 55, 624–631.

Vaysse, P. J.-J. and Goldman, J. E. (1990) A clonal analysis of glial lineages in forebrain development in vitro. Neuron 5, 227–235.

Weinshank, R. L., Zgombick, J. M., Machi, M., Branchek, T.A., and Hartig, P.R. (1992) Human serotonin 1D receptor is encoded by a subfamily of two distinct genes: 5-HT$_{1D\alpha}$ and 5-HT$_{1D\beta}$. Proc. Natl. acad. Sci. USA 89, 3630–3634.

Weintraub, H. M., (1990) Scientific American p. January, p. 40.

Wilkin, G., P. Levi, G., Johnstone, S. R., and Riddle, P. N. (1983) Cerebellar astrocyte cells in primary culture: Expression of different morphological appearances and different ability to take up [$^3$H]-aspartate and [$^3$H]GABA. Development Brain Research 10, 265–277.

Yamauchi, A., Uchida, S., Kwon, H. M., Preston, A. S., Robey, R. B., Garcia-Perez, A., Burg, M. B., and Handler, J. S. (1992) Cloning of a Na$^+$- and Cl$^-$-dependent betaine transporter that is regulated by hypertonicity. J. Biol. Chem. 267(1), 649–652.

Yunger, L. M., P. J. Fowler, P. Zarevics, P. E. Setler, 1984, Novel inhibitors of γ-aminobutyric acid (GABA) uptake: anticonvulsant actions in rats and mice, J. Pharmacol. Exp. Ther. 228, 109.

Zgombick, J. M., Weinshank, R. L., Macchi, M., Schecter, L. E., Branchek, T. A., and Hartig, P. R. (1991) Expression and pharmacological characterization of a canine 5-hydroxytryptamine$_{1D}$ receptor subtype. Molecular Pharmacol. 40, 1036–1042.

Zimmer, A. and Gruss, P., (1989) Nature 338, 150–153.

What is claimed is:

1. A process for identifying a chemical compound which specifically binds to a human betaine/GABA transporter, which comprises contacting nonneuronal cells expressing on their cell surface the human betaine/GABA transporter, wherein the human betaine/GABA transporter has an amino acid sequence as shown in SEQ ID NO. 2, with the chemical compound under conditions suitable for binding, and detecting specific binding of the chemical compound to the human betaine/GABA transporter.

2. A process for identifying a chemical compound which specifically binds to a human betaine/GABA transporter, which comprises contacting a membrane fraction from a cell extract of nonneuronal cells expressing on their cell surface the human betaine/GABA transporter, wherein the human betaine/GABA transporter has an amino acid sequence as shown in SEQ ID NO. 2, with the chemical compound under conditions suitable for binding, and detecting specific binding of the chemical compound to the human betaine/GABA transporter.

3. A process involving competitive binding for identifying a test chemical compound which specifically binds to a human betaine/GABA transporter, which comprises separately contacting nonneuronal cells expressing on their cell surface the human betaine/GABA transporter, wherein the human betaine/GABA transporter has an amino acid sequence as shown in SEQ ID NO. 2, with both the test chemical compound and a second chemical compound known to specifically bind to the transporter, and with only the second chemical compound, under conditions suitable for binding of both compounds, and detecting specific binding of the chemical compound to the human betaine/GABA second transporter, a decrease in the binding of the second chemical compound to the human betaine/GABA transporter in the presence of the test chemical compound indicating that the test chemical compound binds to the human betaine/GABA transporter.

4. A process involving competitive binding for identifying a test chemical compound which specifically binds to a human betaine/GABA transporter, which comprises separately contacting a membrane fraction from a cell extract of nonneuronal cells expressing on their cell surface the human betaine/GABA transporter, wherein the human betaine/GABA transporter has an amino acid sequence as shown in SEQ ID NO. 2, with both the test chemical compound and a second chemical compound known to specifically bind to the transporter, and with only the second chemical compound, under conditions suitable for binding of both compounds, and detecting specific binding of the second chemical compound to the human betaine/GABA transporter, a decrease in the binding of the second chemical compound to the human betaine/GABA transporter in the presence of the test chemical compound indicating that the test chemical compound binds to the human betaine/GABA transporter.

5. A process for identifying a chemical compound which specifically binds to and inhibits a human betaine/GABA transporter, which comprises separately contacting nonneuronal cells transfected with and expressing on their cell surface the human betaine/GABA transporter, wherein the human betaine/GABA transporter has an amino acid sequence as shown in SEQ ID NO. 2, with both the chemical compound and with a substrate for the transporter, and with only the substrate, under conditions suitable for binding and transport of the substrate, and detecting transport of the substrate, a decrease in the transport of the substrate by the human betaine/GABA transporter in the presence of the chemical compound indicating that the chemical compound binds to and inhibits the human betaine/GABA transporter.

6. A process for identifying a chemical compound which specifically binds to and activates a human betaine/GABA transporter, which comprises separately contacting nonneuronal cells transfected with and expressing on their cell surface the human betaine/GABA transporter, wherein the human betaine/GABA transporter has an amino acid sequence as shown in SEQ ID NO. 2, with both the chemical compound and with a substrate for the transporter, and with only the substrate, under conditions suitable for binding and transport of the substrate, and detecting transport of the substrate, an increase in the transport of the substrate by the human betaine/GABA transporter in the presence of the chemical compound indicating that the chemical compound binds to and activates the human betaine/GABA transporter.

7. A process of claim 1, 2, 3, 4, 5, or 6, wherein the non-neuronal cell is a mammalian cell.

8. A process of claim 7, wherein the mammalian cell is an Ltk- cell, a NIH-3T3 cell, a CHO cell, a HeLa cell or a Cos-7 cell.

* * * * *

UNITED STATES PATENT AND TRADEMARK OFFICE
CERTIFICATE OF CORRECTION

PATENT NO. : 5,766,848
DATED : June 16, 1998
INVENTOR(S) : Laurence A. Borden, Kelli E. Smith, Richard L. Weinshank It is certified that error appears in the above-identified patent and that said Letters Patent is hereby corrected as shown below:

column 5, line 58: "p-actin" should read --b-actin--
         line 58: "b2.o kb" should read -- ≈2.0 kb--
column 6, line 36: "culturs" should read --cultures--
column 9, line 20: "ATCC Accession No." should read
                   --ATCC Accession No.75854, deposited Aug. 9, 1994--
column 10, line 22: "ATCC Accession No." should read
                   --ATCC Accession No.75854, deposited Aug. 9, 1994--
column 14, line 59: "comserved" should read --conserved--
column 28, line 43, table 1: "dog VGT-$1^2$" should read --dog BGT-$1^2$--
column 33, line 30: "atmoshere" should read --atmosphere--
column 36, line 52: "$IC_5$" should read --$IC_{50}$--
column 41, line 54, table 4: "condtion" should read --condition--
column 43,
         line 39, table 8: "hybridazation" should read --hybridization--
column 45, line 58-59: "cotrespond" should read --correspond--

Signed and Sealed this

Eighteenth Day of May, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 2217 base pairs
( B ) TYPE: nucleic acid
( C ) STRANDEDNESS: double
( D ) TOPOLOGY: unknown ( i i ) MOLECULE TYPE: cDNA ( i i i ) HYPOTHETICAL: N ( i v ) ANTI-SENSE: N ( v i i ) IMMEDIATE SOURCE:
( A ) LIBRARY: HUMAN STRIATUM
( B ) CLONE: hS1a ( i x ) FEATURE:
( A ) NAME/KEY: CDS
( B ) LOCATION: 211..2052
( D ) OTHER INFORMATION:

( x i ) SEQUENCE DESCRIPTION: SEQ ID NO:1:

| | | | | | | | | | | | | |
|---|---|---|---|---|---|---|---|---|---|---|---|---|
| TTGGGACTCT | CCTGGAGACC | TGATGCCCAC | AGCCAAGCTG | ACCACAGGAG | CCGGTGCTGG | | | | | | | 60 |
| GGACTGAGGG | AAACTTAGAG | TTCAGAGAGG | GGGTGTGATT | TGCCTGAGGT | CACACAGCAA | | | | | | | 120 |
| GTTAGAGACC | CAGCTCCACG | ACTCATTGTC | TTGGCTTTGG | CCCTCGTCAT | CCTGCCCACC | | | | | | | 180 |
| CAGCGGGGCT | TCCCAACCCA | CCACACAGCC | ATG GAC GGG AAG GTG GCA GTG CAA | | | | | | | | | 234 |
| | | | Met Asp Gly Lys Val Ala Val Gln | | | | | | | | | |
| | | | 1             5 | | | | | | | | | |

```
GAG TAT GGG CCT CCT GCA GTC TCC TGG GTC CCC GAG GAG GGA GAG AAG      282
Glu Tyr Gly Pro Pro Ala Val Ser Trp Val Pro Glu Glu Gly Glu Lys
     10              15                  20

TTG GAC CAG GAA GAC GAG GAC CAG GTG AAG GAT CGG GGC CAA TGG ACC      330
Leu Asp Gln Glu Asp Glu Asp Gln Val Lys Asp Arg Gly Gln Trp Thr
 25                  30                  35                  40

AAC AAG ATG GAG TTT GTG CTG TCA GTG GCC GGG GAG ATC ATT GGG CTG      378
Asn Lys Met Glu Phe Val Leu Ser Val Ala Gly Glu Ile Ile Gly Leu
             45                  50                  55

GGC AAT GTC TGG AGG TTT CCC TAT CTC TGC TAC AAA AAC GGA GGT GGA      426
Gly Asn Val Trp Arg Phe Pro Tyr Leu Cys Tyr Lys Asn Gly Gly Gly
         60                  65                  70

GCC TTC TTC ATC CCC TAC TTC ATC TTC TTC TTT GTC TGC GGC ATC CCG      474
Ala Phe Phe Ile Pro Tyr Phe Ile Phe Phe Phe Val Cys Gly Ile Pro
     75                  80                  85

GTG TTC TTC CTG GAG GTG GCG TTG GGC CAA TAC ACC AGC CAA GGG AGT      522
Val Phe Phe Leu Glu Val Ala Leu Gly Gln Tyr Thr Ser Gln Gly Ser
 90                  95                  100

GTC ACA GCC TGG AGG AAG ATC TGC CCC CTC TTC CAG GGC ATT GGT CTG      570
Val Thr Ala Trp Arg Lys Ile Cys Pro Leu Phe Gln Gly Ile Gly Leu
105             110                 115                 120

GCA TCT GTG GTC ATC GAG TCA TAT TTG AAT GTC TAC TAC ATC ATC ATC      618
Ala Ser Val Val Ile Glu Ser Tyr Leu Asn Val Tyr Tyr Ile Ile Ile
            125                 130                 135

CTT GCC TGG GCT CTC TTC TAC CTG TTC AGC TCC TTC ACC TCT GAG CTG      666
Leu Ala Trp Ala Leu Phe Tyr Leu Phe Ser Ser Phe Thr Ser Glu Leu
        140                 145                 150

CCC TGG ACG ACC TGC AAC AAC TTT TGG AAC ACA GAG CAT TGC ACG GAC      714
```

|  |  |  |  |  |  |  |  |  |  |  |  |  |  |  |  |
|---|---|---|---|---|---|---|---|---|---|---|---|---|---|---|---|
| Pro | Trp | Thr<br>155 | Thr | Cys | Asn | Asn | Phe<br>160 | Asn | Thr | Glu | His<br>165 | Cys | Thr | Asp | |
| TTT | CTG | AAC | CAC | TCA | GGA | GCC | GGC | ACA | GTG | ACC | CCA | TTT | GAG | AAT | TTT | 762 |
| Phe | Leu<br>170 | Asn | His | Ser | Gly<br>175 | Ala | Gly | Thr | Val | Thr<br>180 | Pro | Phe | Glu | Asn | Phe |
| ACC | TCA | CCT | GTC | ATG | GAA | TTC | TGG | GAG | AGA | CGA | GTT | CTG | GGC | ATC | ACC | 810 |
| Thr | Ser<br>185 | Pro | Val | Met | Glu<br>190 | Phe | Trp | Glu | Arg<br>195 | Arg | Val | Leu | Gly | Ile | Thr<br>200 |
| TCG | GGC | ATC | CAT | GAC | CTG | GGC | TCC | CTG | CGC | TGG | GAG | CTG | GCC | CTG | TGC | 858 |
| Ser | Gly | Ile | His | Asp<br>205 | Leu | Gly | Ser | Leu | Arg<br>210 | Trp | Glu | Leu | Ala | Leu<br>215 | Cys |
| CTC | CTG | CTC | GCC | TGG | GTC | ATC | TGC | TAT | TTC | TGC | ATC | TGG | AAG | GGG | GTC | 906 |
| Leu | Leu | Leu | Ala<br>220 | Trp | Val | Ile | Cys | Tyr<br>225 | Phe | Cys | Ile | Trp | Lys<br>230 | Gly | Val |
| AAG | TCC | ACA | GGC | AAG | GTG | GTT | TAT | TTC | ACA | GCC | ACG | TTT | CCG | TAC | CTG | 954 |
| Lys | Ser | Thr<br>235 | Gly | Lys | Val | Val | Tyr<br>240 | Phe | Thr | Ala | Thr | Phe<br>245 | Pro | Tyr | Leu |
| ATG | CTT | GTC | ATT | TTG | CTG | ATC | AGA | GGT | GTC | ACC | CTT | CCC | GGA | GCC | TAC | 1002 |
| Met | Leu | Val<br>250 | Ile | Leu | Leu | Ile<br>255 | Arg | Gly | Val | Thr | Leu<br>260 | Pro | Gly | Ala | Tyr |
| CAG | GGC | ATC | ATC | TAC | TAC | TTG | AAG | CCA | GAT | TTG | TTC | CGC | CTC | AAG | GAC | 1050 |
| Gln<br>265 | Gly | Ile | Ile | Tyr | Tyr<br>270 | Leu | Lys | Pro | Asp | Leu<br>275 | Phe | Arg | Leu | Lys | Asp<br>280 |
| CCT | CAG | GTG | TGG | ATG | GAT | GCG | GGC | ACC | CAG | ATC | TTC | TTC | TCC | TTT | GCC | 1098 |
| Pro | Gln | Val | Trp | Met<br>285 | Asp | Ala | Gly | Thr | Gln<br>290 | Ile | Phe | Phe | Ser | Phe<br>295 | Ala |
| ATC | TGC | CAG | GGG | TGC | CTG | ACA | GCC | CTG | GGC | AGC | TAC | AAC | AAG | TAT | CAC | 1146 |
| Ile | Cys | Gln | Gly<br>300 | Cys | Leu | Thr | Ala | Leu<br>305 | Gly | Ser | Tyr | Asn | Lys<br>310 | Tyr | His |
| AAC | AAC | TGC | TAC | AAG | GAC | TGC | ATC | GCC | CTC | TGC | TTC | CTG | AAC | AGT | GCC | 1194 |
| Asn | Asn | Cys<br>315 | Tyr | Lys | Asp | Cys | Ile<br>320 | Ala | Leu | Cys | Phe | Leu<br>325 | Asn | Ser | Ala |
| ACC | AGC | TTT | GTG | GCT | GGG | TTT | GTT | GTC | TTC | TCC | ATC | CTG | GGC | TTC | ATG | 1242 |
| Thr | Ser<br>330 | Phe | Val | Ala | Gly<br>335 | Phe | Val | Val | Phe | Ser<br>340 | Ile | Leu | Gly | Phe | Met |
| TCC | CAA | GAG | CAA | GGG | GTG | CCC | ATT | TCT | GAA | GTG | GCC | GAG | TCA | GGT | CCT | 1290 |
| Ser<br>345 | Gln | Glu | Gln | Gly | Val<br>350 | Pro | Ile | Ser | Glu | Val<br>355 | Ala | Glu | Ser | Gly | Pro<br>360 |
| GGG | CTG | GCC | TTC | ATC | GCC | TTC | CCC | AAG | GCT | GTG | ACT | ATG | ATG | CCC | TTA | 1338 |
| Gly | Leu | Ala | Phe | Ile<br>365 | Ala | Phe | Pro | Lys | Ala<br>370 | Val | Thr | Met | Met | Pro<br>375 | Leu |
| TCC | CAG | CTG | TGG | TCC | TGC | CTG | TTT | TTC | ATG | CTC | ATA | TTC | CTA | GGG | | 1386 |
| Ser | Gln | Leu | Trp<br>380 | Ser | Cys | Leu | Phe | Phe<br>385 | Ile | Met | Leu | Ile | Phe<br>390 | Leu | Gly |
| CTG | GAC | AGC | CAG | TTT | GTC | TGT | GTG | GAG | TGC | CTG | GTG | ACA | GCC | TCC | ATA | 1434 |
| Leu | Asp | Ser<br>395 | Gln | Phe | Val | Cys | Val<br>400 | Glu | Cys | Leu | Val | Thr<br>405 | Ala | Ser | Ile |
| GAC | ATG | TTC | CCC | AGG | CAG | CTC | CGG | AAG | AGC | GGG | CGG | CGC | GAG | CTC | CTC | 1482 |
| Asp | Met<br>410 | Phe | Pro | Arg | Gln<br>415 | Leu | Arg | Lys | Ser | Gly<br>420 | Arg | Arg | Glu | Leu | Leu |
| ATC | CTC | ACC | ATC | GCC | GTC | ATG | TGC | TAC | CTG | ATA | GGG | CTT | TTC | CTG | GTC | 1530 |
| Ile | Leu<br>425 | Thr | Ile | Ala | Val<br>430 | Met | Cys | Tyr | Leu | Ile<br>435 | Gly | Leu | Phe | Leu | Val<br>440 |
| ACC | GAG | GGC | GGG | ATG | TAC | ATC | TTC | CAG | CTG | TTT | GAC | TAC | TAT | GCT | TCC | 1578 |
| Thr | Glu | Gly | Gly | Met<br>445 | Tyr | Ile | Phe | Gln | Leu<br>450 | Phe | Asp | Tyr | Tyr | Ala<br>455 | Ser |
| AGT | GGC | ATA | TGC | CTG | CTG | TTC | CTG | TCA | TTG | TTT | GAA | GTG | GTC | TGC | ATA | 1626 |
| Ser | Gly | Ile | Cys<br>460 | Leu | Leu | Phe | Leu | Ser<br>465 | Leu | Phe | Glu | Val | Val<br>470 | Cys | Ile |
| AGC | TGG | GTG | TAT | GGG | GCG | GAC | CGT | TTC | TAT | GAC | AAC | ATT | GAG | GAC | ATG | 1674 |

-continued

```
Ser Trp Val Tyr Gly Ala Asp Arg Phe Tyr Asp Asn Ile Glu Asp Met
        475                 480                 485

ATT GGC TAC CGG CCA TGG CCC CTG GTG AAG ATC TCC TGG CTC TTC CTG   1722
Ile Gly Tyr Arg Pro Trp Pro Leu Val Lys Ile Ser Trp Leu Phe Leu
    490                 495                 500

ACC CCT GGA CTT TGC CTG GCC ACT TTC CTC TTC TCC TTG AGC AAG TAC   1770
Thr Pro Gly Leu Cys Leu Ala Thr Phe Leu Phe Ser Leu Ser Lys Tyr
505                 510                 515                 520

ACC CCC CTC AAG TAC AAC AAC GTC TAT GTG TAC CCG CCC TGG GGA TAC   1818
Thr Pro Leu Lys Tyr Asn Asn Val Tyr Val Tyr Pro Pro Trp Gly Tyr
                525                 530                 535

TCC ATT GGC TGG TTC CTG GCT CTG TCC TCC ATG GTC TGT GTC CCA CTC   1866
Ser Ile Gly Trp Phe Leu Ala Leu Ser Ser Met Val Cys Val Pro Leu
            540                 545                 550

TTC GTC GTC ATC ACC CTC CTG AAG ACT CGG GGT CCT TTC AGG AAG CGT   1914
Phe Val Val Ile Thr Leu Leu Lys Thr Arg Gly Pro Phe Arg Lys Arg
        555                 560                 565

CTG CGT CAG CTC ATC ACC CCT GAC TCC AGT CTG CCA CAG CCC AAG CAA   1962
Leu Arg Gln Leu Ile Thr Pro Asp Ser Ser Leu Pro Gln Pro Lys Gln
    570                 575                 580

CAT CCC TGC TTG GAT GGC AGT GCT GGC CGG AAC TTT GGG CCC TCC CCA   2010
His Pro Cys Leu Asp Gly Ser Ala Gly Arg Asn Phe Gly Pro Ser Pro
585                 590                 595                 600

ACA AGG GAA GGA CTG ATA GCC GGG GAG AAG GAG ACC CAT TTG             2052
Thr Arg Glu Gly Leu Ile Ala Gly Glu Lys Glu Thr His Leu
                605                 610

TAGGGTGTGA CCAGAGGCCA GGCGGCTCCT AAGCCGGGAA CCTAGGTCAG GGCCACCCTC   2112

CATTCTCAGC GGACAGCCTC TGCCTCTGTC TCCTGCCACA ATCCTGCTGG GAACCTCTGG   2172

AGAGCCACAG GCACCCCCAG CTGGAGGCCA GACTCCTCTC TTGTG                    2217
```

( 2 ) INFORMATION FOR SEQ ID NO:2:

( i ) SEQUENCE CHARACTERISTICS:
        ( A ) LENGTH: 614 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Gly Lys Val Ala Val Gln Glu Tyr Gly Pro Pro Ala Val Ser
1               5                   10                  15

Trp Val Pro Glu Glu Gly Glu Lys Leu Asp Gln Glu Asp Glu Asp Gln
                20                  25                  30

Val Lys Asp Arg Gly Gln Trp Thr Asn Lys Met Glu Phe Val Leu Ser
            35                  40                  45

Val Ala Gly Glu Ile Ile Gly Leu Gly Asn Val Trp Arg Phe Pro Tyr
        50                  55                  60

Leu Cys Tyr Lys Asn Gly Gly Ala Phe Phe Ile Pro Tyr Phe Ile
65                  70                  75                  80

Phe Phe Phe Val Cys Gly Ile Pro Val Phe Phe Leu Glu Val Ala Leu
                85                  90                  95

Gly Gln Tyr Thr Ser Gln Gly Ser Val Thr Ala Trp Arg Lys Ile Cys
                100                 105                 110

Pro Leu Phe Gln Gly Ile Gly Leu Ala Ser Val Ile Glu Ser Tyr
            115                 120                 125

Leu Asn Val Tyr Tyr Ile Ile Ile Leu Ala Trp Ala Leu Phe Tyr Leu
        130                 135                 140
```

| | | | | | | | | | | | | | | | |
|---|---|---|---|---|---|---|---|---|---|---|---|---|---|---|---|
| Phe 145 | Ser | Ser | Phe | Thr | Ser 150 | Glu | Leu | Pro | Trp | Thr 155 | Cys | Asn | Asn | Phe 160 | |
| Trp | Asn | Thr | Glu | His 165 | Cys | Thr | Asp | Phe | Leu 170 | Asn | His | Ser | Gly | Ala 175 | Gly |
| Thr | Val | Thr | Pro 180 | Phe | Glu | Asn | Phe | Thr 185 | Ser | Pro | Val | Met | Glu 190 | Phe | Trp |
| Glu | Arg | Arg 195 | Val | Leu | Gly | Ile | Thr 200 | Ser | Gly | Ile | His | Asp 205 | Leu | Gly | Ser |
| Leu | Arg 210 | Trp | Glu | Leu | Ala | Leu 215 | Cys | Leu | Leu | Leu | Ala 220 | Trp | Val | Ile | Cys |
| Tyr 225 | Phe | Cys | Ile | Trp | Lys 230 | Gly | Val | Lys | Ser | Thr 235 | Gly | Lys | Val | Val | Tyr 240 |
| Phe | Thr | Ala | Thr | Phe 245 | Pro | Tyr | Leu | Met | Leu 250 | Val | Ile | Leu | Leu | Ile 255 | Arg |
| Gly | Val | Thr | Leu 260 | Pro | Gly | Ala | Tyr | Gln 265 | Gly | Ile | Ile | Tyr | Tyr 270 | Leu | Lys |
| Pro | Asp | Leu 275 | Phe | Arg | Leu | Lys | Asp 280 | Pro | Gln | Val | Trp | Met 285 | Asp | Ala | Gly |
| Thr | Gln 290 | Ile | Phe | Phe | Ser | Phe 295 | Ala | Ile | Cys | Gln | Gly 300 | Cys | Leu | Thr | Ala |
| Leu 305 | Gly | Ser | Tyr | Asn | Lys 310 | Tyr | His | Asn | Asn | Cys 315 | Tyr | Lys | Asp | Cys | Ile 320 |
| Ala | Leu | Cys | Phe | Leu 325 | Asn | Ser | Ala | Thr | Ser 330 | Phe | Val | Ala | Gly | Phe 335 | Val |
| Val | Phe | Ser | Ile 340 | Leu | Gly | Phe | Met | Ser 345 | Gln | Glu | Gln | Gly | Val 350 | Pro | Ile |
| Ser | Glu | Val 355 | Ala | Glu | Ser | Gly | Pro 360 | Gly | Leu | Ala | Phe | Ile 365 | Ala | Phe | Pro |
| Lys | Ala 370 | Val | Thr | Met | Met | Pro 375 | Leu | Ser | Gln | Leu | Trp 380 | Ser | Cys | Leu | Phe |
| Phe 385 | Ile | Met | Leu | Ile | Phe 390 | Leu | Gly | Leu | Asp | Ser 395 | Gln | Phe | Val | Cys | Val 400 |
| Glu | Cys | Leu | Val | Thr 405 | Ala | Ser | Ile | Asp | Met 410 | Phe | Pro | Arg | Gln | Leu 415 | Arg |
| Lys | Ser | Gly | Arg 420 | Arg | Glu | Leu | Leu | Ile 425 | Leu | Thr | Ile | Ala | Val 430 | Met | Cys |
| Tyr | Leu | Ile 435 | Gly | Leu | Phe | Leu | Val 440 | Thr | Glu | Gly | Gly | Met 445 | Tyr | Ile | Phe |
| Gln | Leu 450 | Phe | Asp | Tyr | Tyr | Ala 455 | Ser | Ser | Gly | Ile | Cys 460 | Leu | Leu | Phe | Leu |
| Ser 465 | Leu | Phe | Glu | Val | Val 470 | Cys | Ile | Ser | Trp | Val 475 | Tyr | Gly | Ala | Asp | Arg 480 |
| Phe | Tyr | Asp | Asn | Ile 485 | Glu | Asp | Met | Ile | Gly 490 | Tyr | Arg | Pro | Trp | Pro 495 | Leu |
| Val | Lys | Ile | Ser 500 | Trp | Leu | Phe | Leu | Thr 505 | Pro | Gly | Leu | Cys | Leu 510 | Ala | Thr |
| Phe | Leu | Phe 515 | Ser | Leu | Ser | Lys | Tyr 520 | Thr | Pro | Leu | Lys | Tyr 525 | Asn | Asn | Val |
| Tyr | Val 530 | Tyr | Pro | Pro | Trp | Gly 535 | Tyr | Ser | Ile | Gly | Trp 540 | Phe | Leu | Ala | Leu |
| Ser 545 | Ser | Met | Val | Cys | Val 550 | Pro | Leu | Phe | Val | Val 555 | Ile | Thr | Leu | Leu 560 | Lys |
| Thr | Arg | Gly | Pro | Phe 565 | Arg | Lys | Arg | Leu | Arg 570 | Gln | Leu | Ile | Thr | Pro 575 | Asp |

Ser Ser Leu Pro Gln Pro Lys Gln His Pro Cys Leu Asp Gly Ser Ala
            580                 585                 590

Gly Arg Asn Phe Gly Pro Ser Pro Thr Arg Glu Gly Leu Ile Ala Gly
        595                 600                 605

Glu Lys Glu Thr His Leu
    610

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GTCCTGAAGA TCTCAGATGG CATCCAGCAC CTGGGGTCCC TGCGC        45

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: YES ( x i ) SEQUENCE DESCRIPTION: SEQ ID NO:4:

GCAGGAGGCA CAGGACCAGC TCCCAGCGCA GGGACCCCAG GTGCT        45

( 2 ) INFORMATION FOR SEQ ID NO:5:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CCCATAAGCT GTGGTATCCC AGTGTTCTTC CTGGAGGTGG CACTGGGTCA GTATAGCAGC    60
CAGGGGAGTG TTACTGCTTG GAGGAAGATC TGTCCCCTTC TCCAAGGCAT TGGCATGGCA    120
TCTGTGGTCA TCGAGTCTTA TTTGAACATC TACTACATCA TCATCCTTGC CTGGGCTCTC    180
TTCTACCTGT TCAGCTCCTT CACCTGGGAG CTTCCCTGGA CAACCTGCAC CAACTCCTGG    240
AACACAGAAC ATTGCGTGGA CTTTCTGAAC TACTCATCGA CCAGAGCCGC AAGCTACTCT    300
GAGAACTTCA CCTCACCAGT CATGGAATTC TGGGAGAGAC GGGTTTTGGG TATTACATCA    360
GGCATCCATG ACCTGGGGTC CCTGCGCTGG GAGCTGGCCC TGTGCCTCCT GCTCGCCTGG    420
ATC    423

( 2 ) INFORMATION FOR SEQ ID NO:6:

( i ) SEQUENCE CHARACTERISTICS:
        ( A ) LENGTH: 139 amino acids
        ( B ) TYPE: amino acid
        ( D ) TOPOLOGY: linear (ii) MOLECULE TYPE: protein ( x i ) SEQUENCE DESCRIPTION: SEQ ID NO:6:

```
Ser Cys Gly Ile Pro Val Phe Phe Leu Glu Val Ala Leu Gly Gln Tyr
  1               5                      10                      15

Ser Ser Gln Gly Ser Val Thr Ala Trp Arg Lys Ile Cys Pro Leu Leu
              20                      25                      30

Gln Gly Ile Gly Met Ala Ser Val Val Ile Glu Ser Tyr Leu Asn Ile
              35                      40                      45

Tyr Tyr Ile Ile Ile Leu Ala Trp Ala Leu Phe Tyr Leu Phe Ser Ser
     50                      55                      60

Phe Thr Trp Glu Leu Pro Trp Thr Thr Cys Thr Asn Ser Trp Asn Thr
 65                      70                      75                      80

Glu His Cys Val Asp Phe Leu Asn Tyr Ser Ser Thr Arg Ala Ala Ser
                 85                      90                      95

Tyr Ser Glu Asn Phe Thr Ser Pro Val Met Glu Phe Trp Glu Arg Arg
             100                     105                     110

Val Leu Gly Ile Thr Ser Gly Ile His Asp Leu Gly Ser Leu Arg Trp
             115                     120                     125

Glu Leu Ala Leu Cys Leu Leu Leu Ala Trp Ile
             130                     135
```

( 2 ) INFORMATION FOR SEQ ID NO:7:

( i ) SEQUENCE CHARACTERISTICS:
        ( A ) LENGTH: 614 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Asp Arg Lys Val Ala Val His Glu Asp Gly Tyr Pro Val Val Ser
  1               5                      10                      15

Trp Val Pro Glu Glu Gly Glu Met Met Asp Gln Lys Gly Lys Asp Gln
              20                      25                      30

Val Lys Asp Arg Gly Gln Trp Thr Asn Lys Met Glu Phe Val Leu Ser
              35                      40                      45

Val Ala Gly Glu Ile Ile Gly Leu Gly Asn Val Trp Arg Phe Pro Tyr
     50                      55                      60

Leu Cys Tyr Lys Asn Gly Gly Gly Ala Phe Phe Ile Pro Tyr Phe Ile
 65                      70                      75                      80

Phe Phe Phe Ser Cys Gly Ile Pro Val Phe Phe Leu Glu Val Ala Leu
                 85                      90                      95

Gly Gln Tyr Ser Ser Gln Gly Ser Val Thr Ala Trp Arg Lys Ile Cys
             100                     105                     110

Pro Leu Leu Gln Gly Ile Gly Met Ala Ser Val Val Ile Glu Ser Tyr
             115                     120                     125

Leu Asn Ile Tyr Tyr Ile Ile Ile Leu Ala Trp Ala Leu Phe Tyr Leu
     130                     135                     140

Phe Ser Ser Phe Thr Trp Glu Leu Pro Trp Thr Thr Cys Thr Asn Ser
145                     150                     155                     160

Trp Asn Thr Glu His Cys Val Asp Phe Leu Asn His Ser Ser Ala Arg
                 165                     170                     175

Gly Val Ser Ser Ser Glu Asn Phe Thr Ser Pro Val Met Glu Phe Trp
             180                     185                     190

Glu Arg Arg Val Leu Gly Ile Thr Ser Gly Ile His Asp Leu Gly Ser
             195                     200                     205

Leu Arg Trp Glu Leu Ala Leu Cys Leu Leu Leu Ala Trp Ile Ile Cys
```

-continued

|   |   |   |   | 210 |   |   |   |   | 215 |   |   |   |   | 220 |   |   |
|---|---|---|---|---|---|---|---|---|---|---|---|---|---|---|---|---|
| Tyr 225 | Phe | Cys | Ile | Trp 230 | Lys | Gly | Val | Lys | Ser 235 | Thr | Gly | Lys | Val | Val | Tyr 240 |
| Phe | Thr | Ala | Thr | Phe 245 | Pro | Tyr | Leu | Met | Leu 250 | Ile | Ile | Leu | Leu | Ile 255 | Arg |
| Gly | Val | Thr | Leu 260 | Pro | Gly | Ala | Tyr | Gln 265 | Gly | Ile | Val | Phe | Tyr 270 | Leu | Lys |
| Pro | Asp | Leu 275 | Leu | Arg | Leu | Lys | Asp 280 | Pro | Gln | Val | Trp | Met 285 | Asp | Ala | Gly |
| Thr | Gln 290 | Ile | Phe | Phe | Ser | Phe 295 | Ala | Ile | Cys | Gln | Gly 300 | Cys | Leu | Thr | Ala |
| Leu 305 | Gly | Ser | Tyr | Asn | Lys 310 | Tyr | His | Asn | Asn | Cys 315 | Tyr | Arg | Asp | Ser | Ile 320 |
| Ala | Leu | Cys | Phe | Leu 325 | Asn | Ser | Ala | Thr | Ser 330 | Phe | Val | Ala | Gly | Phe 335 | Val |
| Asx | Phe | Ser | Ile 340 | Leu | Gly | Phe | Met | Ser 345 | Gln | Glu | Gln | Gly | Ile 350 | Pro | Ile |
| Ser | Glu | Val 355 | Ala | Glu | Ser | Gly | Pro 360 | Gly | Leu | Ala | Phe | Ile 365 | Ala | Phe | Pro |
| Lys | Ala 370 | Val | Thr | Met | Met | Pro 375 | Leu | Ser | Gln | Leu | Trp 380 | Ser | Cys | Leu | Phe |
| Phe 385 | Ile | Met | Leu | Leu | Phe 390 | Leu | Gly | Leu | Asp | Ser 395 | Gln | Phe | Val | Cys | Met 400 |
| Glu | Cys | Leu | Val | Thr 405 | Ala | Ser | Met | Asp | Met 410 | Phe | Pro | Gln | Gln | Leu 415 | Arg |
| Lys | Ser | Gly | Arg 420 | Arg | Asp | Val | Leu | Ile 425 | Leu | Ala | Ile | Ser | Val 430 | Leu | Cys |
| Tyr | Leu | Met 435 | Gly | Leu | Leu | Leu | Val 440 | Thr | Ala | Gly | Gly | Met 445 | Tyr | Ile | Phe |
| Gln | Leu 450 | Phe | Asp | Tyr | Tyr | Ala 455 | Ser | Ser | Gly | Ile | Cys 460 | Leu | Leu | Phe | Leu |
| Ser 465 | Leu | Phe | Glu | Val | Ile 470 | Cys | Ile | Gly | Trp | Val 475 | Tyr | Gly | Ala | Asp | Arg 480 |
| Phe | Tyr | Asp | Asn | Val 485 | Glu | Asp | Met | Ile | Gly 490 | Tyr | Arg | Pro | Trp | Pro 495 | Leu |
| Val | Lys | Ile | Ser 500 | Trp | Leu | Phe | Leu | Thr 505 | Pro | Gly | Leu | Cys | Leu 510 | Ala | Thr |
| Phe | Phe | Phe 515 | Ser | Leu | Ser | Lys | Tyr 520 | Thr | Pro | Leu | Lys | Tyr 525 | Asn | Asn | Val |
| Tyr | Met 530 | Tyr | Pro | Ser | Trp | Gly 535 | Tyr | Ser | Ile | Gly | Trp 540 | Leu | Leu | Ala | Phe |
| Ser 545 | Ser | Met | Ala | Cys | Val 550 | Pro | Leu | Phe | Ile | Ile 555 | Thr | Phe | Leu | Lys 560 |
| Thr | Gln | Gly | Ser | Phe 565 | Lys | Lys | Arg | Leu | Arg 570 | Arg | Leu | Ile | Thr | Pro 575 | Asp |
| Pro | Ser | Leu | Pro 580 | Gln | Pro | Gly | Arg | Arg 585 | Pro | Pro | Gln | Asp | Gly 590 | Ser | Ser |
| Ala | Gln | Asn 595 | Cys | Ser | Ser | Ser | Pro 600 | Ala | Lys | Gln | Glu | Leu 605 | Ile | Ala | Trp |
| Glu | Lys | Glu | Thr | His | Leu |   |   |   |   |   |   |   |   |   |   |
|   |   |   | 610 |   |   |   |   |   |   |   |   |   |   |   |   |

( 2 ) INFORMATION FOR SEQ ID NO:8:

( i ) SEQUENCE CHARACTERISTICS:
   ( A ) LENGTH: 614 amino acids
   ( B ) TYPE: amino acid
   ( D ) TOPOLOGY: linear ( i i ) MOLECULE TYPE: protein ( x i ) SEQUENCE DESCRIPTION: SEQ ID NO:8:

| Met | Asp | Arg | Lys | Val | Ala | Val | Pro | Glu | Asp | Gly | Pro | Pro | Val | Ser |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Trp | Leu | Pro | Glu | Glu | Gly | Glu | Lys | Leu | Asp | Gln | Glu | Gly | Asp | Gln |
|     |     |     | 20  |     |     |     |     | 25  |     |     |     | 30  |     |     |
| Val | Lys | Asp | Arg | Gly | Gln | Trp | Thr | Asn | Lys | Met | Glu | Phe | Val | Leu | Ser |
|     |     | 35  |     |     |     |     | 40  |     |     |     |     | 45  |     |     |
| Val | Ala | Gly | Glu | Ile | Ile | Gly | Leu | Gly | Asn | Val | Trp | Arg | Phe | Pro | Tyr |
|     |     | 50  |     |     |     | 55  |     |     |     |     | 60  |     |     |     |
| Leu | Cys | Tyr | Lys | Asn | Gly | Gly | Gly | Ala | Phe | Phe | Ile | Pro | Tyr | Phe | Ile |
| 65  |     |     |     |     | 70  |     |     |     |     | 75  |     |     |     |     | 80  |
| Phe | Phe | Phe | Thr | Cys | Gly | Ile | Pro | Val | Phe | Phe | Leu | Glu | Val | Ala | Leu |
|     |     |     |     | 85  |     |     |     |     | 90  |     |     |     |     | 95  |
| Gly | Gln | Tyr | Thr | Ser | Gln | Gly | Ser | Val | Thr | Ala | Trp | Arg | Lys | Ile | Cys |
|     |     |     | 100 |     |     |     |     | 105 |     |     |     |     | 110 |     |
| Pro | Leu | Leu | Gln | Gly | Ile | Gly | Leu | Ala | Ser | Val | Val | Ile | Glu | Ser | Tyr |
|     |     | 115 |     |     |     |     | 120 |     |     |     |     | 125 |     |     |
| Leu | Asn | Ile | Tyr | Tyr | Ile | Ile | Ile | Leu | Ala | Trp | Ala | Leu | Phe | Tyr | Leu |
|     | 130 |     |     |     |     | 135 |     |     |     |     | 140 |     |     |     |
| Phe | Ser | Ser | Phe | Thr | Ser | Glu | Leu | Pro | Trp | Thr | Thr | Cys | Thr | Asn | Thr |
| 145 |     |     |     |     | 150 |     |     |     |     | 155 |     |     |     |     | 160 |
| Trp | Asn | Thr | Glu | His | Cys | Met | Asp | Phe | Leu | Asn | His | Ser | Gly | Ala | Arg |
|     |     |     |     | 165 |     |     |     |     | 170 |     |     |     |     | 175 |
| Thr | Ala | Thr | Ser | Ser | Glu | Asn | Phe | Thr | Ser | Pro | Val | Asn | Glu | Phe | Trp |
|     |     |     | 180 |     |     |     |     | 185 |     |     |     |     | 190 |     |
| Glu | Arg | Arg | Val | Leu | Gly | Ile | Thr | Ser | Gly | Ile | His | Asp | Leu | Gly | Ala |
|     |     | 195 |     |     |     |     | 200 |     |     |     |     | 205 |     |     |
| Leu | Arg | Trp | Glu | Leu | Ala | Leu | Cys | Leu | Leu | Leu | Ala | Trp | Leu | Ile | Cys |
|     | 210 |     |     |     |     | 215 |     |     |     |     | 220 |     |     |     |
| Tyr | Phe | Cys | Ile | Trp | Lys | Gly | Val | Lys | Thr | Thr | Gly | Lys | Val | Val | Tyr |
| 225 |     |     |     |     | 230 |     |     |     |     | 235 |     |     |     |     | 240 |
| Phe | Thr | Ala | Thr | Phe | Pro | Tyr | Leu | Met | Leu | Val | Ile | Leu | Leu | Ile | Arg |
|     |     |     |     | 245 |     |     |     |     | 250 |     |     |     |     | 255 |
| Gly | Ile | Thr | Leu | Pro | Gly | Ala | Tyr | Gln | Gly | Val | Ile | Tyr | Tyr | Leu | Lys |
|     |     |     | 260 |     |     |     |     | 265 |     |     |     |     | 270 |     |
| Pro | Asp | Leu | Leu | Arg | Leu | Lys | Asp | Pro | Gln | Val | Trp | Asn | Asp | Ala | Gly |
|     |     | 275 |     |     |     |     | 280 |     |     |     |     | 285 |     |     |
| Thr | Gln | Ile | Phe | Phe | Ser | Phe | Ala | Ile | Cys | Gln | Gly | Cys | Leu | Thr | Ala |
|     | 290 |     |     |     | 295 |     |     |     |     | 300 |     |     |     |     |
| Leu | Gly | Ser | Tyr | Asn | Lys | Tyr | His | Asn | Asn | Cys | Tyr | Arg | Asp | Ser | Ile |
| 305 |     |     |     |     | 310 |     |     |     |     | 315 |     |     |     |     | 320 |
| Ala | Leu | Cys | Phe | Leu | Asn | Ser | Ala | Thr | Ser | Phe | Ala | Ala | Gly | Phe | Val |
|     |     |     |     | 325 |     |     |     |     | 330 |     |     |     |     | 335 |
| Val | Phe | Ser | Ile | Leu | Gly | Phe | Met | Ala | Gln | Glu | Gln | Gly | Leu | Pro | Ile |
|     |     |     | 340 |     |     |     |     | 345 |     |     |     |     | 350 |     |
| Ser | Glu | Val | Ala | Glu | Ser | Gly | Pro | Gly | Leu | Ala | Phe | Ile | Ala | Phe | Pro |
|     |     | 355 |     |     |     |     | 360 |     |     |     |     | 365 |     |     |
| Lys | Ala | Val | Thr | Met | Met | Pro | Leu | Ser | Gln | Leu | Trp | Ser | Cys | Leu | Phe |
|     | 370 |     |     |     |     | 375 |     |     |     |     | 380 |     |     |     |

| | | | | | | | | | | | | | | |
|---|---|---|---|---|---|---|---|---|---|---|---|---|---|---|
| Phe 385 | Ile | Met | Leu | Ile | Phe 390 | Leu | Gly | Leu | Asp | Ser 395 | Gln | Phe | Val | Cys Val 400 |
| Glu | Cys | Leu | Val | Thr 405 | Ala | Ser | Met | Asp | Met 410 | Phe | Pro | Ser | Gln | Leu Arg 415 |
| Lys | Ser | Gly | Arg 420 | Arg | Glu | Leu | Leu | Ile 425 | Leu | Ala | Ile | Ala | Val 430 | Phe Cys |
| Tyr | Leu | Ala 435 | Gly | Leu | Phe | Leu | Val 440 | Thr | Glu | Gly | Gly | Met 445 | Tyr | Ile Phe |
| Gln | Leu 450 | Phe | Asp | Tyr | Tyr | Ala 455 | Ser | Ser | Gly | Ile | Cys 460 | Leu | Leu | Phe Leu |
| Ala 465 | Met | Phe | Glu | Val | Ile 470 | Cys | Ile | Ser | Trp | Val 475 | Tyr | Gly | Ala | Asp Arg 480 |
| Phe | Tyr | Asp | Asn | Ile 485 | Glu | Asp | Met | Ile | Gly 490 | Tyr | Arg | Pro | Trp | Pro Leu 495 |
| Val | Lys | Ile | Ser 500 | Trp | Leu | Phe | Leu | Thr 505 | Pro | Gly | Leu | Cys | Leu 510 | Ala Thr |
| Phe | Leu | Phe 515 | Ser | Leu | Ser | Gln | Tyr 520 | Thr | Pro | Leu | Lys | Tyr 525 | Asn | Asn Ile |
| Tyr | Val 530 | Tyr | Pro | Pro | Trp | Gly 535 | Tyr | Ser | Ile | Gly | Trp 540 | Phe | Leu | Ala Leu |
| Ser 545 | Ser | Met | Ile | Cys | Val 550 | Pro | Leu | Phe | Val | Ile 555 | Ile | Thr | Leu | Leu Lys 560 |
| Thr | Arg | Gly | Ser | Phe 565 | Lys | Lys | Arg | Leu | Arg 570 | Gln | Leu | Thr | Thr 575 | Pro Asp |
| Pro | Ser | Leu | Pro 580 | Gln | Pro | Lys | Gln | His 585 | Leu | Tyr | Leu | Asp | Gly 590 | Gly Thr |
| Ser | Gln | Asp 595 | Cys | Gly | Pro | Ser | Pro 600 | Thr | Lys | Glu | Gly | Leu 605 | Ile | Val Gly |
| Glu | Lys 610 | Glu | Thr | His | Leu | | | | | | | | | |

( 2 ) INFORMATION FOR SEQ ID NO:9:

( i ) SEQUENCE CHARACTERISTICS:
        ( A ) LENGTH: 602 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met 1 | Asp | Asn | Arg | Val 5 | Ser | Gly | Thr | Thr | Ser 10 | Asn | Gly | Glu | Thr | Lys Pro 15 |
| Val | Cys | Pro | Val 20 | Met | Glu | Lys | Val | Glu 25 | Glu | Asp | Gly | Thr | Leu 30 | Glu Arg |
| Glu | Gln | Trp 35 | Thr | Asn | Lys | Met | Glu 40 | Phe | Val | Leu | Ser | Val 45 | Ala | Gly Glu |
| Ile | Ile 50 | Gly | Leu | Gly | Asn | Val 55 | Trp | Arg | Phe | Pro | Tyr 60 | Leu | Cys | Tyr Lys |
| Asn 65 | Gly | Gly | Gly | Ala | Phe 70 | Glu | Ile | Pro | Tyr | Leu 75 | Ile | Phe | Leu | Phe Thr 80 |
| Cys | Gly | Ile | Pro | Val 85 | Phe | Phe | Leu | Glu | Thr 90 | Ala | Leu | Gly | Gln 95 | Tyr Thr |
| Asn | Gln | Gly | Gly 100 | Ile | Thr | Ala | Trp | Arg 105 | Lys | Ile | Cys | Pro | Ile 110 | Phe Glu |
| Gly | Ile | Gly | Tyr | Ala | Ser | Gln | Met | Ile | Val | Ser | Leu | Leu | Asn | Val Tyr |

115                           120                            125

Tyr  Ile  Val  Val  Leu  Ala  Trp  Ala  Leu  Phe  Tyr  Leu  Phe  Ser  Ser  Phe
     130                      135                 140

Thr  Thr  Asp  Leu  Pro  Trp  Gly  Ser  Cys  Ser  His  Glu  Trp  Asn  Thr  Glu
145                           150                 155                           160

Asn  Cys  Val  Glu  Phe  Gln  Lys  Thr  Asn  Asn  Ser  Leu  Asn  Val  Thr  Ser
                    165                 170                          175

Glu  Asn  Ala  Thr  Ser  Pro  Val  Ile  Glu  Phe  Trp  Glu  Arg  Arg  Val  Leu
               180                 185                      190

Lys  Ile  Ser  Asp  Gly  Ile  Gln  His  Leu  Gly  Ser  Leu  Arg  Trp  Glu  Leu
          195                      200                 205

Val  Leu  Cys  Leu  Leu  Leu  Ala  Trp  Ile  Ile  Cys  Tyr  Phe  Cys  Ile  Trp
     210                      215                      220

Lys  Gly  Val  Lys  Ser  Thr  Gly  Lys  Val  Val  Tyr  Phe  Thr  Ala  Thr  Phe
225                           230                 235                           240

Pro  Tyr  Leu  Met  Leu  Val  Val  Leu  Leu  Ile  Arg  Gly  Val  Thr  Leu  Pro
               245                      250                           255

Gly  Ala  Ala  Gln  Gly  Ile  Gln  Phe  Tyr  Leu  Tyr  Pro  Asn  Ile  Thr  Arg
               260                      265                      270

Leu  Trp  Asp  Pro  Gln  Val  Trp  Asn  Asp  Ala  Gly  Thr  Gln  Ile  Phe  Phe
          275                      280                 285

Ser  Phe  Ala  Ile  Cys  Leu  Gly  Cys  Leu  Thr  Ala  Leu  Gly  Ser  Tyr  Asn
     290                      295                 300

Lys  Tyr  His  Asn  Asn  Cys  Tyr  Arg  Asp  Cys  Val  Ala  Leu  Cys  Ile  Leu
305                           310                 315                           320

Asn  Ser  Ser  Thr  Ser  Phe  Val  Ala  Gly  Phe  Ala  Ile  Phe  Ser  Ile  Leu
                    325                      330                      335

Gly  Phe  Asn  Ser  Gln  Glu  Gln  Gly  Val  Pro  Ile  Ser  Glu  Val  Ala  Glu
               340                      345                 350

Ser  Gly  Pro  Gly  Leu  Ala  Phe  Ile  Ala  Tyr  Pro  Arg  Ala  Val  Val  Asn
          355                      360                 365

Leu  Pro  Phe  Ser  Pro  Leu  Trp  Ala  Cys  Cys  Phe  Phe  Phe  Asn  Val  Val
     370                      375                 380

Leu  Leu  Gly  Leu  Asp  Ser  Gln  Phe  Val  Cys  Val  Glu  Ser  Leu  Val  Thr
385                      390                      395                           400

Ala  Leu  Val  Asp  Asn  Tyr  Pro  Arg  Val  Phe  Arg  Lys  Lys  Asn  Arg  Arg
                    405                      410                      415

Glu  Ile  Leu  Ile  Leu  Ile  Val  Ser  Val  Val  Ser  Phe  Phe  Ile  Gly  Leu
               420                      425                 430

Ile  Met  Leu  Thr  Glu  Gly  Gly  Asn  Tyr  Val  Phe  Gln  Leu  Phe  Asp  Tyr
          435                      440                 445

Tyr  Ala  Ala  Ser  Gly  Met  Cys  Leu  Leu  Phe  Val  Ala  Ile  Phe  Glu  Ser
     450                      455                 460

Leu  Cys  Val  Ala  Trp  Val  Tyr  Gly  Ala  Ser  Arg  Phe  Tyr  Asp  Asn  Ile
465                      470                 475                           480

Glu  Asp  Met  Ile  Gly  Tyr  Lys  Pro  Trp  Pro  Leu  Ile  Lys  Tyr  Cys  Trp
               485                      490                 495

Leu  Phe  Phe  Thr  Pro  Ala  Val  Cys  Leu  Ala  Thr  Phe  Leu  Phe  Ser  Leu
               500                 505                 510

Ile  Lys  Tyr  Thr  Pro  Leu  Thr  Tyr  Asn  Lys  Lys  Tyr  Thr  Tyr  Pro  Trp
          515                      520                 525

Trp  Gly  Asp  Ala  Leu  Gly  Trp  Leu  Leu  Ala  Leu  Ser  Ser  Met  Val  Cys
     530                      535                 540

```
Ile  Pro  Ala  Trp  Ser  Ile  Tyr  Lys  Leu  Arg  Thr  Leu  Lys  Gly  Pro  Leu
545            550                      555                      560

Arg  Glu  Arg  Leu  Arg  Gln  Leu  Val  Cys  Pro  Ala  Glu  Asp  Leu  Pro  Gln
                    565                 570                      575

Lys  Ser  Gln  Pro  Glu  Leu  Thr  Ser  Pro  Ala  Thr  Pro  Met  Thr  Ser  Leu
               580                      585                      590

Leu  Arg  Leu  Thr  Glu  Leu  Glu  Ser  Asn  Cys
          595                      600
```

( 2 ) INFORMATION FOR SEQ ID NO:10:

( i ) SEQUENCE CHARACTERISTICS:
        ( A ) LENGTH: 627 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Thr  Ala  Glu  Gln  Ala  Leu  Pro  Leu  Gly  Asn  Gly  Lys  Ala  Ala  Glu
1                   5                        10                       15

Glu  Ala  Arg  Gly  Ser  Glu  Ala  Leu  Gly  Gly  Gly  Gly  Gly  Gly  Ala  Ala
               20                  25                       30

Gly  Thr  Arg  Glu  Ala  Arg  Asp  Lys  Ala  Val  His  Glu  Arg  Gly  His  Trp
          35                  40                       45

Asn  Asn  Lys  Val  Glu  Phe  Val  Leu  Ser  Val  Ala  Gly  Glu  Ile  Ile  Gly
50                       55                       60

Leu  Gly  Asn  Val  Trp  Arg  Phe  Pro  Tyr  Leu  Cys  Tyr  Lys  Asn  Gly  Gly
65                  70                       75                       80

Gly  Ala  Phe  Leu  Ile  Pro  Tyr  Val  Val  Phe  Phe  Ile  Cys  Cys  Gly  Ile
               85                       90                       95

Pro  Val  Phe  Phe  Leu  Glu  Thr  Ala  Leu  Gly  Gln  Phe  Thr  Ser  Glu  Gly
               100                      105                      110

Gly  Ile  Thr  Cys  Trp  Arg  Arg  Val  Cys  Pro  Leu  Phe  Glu  Gly  Ile  Gly
          115                      120                      125

Tyr  Ala  Thr  Gln  Val  Ile  Glu  Ala  His  Leu  Asn  Val  Tyr  Tyr  Ile  Ile
     130                      135                      140

Ile  Leu  Ala  Trp  Ala  Ile  Phe  Tyr  Leu  Ser  Asn  Cys  Phe  Thr  Thr  Glu
145                      150                      155                      160

Leu  Pro  Trp  Ala  Thr  Cys  Gly  His  Glu  Trp  Asn  Thr  Glu  Lys  Cys  Val
                    165                      170                      175

Glu  Phe  Gln  Lys  Leu  Asn  Phe  Ser  Asn  Tyr  Ser  His  Val  Ser  Leu  Gln
               180                      185                      190

Asn  Ala  Thr  Ser  Pro  Val  Met  Glu  Phe  Trp  Glu  Arg  Arg  Val  Leu  Ala
          195                      200                      205

Ile  Ser  Asp  Gly  Ile  Glu  His  Ile  Gly  Asn  Leu  Arg  Trp  Glu  Leu  Ala
     210                      215                      220

Leu  Cys  Leu  Leu  Ala  Ala  Trp  Thr  Ile  Cys  Tyr  Phe  Cys  Ile  Trp  Lys
225                      230                      235                      240

Gly  Thr  Lys  Ser  Thr  Gly  Lys  Val  Val  Tyr  Val  Thr  Ala  Thr  Phe  Pro
               245                      250                      255

Tyr  Ile  Asn  Leu  Leu  Ile  Leu  Leu  Ile  Arg  Gly  Val  Thr  Leu  Pro  Gly
          260                      265                      270

Ala  Ser  Glu  Gly  Ile  Lys  Phe  Tyr  Leu  Tyr  Pro  Asp  Leu  Ser  Arg  Leu
     275                      280                      285

Ser  Asp  Pro  Gln  Val  Trp  Val  Asp  Ala  Gly  Thr  Gln  Ile  Phe  Phe  Ser
290                      295                      300
```

| | | | | | | | | | | | | | | |
|---|---|---|---|---|---|---|---|---|---|---|---|---|---|---|
| Tyr 305 | Ala | Ile | Cys | Leu | Gly 310 | Cys | Leu | Thr | Ala | Leu 315 | Gly | Ser | Tyr | Asn | Asn 320 |
| Tyr | Asn | Asn | Asn | Cys 325 | Tyr | Arg | Asp | Cys | Ile 330 | Met | Leu | Cys | Cys | Leu 335 | Asn |
| Ser | Gly | Thr | Ser 340 | Phe | Val | Ala | Gly | Phe 345 | Ala | Ile | Phe | Ser | Val 350 | Leu | Gly |
| Phe | Met | Ala 355 | Tyr | Glu | Gln | Gly | Val 360 | Pro | Ile | Ala | Glu | Val 365 | Ala | Glu | Ser |
| Gly | Pro 370 | Gly | Leu | Ala | Phe | Ile 375 | Ala | Tyr | Pro | Lys | Ala 380 | Val | Thr | Met | Asn |
| Pro 385 | Leu | Ser | Pro | Leu | Trp 390 | Ala | Thr | Leu | Phe | Phe 395 | Met | Asn | Leu | Ile | Phe 400 |
| Leu | Gly | Leu | Asp | Ser 405 | Gln | Phe | Val | Cys | Val 410 | Glu | Ser | Leu | Val | Thr 415 | Ala |
| Val | Val | Asp | Asn 420 | Tyr | Pro | Lys | Val | Phe 425 | Arg | Arg | Gly | Tyr | Arg 430 | Arg | Glu |
| Leu | Leu | Ile 435 | Leu | Ala | Leu | Ser | Ile 440 | Val | Ser | Tyr | Phe | Leu 445 | Gly | Leu | Val |
| Met | Leu 450 | Thr | Glu | Gly | Gly | Met 455 | Tyr | Ile | Phe | Gln | Leu 460 | Phe | Asp | Ser | Tyr |
| Ala 465 | Ala | Ser | Gly | Met | Cys 470 | Leu | Leu | Phe | Val | Ala 475 | Ile | Phe | Glu | Cys | Val 480 |
| Cys | Ile | Gly | Trp | Val 485 | Tyr | Gly | Ser | Asn | Arg 490 | Phe | Tyr | Asp | Asn | Ile 495 | Glu |
| Asp | Met | Ile | Gly 500 | Tyr | Arg | Pro | Leu | Ser 505 | Leu | Ile | Lys | Trp | Cys 510 | Trp | Lys |
| Val | Val | Thr 515 | Pro | Gly | Ile | Cys | Ala 520 | Gly | Ile | Phe | Ile | Phe 525 | Phe | Leu | Val |
| Lys | Tyr 530 | Lys | Pro | Leu | Lys | Tyr 535 | Asn | Asn | Val | Tyr | Thr 540 | Tyr | Pro | Ala | Trp |
| Gly 545 | Tyr | Gly | Ile | Gly | Trp 550 | Leu | Met | Ala | Leu | Ser 555 | Ser | Met | Leu | Cys | Ile 560 |
| Pro | Leu | Trp | Ile | Phe 565 | Ile | Lys | Leu | Trp | Lys 570 | Thr | Glu | Gly | Thr | Leu 575 | Pro |
| Glu | Lys | Leu | Gln 580 | Lys | Leu | Thr | Val | Pro 585 | Ser | Ala | Asp | Leu | Lys 590 | Met | Arg |
| Gly | Lys | Leu 595 | Gly | Ala | Ser | Pro | Arg 600 | Met | Val | Thr | Val | Asn 605 | Asp | Cys | Glu |
| Ala | Lys 610 | Val | Lys | Gly | Asp | Gly 615 | Thr | Ile | Ser | Ala | Ile 620 | Thr | Glu | Lys | Glu |
| Thr 625 | His | Phe | | | | | | | | | | | | | |